(12) United States Patent
D'Angelo et al.

(10) Patent No.: US 11,257,587 B1
(45) Date of Patent: Feb. 22, 2022

(54) COMPUTER-BASED SYSTEMS, IMPROVED COMPUTING COMPONENTS AND/OR IMPROVED COMPUTING OBJECTS CONFIGURED FOR REAL TIME ACTIONABLE DATA TRANSFORMATIONS TO ADMINISTER HEALTHCARE FACILITIES AND METHODS OF USE THEREOF

(71) Applicants: John D'Angelo, Bayport, NY (US); Eric Cruzen, New York, NY (US)

(72) Inventors: John D'Angelo, Bayport, NY (US); Eric Cruzen, New York, NY (US)

(73) Assignee: The Feinstein Institutes For Medical Research, Inc., Manhasset, NY (US)

( * ) Notice: Subject to any disclaimer, the term of this patent is extended or adjusted under 35 U.S.C. 154(b) by 19 days.

(21) Appl. No.: 16/565,748

(22) Filed: Sep. 10, 2019

Related U.S. Application Data

(60) Provisional application No. 62/848,765, filed on May 16, 2019.

(51) Int. Cl.
*G16H 40/20* (2018.01)
*G06Q 10/06* (2012.01)
*G16H 10/60* (2018.01)
*A61B 5/00* (2006.01)

(52) U.S. Cl.
CPC .......... *G16H 40/20* (2018.01); *A61B 5/0022* (2013.01); *G06Q 10/06315* (2013.01); *G16H 10/60* (2018.01)

(58) Field of Classification Search
CPC .................. G16H 40/20; G06Q 10/06315
See application file for complete search history.

(56) References Cited

U.S. PATENT DOCUMENTS

| 8,515,777 | B1 * | 8/2013 | Rajasenan | G06Q 10/06313 |
| | | | | 705/2 |
| 9,946,840 | B1 * | 4/2018 | Kemp | G16H 50/30 |
| 2006/0287906 | A1 * | 12/2006 | McGillin | G16H 40/20 |
| | | | | 705/2 |

(Continued)

*Primary Examiner* — Janice A Mooneyham
*Assistant Examiner* — Karen A Hranek
(74) *Attorney, Agent, or Firm* — Greenberg Traurig, LLP

(57) ABSTRACT

Embodiments of systems and methods of the present disclosure include a database layer queries patient-related raw data from data tables of distinct data collection services, normalizes the patient-related raw data to produce common format normalized patient-related data, and stores the common format normalized patient-related data. An algorithmic processing layer, in real-time, analyzes the common format normalized patient-related data based on patient-related data metrics, a healthcare facility-related data metrics, or both, to determine patient-related data points, where each patient-related data point is associated with a respective threshold condition and a respective ranking score, ranks the patient-related data points based on the threshold condition and the ranking score to determine a priority, and generates actionable medical directives related to patients, where the actionable medical directives cause real-time operational changes in the way that the healthcare facility services the patients. And a visualization layer presents, in real-time, the actionable medical directives.

17 Claims, 51 Drawing Sheets
(45 of 51 Drawing Sheet(s) Filed in Color)

(56) References Cited

U.S. PATENT DOCUMENTS

| | | | | |
|---|---|---|---|---|
| 2007/0142713 | A1* | 6/2007 | Lancaster | G06Q 50/22 600/300 |
| 2009/0138318 | A1* | 5/2009 | Hawkins | G16H 40/20 705/7.27 |
| 2009/0254362 | A1* | 10/2009 | Choubey | G16H 40/20 705/2 |
| 2011/0077972 | A1* | 3/2011 | Breitenstein | G06Q 10/10 705/3 |
| 2012/0130730 | A1* | 5/2012 | Setlur | G16H 40/20 705/2 |
| 2014/0108034 | A1* | 4/2014 | Akbay | G06Q 10/06315 705/2 |
| 2014/0136458 | A1* | 5/2014 | Levin | G16H 50/20 706/21 |
| 2015/0213222 | A1* | 7/2015 | Amarasingham | G16H 50/30 705/2 |
| 2016/0253461 | A1* | 9/2016 | Sohr | G16H 50/30 705/3 |
| 2016/0358116 | A1* | 12/2016 | Cline | G06Q 10/063114 |
| 2016/0371441 | A1* | 12/2016 | Day | G16Z 99/00 |
| 2018/0286500 | A1* | 10/2018 | Sole Guerra | G06Q 50/22 |
| 2019/0180868 | A1* | 6/2019 | Makram | G06Q 10/0631 |
| 2019/0304595 | A1* | 10/2019 | Bergman | G16H 40/20 |

* cited by examiner

FIG. 9

| Metric | Condition | Points |
|---|---|---|
| Vitals Missing? | LOS > 30m | 100 |
| Vitals Missing? | LOS 20-30m | 75 |
| Vitals Missing? | LOS 10-19m | 20 |
| Vitals Critical? | | 75 |
| Dispo = Discharge | TSD > 120m | 50 |
| Dispo = Discharge | TSD 90-120m | 25 |
| Dispo = Discharge | TSD 60-89m | 20 |
| Dispo = Discharge | TSD 30-59m | 1 |
| Dispo = Admit | TSD > 600m | 5 |
| Dispo = Admit | TSD 500-599m | 4 |
| Dispo = Admit | TSD 400-499m | 3 |
| Dispo = Admit | TSD 300-399m | 2 |
| EKG Pending | Pending > 60m | 5 |
| EKG Pending | Pending 45-60m | 4 |
| EKG Pending | Pending 30-49 | 3 |
| EKG Pending | Pending 10-29 | 2 |
| High risk infusion | Each | 30 |
| Press Ganey Survey | | 5 |
| Restraints | with CO | 10 |
| Restraints | without CO | 100 |
| CO | without restraints | 25 |
| Critical Labs | Each | 10 |
| Fall Risk | | 5 |
| Isolation | | 5 |
| Dispo = Admit | Ready Bed > 60m | 25 |
| Dispo = Admit | Ready Bed 30-59m | 10 |

| IV/IM/SQ Medication Administration | | | | Oral Medication Administration | | | |
|---|---|---|---|---|---|---|---|
| 113 min | (x 2) | BLUHALL | DOE, JOHN | 91 min | (x 5) | PNK42 | DOE, JOHN |
| 91 min | (x 1) | PNK42 | DOE, JOHN | 58 min | (x 6) | HLD-D | DOE, JOHN |
| 65 min | (x 1) | GOLDHALL | DOE, JOHN | 46 min | (x 4) | PRP20 | DOE, JOHN |
| 55 min | (x 1) | PRPHALL | DOE, JOHN | ceftRIAXone IVPB | | | DOE, JOHN |
| 54 min | (x 2) | REDHALL | DOE, JOHN | | | | DOE, JOHN |
| 53 min | (x 2) | HLD-D | DOE, JOHN | 21 min | (x 8) | PRPHALL | DOE, JOHN |
| 46 min | (x 1) | PRP20 | DOE, JOHN | 19 min | (x 1) | GRNHALL | DOE, JOHN |
| 44 min | (x 1) | GRN-C | DOE, JOHN | 8 min | (x 5) | REDHALL | DOE, JOHN |
| | | REDHALL | DOE, JOHN | | | | |
| 20 min | (x 1) | PRPHALL | DOE, JOHN | | | | |
| 12 min | (x 1) | HLD27-S | DOE, JOHN | | | | |
| 8 min | (x 1) | REDHALL | DOE, JOHN | | | | |

Complete Survey (93/Male)
HH, Service Inpatient, visit 4/5/2018

| Question | Answer |
|---|---|
| Before giving you any new medicine, how often did hospital staff describe possible side effects in a way you could understand? | Sometimes |
| Before giving you any new medicine, how often did hospital staff tell you what the medicine was for? | Always |
| Courtesy of the person who took your personal/insurance information | 5 |
| Degree to which the doctor in charge of your care was identified | |
| During this hospital stay, after you pressed the call button, how often did you get help as soon as you wanted it? | Usually |
| During this hospital stay, how often did doctors explain things in a way you could understand? | Never |
| During this hospital stay, how often did doctors listen carefully to you? | Never |
| During this hospital stay, how often did doctors treat you with courtesy and respect? | Sometimes |
| During this hospital stay, how often did nurses explain things in a way you could understand? | Usually |
| During this hospital stay, how often did nurses listen carefully to you? | Always |
| During this hospital stay, how often did nurses treat you with courtesy and respect? | Always |
| During this hospital stay, how often was the area around your room quiet at night? | Sometimes |
| During this hospital stay, how often were your room and bathroom kept clean? | Always |
| During this hospital stay, staff took my preferences and those of my family or caregiver into account in deciding what my health care needs would be when I left. | Agree |
| During your hospital stay, did hospital staff talk with you about whether you would have the help you needed when you left the hospital? (y/n) | yes |
| During your hospital stay, did you get information in writing about what symptoms or health problems to look out for after you left the hospital? (y/n) | yes |
| How likely is it that you would recommend Northwell Health to a friend or family? | 5 |
| How well staff worked together to care for you | 5 |
| How well the staff respected cultural, racial and religious needs | 5 |
| Overall rating of the Emergency Room care and treatment | 4 |
| Quality of the food | 4 |
| Speed of admission process | 5 |
| Staff effort to include you in decisions about your treatment | ? |
| Using any number from 0 to 10, where 0 is the worst hospital possible and 10 is the best hospital possible, what number would you use to rate this hospital? | Strongly agree |
| When I left the hospital, I clearly understood the purpose for taking each of my medications. | Agree |
| When I left the hospital, I had a good understanding of the things I was responsible for in managing my health. | Probably yes |
| Would you recommend this hospital to your friends and family? | |

Comments (93/Male)
Better food.

FIG. 18

| Current Holds by Department | | | | | | |
|---|---|---|---|---|---|---|
| Department | Admits | >2h | >6h | >12h | >24h | >48h |
| Department 1 | 5 | 3 | 3 | 1 | | |
| Department 2 | 22 | 18 | 16 | 10 | 3 | 1 |
| Department 3 | 1 | | | | | |
| Department 4 | 3 | 3 | | | | |
| Department 5 | 8 | 6 | 6 | 4 | | |
| Department 6 | | | | | | |
| Department 7 | 25 | 21 | 19 | 16 | 2 | 1 |
| Department 8 | 46 | 35 | 30 | 19 | | |
| Department 9 | 4 | 2 | | | | |
| Department 10 | 1 | | | | | |
| Department 11 | 54 | 49 | 48 | 47 | 20 | 7 |
| Department 12 | 35 | 27 | 24 | 22 | 3 | 1 |
| Department 13 | 1 | 1 | 1 | | | |
| Department 14 | 3 | 2 | 2 | | | |
| | 208 | 167 | 149 | 119 | 28 | 10 |

EDs nationwide are overcrowded and over capacity.

1. Sick people have to wait too long to receive care
- According to the CDC, 10% of patients identified to be critical by the triage nurse waited more than an hour to see a physician
- Only 67% of acutely ill patients were seen within the recommended times in the US (Annals of Emergency Med)

2. Boarding increases total length of stay (LOS) in the hospital
- Total hospital LOS has been reported to be a full day longer in patients boarded in the ED versus patients with similar illnesses placed on an inpatient unit (American Journal of Emergency Medicine)

3. Boarding increases walkouts and LWOBEs
- Patients are more likely to leave the hospital without receiving the appropriate care as the wait time increases (Academic Emergency Medicine)

4. Overcrowding decreases quality of care and increases medical errors
- Errors of omission
- Boarded admissions are at a higher risk of an adverse event or error (American Journal Emergency Medicine)

5. Overcrowding increases mortality
- Mortality rate was 2.5% for those boarded for less than 2 hours and increased to 4.5% for those boarding for greater than 12 hours
- Similarly LOS increased from 5.6 days to 8.7 days (Medical Journal of Australia)

6. Overcrowding causes ambulance diversion
- According to the CDC, approximately 50% of EDs experience overcrowding, and 33% of US hospitals have experienced ambulance diversion (Annals of Emergency Medicine)

FIG. 43

| QUALITY | VOLUME | THROUGHPUT | FINANCE | PATIENT SATISFACTION | EMPLOYEE ENGAGEMENT |
|---|---|---|---|---|---|
| • Pneumonia<br>• Sepsis – Lactates<br>• Sepsis – Abx<br>• Cardiac Care – Balloon & EKG<br>• Cath – Door to EKG, Door to PCI<br>• Pediatrics<br>• Restraint<br>• Sedation<br>• Hand-washing<br>• Pain Control – Documentation & Timeliness<br>• Vital Signs<br>• Transfers<br>• Capnography<br>• Care of Sexual Assault Survivors<br>• Abuse Screen<br>• Med Errors<br>• Adverse Drug Reactions<br>• Falls<br>• Stroke Code | • Total Registered<br>• Total Admissions<br>• Treat & Release<br>• Pediatric Treat & Release<br>• Pediatric Admits<br>• Pediatric Transfers<br>• Unplanned Returns<br>• CDU admits & Treat & Release | • Door to Bed<br>• Door to RN<br>• Door to Provider<br>• Provider to Disposition<br>• Decision to Admit to Bed Assignment<br>• Bed Assignment to ED Departure<br>• Total ALOS<br>• ALOS Treat & Release<br>• ALOS Admitted Patients<br>• ALOS Transfers<br>• ALOS Pediatric<br>• ALOS Psych<br>• ALOS EKHO<br>• ALOS CDU<br>• ALOS Class 1 OR<br>• ED Midnight Census<br>• Ambulance – Volume<br>• Ambulance – TAT<br>• LWBS<br>• Diversion<br>• ED Registration<br>• Mortality within 24hrs | • PQRI<br>• IV Start and Stop<br>• P&L<br>• E&M<br>• Distribution Tech & Pro<br>• Charges<br>• Utilization by physician<br>• Revenue<br>• Billed vs. Budget<br>• Pro Charges<br>• Avg Charge<br>• Avg Payment<br>• Gross Collection Rate<br>• Trending/Variance Analysis<br>• KPI Monitoring | • Overall Satisfaction<br>• Likelihood to Recommend<br>• How well was your pain controlled<br>• Physician and Nursing Section Scoring<br>• Top Box scores | • Annual employee engagement surveys<br>• Ten Leaders<br>• Turnover and stability |

Over 200 metrics are captured by the EMSL sites. This slide highlights a portion of those metrics.

FIG. 45

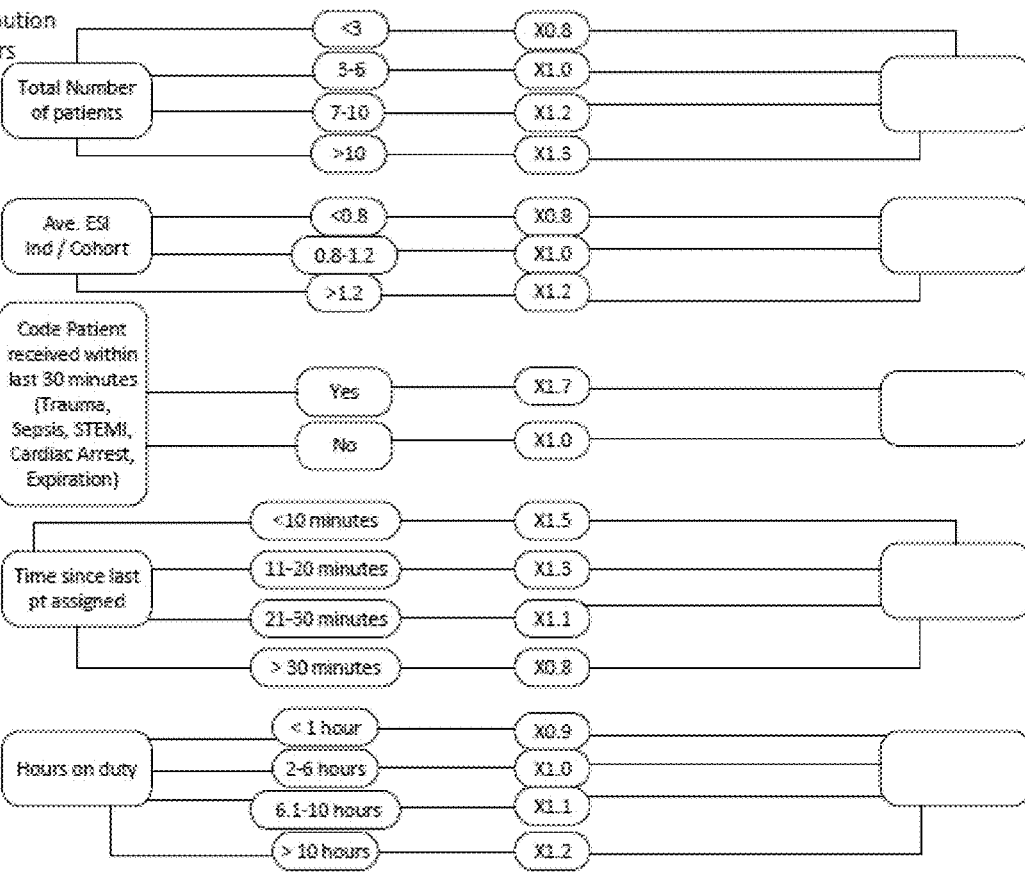
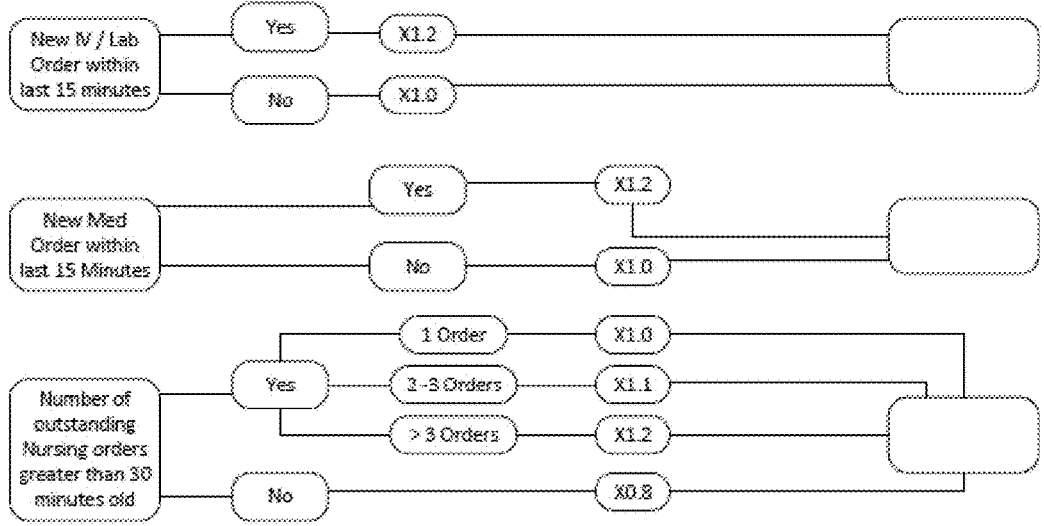
FIG. 50

US 11,257,587 B1

COMPUTER-BASED SYSTEMS, IMPROVED COMPUTING COMPONENTS AND/OR IMPROVED COMPUTING OBJECTS CONFIGURED FOR REAL TIME ACTIONABLE DATA TRANSFORMATIONS TO ADMINISTER HEALTHCARE FACILITIES AND METHODS OF USE THEREOF

CROSS-REFERENCE TO RELATED APPLICATIONS

This application claims priority to U.S. Provisional Application No. 62/848,765 filed on 16 May 2019 and entitled "IMPROVED COMPUTER-BASED SYSTEMS, IMPROVED COMPUTING COMPONENTS AND/OR IMPROVED COMPUTING OBJECTS CONFIGURED FOR REAL TIME ACTIONABLE DATA TRANSFORMATIONS TO ADMINISTER HEALTHCARE FACILITIES AND METHODS OF USE THEREOF," and is herein incorporated by reference in its entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in drawings that form a part of this document: Copyright, Northwell Health, Inc., All Rights Reserved.

FIELD OF TECHNOLOGY

The present disclosure generally relates to improved computer-based platforms or systems, improved computing devices and components and/or improved computing objects configured for one or more novel technological applications of source-agnostic real-time analysis and prioritization of data for direct decision making through the collection, aggregation, normalization and processing of raw data sourced from diverse vendor specific databases.

BACKGROUND OF TECHNOLOGY

A computer network platform/system may include a group of computers (e.g., clients, servers, smart routers (e.g., trading smart routers)) and other computing hardware devices that are linked together through one or more communication channels to facilitate communication and/or resource-sharing, via one or more specifically programmed graphical user interfaces (GUIs) of the present disclosure, among a wide range of users.

Personnel and resource management relies on knowledge of personnel and resource usage. Generally, personnel and resources are deployed according to raw observations collected from often proprietary sources. Thus, the representation of a current resource usage and resource need is subject to compatibility with the proprietary source of data. Further, the representation is often presented in a difficult to access and understand.

SUMMARY OF DESCRIBED SUBJECT MATTER

In some embodiments, the present disclosure provides various exemplary technically improved computer-implemented systems, e.g., a system including features such as:
 a database layer that is at least configured to:
  i) query patient-related raw data from a plurality of data tables of a plurality of distinct data collection services having the plurality of distinct service specific data formats, wherein the patient-related raw data is related to a plurality of patients being serviced at a healthcare facility,
  ii) normalize the patient-related raw data with respect to the plurality of distinct service specific data formats to produce common format normalized patient-related data, and
  iii) store the common format normalized patient-related data;
 an algorithmic processing layer that is at least configured to:
  i) analyze, in real-time, the common format normalized patient-related data for the plurality of patients based on a plurality of patient-related data metrics, a plurality of healthcare facility-related data metrics, or both, to determine a plurality of patient-related data points for the plurality of patients, wherein each patient-related data point is associated with a respective threshold condition and a respective ranking score;
  ii) rank, in real-time, for the plurality of patients, the plurality of patient-related data points, based on each respective threshold condition and each respective ranking score to determine a priority of each patient-related data point; and
  iii) generate, in real-time, based on the priority of each patient-related data point of the patient-related data points, at least one actionable medical directive related to at least one patient of the plurality of patients, wherein the at least one actionable medical directive is configured to cause at least one real-time operational change in the way that the healthcare facility services the at least one patient of the plurality of patients; and
 a visualization layer that is at least configured to cause presenting, in real-time, on a mobile computing device, the at least one actionable medical directive related to the at least one patient of the plurality of patients.

In some embodiments, the present disclosure provides various exemplary technically improved computer-implemented methods, e.g., a method including features such as:
 obtaining, by one or more processors, patient-related raw data from a plurality of data tables of a plurality of distinct data collection services having the plurality of distinct service specific data formats, wherein the patient-related raw data relates to a plurality of patients being serviced at a healthcare facility;
 normalizing, by the one or more processors, the patient-related raw data with respect to the plurality of distinct service specific data formats to produce common format normalized patient-related data;
 storing, by the one or more processors, the common format normalized patient-related data in at least one database;
 analyzing, in real-time, by the one or more processors, the common format normalized patient-related data for the plurality of patients based on a plurality of patient-related data metrics, a plurality of healthcare facility-related data metrics, or both, to determine a plurality of patient-related data points for the plurality of patients, wherein each patient-related data point is associated with a respective threshold condition and a respective ranking score;

ranking, in real-time, by the one or more processors, for the plurality of patients, the plurality of patient-related data points, based on each respective threshold condition and each respective ranking score to determine a priority of each patient-related data point for each patient;

generating, in real-time, by the one or more processors, based on the priority of each patient-related data point of the patient-related data points, at least one actionable medical directive related to at least one patient of the plurality of patients, wherein the at least one actionable medical directive is configured to cause at least one real-time operational change in the way that the healthcare facility services the at least one patient of the plurality of patients; and causing to present, in real-time, by the one or more processors, on a computing device, the at least one actionable medical directive related to the at least one patient of the plurality of patients.

In some embodiments, the present disclosure provides various exemplary technically improved computer-implemented methods, e.g., a method including features such as:

determining, by one or more processors, a selection of at least one patient of a plurality of patients with a hospital tracking interface of a mobile computing device associated with a user;

where the hospital tracking interface includes a graphical user interface (GUI) that allows a user to view and select information related to the plurality of patients being serviced at the healthcare facility;

communicating, by the one or more processors, the selection to one or more real-time actionable database (RAD) processors, where the one or more RAD processors are configured to:

obtain patient-related raw data from a plurality of data tables of a plurality of distinct data collection services having the plurality of distinct service specific data formats, where the patient-related raw data is related to the plurality of patients being serviced at the healthcare facility;

normalize the patient-related raw data with respect to the plurality of distinct service specific data formats to produce common format normalized patient-related data;

store the common format normalized patient-related data in at least one database;

analyze, in real-time, the common format normalized patient-related data for the plurality of patients based on a plurality of patient-related data metrics, a plurality of healthcare facility-related data metrics, or both, to determine a plurality of patient-related data points for the plurality of patients, where each patient-related data point is associated with a respective threshold condition and a respective ranking score;

rank, in real-time for the plurality of patients, the plurality of patient-related data points, based on each respective threshold condition and each respective ranking score to determine a priority of each patient-related data point;

generate, in real-time, based on the priority of each patient-related data point of the patient-related data points, at least one actionable medical directive related to the at least one patient of the plurality of patients, where the at least one actionable medical directive is configured to cause at least one real-time operational change in the way that the healthcare facility services the at least one patient of the plurality of patients;

transmit, in real-time, the at least one actionable medical directive to the mobile computing device; and causing to present, in real-time, by the one or more processors, on the mobile computing device associated with the user, the at least one actionable medical directive related to the at least one patient of the plurality of patients.

In some embodiments, the present disclosure provides various exemplary technically improved computer-implemented methods, e.g., a method including features such as:

determining, by one or more processors, a selection of at least one patient of a plurality of patients with a hospital tracking interface of a computing device associated with a user;

wherein the hospital tracking interface comprises a graphical user interface (GUI) that allows a user to view and select information related to the plurality of patients being serviced at the healthcare facility;

communicating, by the one or more processors, the selection to one or more real-time actionable database (RAD) processors, wherein the one or more RAD processors are configured to:

obtain patient-related raw data from a plurality of data tables of a plurality of distinct data collection services having the plurality of distinct service specific data formats, wherein the patient-related raw data relates to the plurality of patients being serviced at the healthcare facility;

normalize the patient-related raw data with respect to the plurality of distinct service specific data formats to produce common format normalized patient-related data;

store the common format normalized patient-related data in at least one database;

analyze, in real-time, the common format normalized patient-related data for the plurality of patients based on a plurality of patient-related data metrics, a plurality of healthcare facility-related data metrics, or both, to determine a plurality of patient-related data points for the plurality of patients, wherein each patient-related data point is associated with a respective threshold condition and a respective ranking score;

rank, in real-time for the plurality of patients, the plurality of patient-related data points, based on each respective threshold condition and each respective ranking score to determine a priority of each patient-related data point for each patient;

generate, in real-time, based on the priority of each patient-related data point of the patient-related data points, at least one actionable medical directive related to the at least one patient of the plurality of patients, wherein the at least one actionable medical directive is configured to cause at least one real-time operational change in the way that the healthcare facility services the at least one patient of the plurality of patients;

transmit, in real-time, the at least one actionable medical directive to the mobile computing device; and causing to present, in real-time, by the one or more processors, on the computing device associated with the user, the at least one actionable medical directive related to the at least one patient of the plurality of patients.

In some embodiments, a method and/or system described herein relates to at least one actionable medical directive comprising a matching of a plurality of resources across two or more patients, three or more patients, four or more patients, five or more patients, six or more patients, seven or more patients, eight or more patients, nine or more patients, ten or more patients, eleven or more patients, twelve or more patients, thirteen or more patients, fourteen or more patients, or fifteen or more of the plurality of patients according to a respective utilization capacity of each resource of the plurality of resources.

In some embodiments, aspects involving use of database interoperability, data analysis, visualization tools and networking. Various such technical solutions herein may also enable the collection, management, analysis and visualization of real-time actionable data for workforce and service management with compatibility across distinct database vendors.

In some embodiments, the present disclosure also provides exemplary technically improved, computer-implemented methods and computer-readable media, including media embodied an application ("App"), whether resident on a device or provided for download via a server, that include or involves features, functionality, components and/or steps consistent with those recited above.

BRIEF DESCRIPTION OF THE DRAWINGS

The patent or application file contains at least one drawing executed in color Copies of this patent or patent application publication with color drawing(s) will be provided by the Office upon request and payment of the necessary fee.

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art to variously employ one or more illustrative embodiments.

FIGS. 1-51 show one or more schematic flow diagrams, certain computer-based architectures, and/or screenshots of various specialized graphical user interfaces which are illustrative of some exemplary aspects of at least some embodiments of the present disclosure.

DETAILED DESCRIPTION

Figure 1:
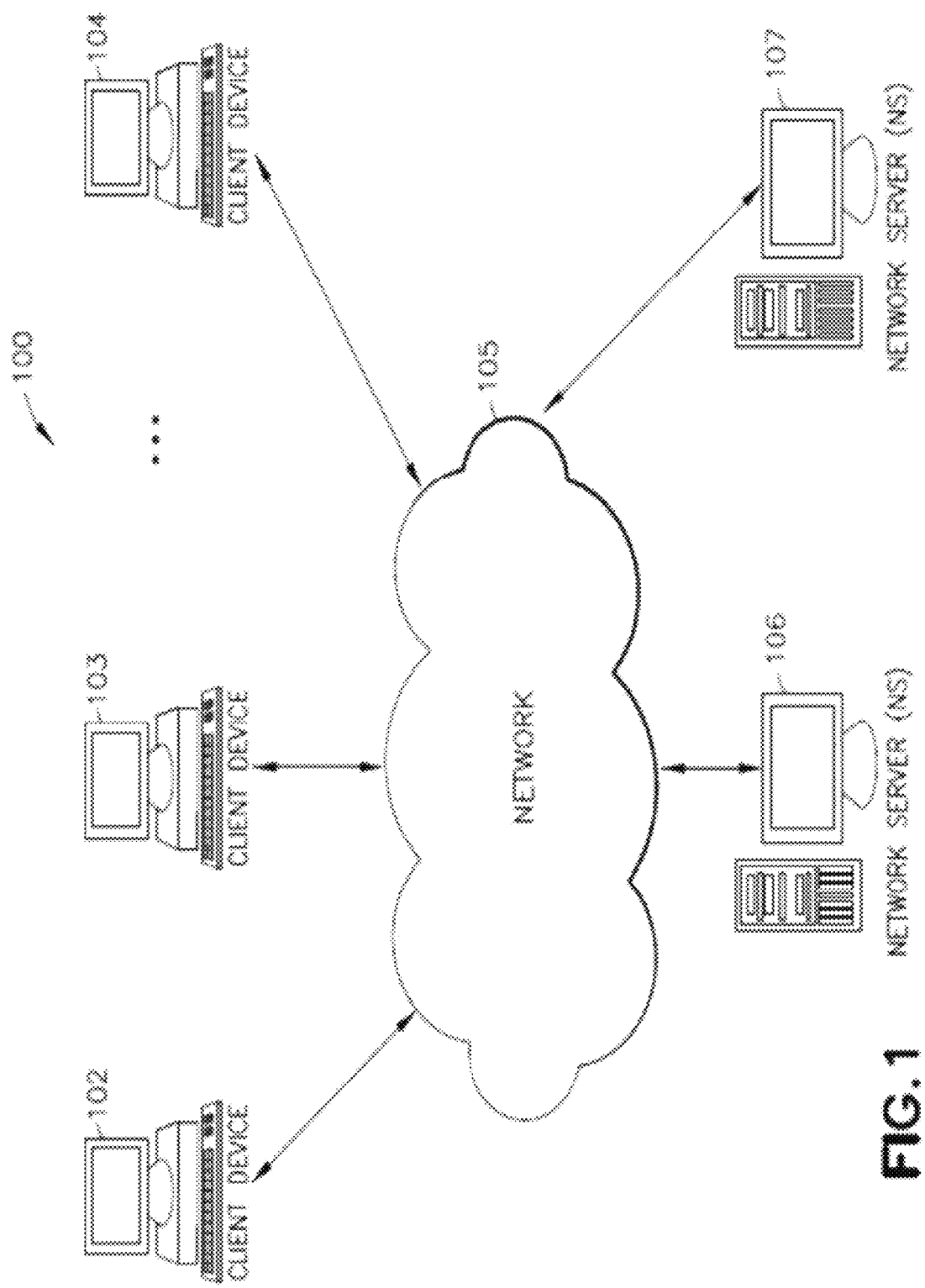

Various detailed embodiments of the present disclosure, taken in conjunction with the accompanying figures, are disclosed herein; however, it is to be understood that the disclosed embodiments are merely illustrative. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time analysis," "real-time computation," and "real-time execution" all pertain to the performance of a computation during the actual time that the related data collection and/or physical process (e.g., a user interacting with an application on a mobile device) occurs, in order that results of the computation can be used in guiding the physical process.

As used herein, the term "normalize" and its logical and/or linguistic relatives and/or derivatives, refers to a process of structuring data in a database according to a format for associated data, e.g., data tables, tuples, and/or arrays, that is common for each entry of data. In some embodiments, data in a database can be normalized to, e.g., remove redundant information, facilitate comparison of data fields between different data entries, reduce data anomalies, and facilitate uniform storage, processing and retrieval of data entries, among other uses.

As used herein, the term "common format normalized patient-related data" refers to patient-related data that has been collected, e.g., in a database and normalized to have a common format, as described above with respect to the term "normalize."

As used herein, the term "dynamically" and term "automatically," and their logical and/or linguistic relatives and/or derivatives, mean that certain events and/or actions can be triggered and/or occur without any human intervention. In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

As used herein, the term "runtime" corresponds to any behavior that is dynamically determined during an execution of a software application or at least a portion of software application.

In some embodiments, exemplary inventive, specially programmed computing systems/platforms with associated devices are configured to operate in the distributed network environment, communicating with one another over one or more suitable data communication networks (e.g., the Internet, satellite, etc.) and utilizing one or more suitable data communication protocols/modes such as, without limitation, IPX/SPX, X.25, AX.25, AppleTalk™, TCP/IP (e.g., HTTP), near-field wireless communication (NFC), RFID, Narrow Band Internet of Things (NBIOT), 3G, 4G, 5G, GSM, GPRS, WiFi, WiMax, CDMA, satellite, ZigBee, and other suitable communication modes. In some embodiments, the NFC can represent a short-range wireless communications technology in which NFC-enabled devices are "swiped," "bumped," "tap" or otherwise moved in close proximity to communicate. In some embodiments, the NFC could include a set of short-range wireless technologies, typically requiring a distance of 10 cm or less. In some embodiments, the NFC may operate at 13.56 MHz on ISO/IEC 18000-3 air interface and at rates ranging from 106 kbit/s to 424 kbit/s. In some embodiments, the NFC can involve an initiator and a target; the initiator actively generates an RF field that can power a passive target. In some embodiment, this can enable NFC targets to take very simple form factors such as tags, stickers, key fobs, or cards that do not require batteries. In some embodiments, the NFC's peer-to-peer communication can be conducted when a plurality of NFC-enable devices (e.g., smartphones) within close proximity of each other.

The material disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

As used herein, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, etc.).

In some embodiments, one or more of exemplary inventive computer-based systems/platforms, exemplary inventive computer-based devices, and/or exemplary inventive computer-based components of the present disclosure may include or be incorporated, partially or entirely into at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

As used herein, term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

In some embodiments, as detailed herein, one or more of exemplary inventive computer-based systems/platforms, exemplary inventive computer-based devices, and/or exemplary inventive computer-based components of the present disclosure may obtain, manipulate, transfer, store, transform, generate, and/or output any digital object and/or data unit (e.g., from inside and/or outside of a particular application) that can be in any suitable form such as, without limitation, a file, a contact, a task, an email, a tweet, a map, an entire application (e.g., a calculator), etc. In some embodiments, as detailed herein, one or more of exemplary inventive computer-based systems/platforms, exemplary inventive computer-based devices, and/or exemplary inventive computer-based components of the present disclosure may be implemented across one or more of various computer platforms such as, but not limited to: (1) AmigaOS, AmigaOS 4; (2) FreeBSD, NetBSD, OpenBSD; (3) Linux; (4) Microsoft Windows; (5) OpenVMS; (6) OS X (Mac OS); (7) OS/2; (8) Solaris; (9) Tru64 UNIX; (10) VM; (11) Android; (12) Bada; (13) BlackBerry OS; (14) Firefox OS; (15) Ios; (16) Embedded Linux; (17) Palm OS; (18) Symbian; (19) Tizen; (20) WebOS; (21) Windows Mobile; (22) Windows Phone; (23) Adobe AIR; (24) Adobe Flash; (25) Adobe Shockwave; (26) Binary Runtime Environment for Wireless (BREW); (27) Cocoa (API); (28) Cocoa Touch; (29) Java Platforms; (30) JavaFX; (31) JavaFX Mobile; (32) Microsoft XNA; (33) Mono; (34) Mozilla Prism, XUL and XULRunner; (35) .NET Framework; (36) Silverlight; (37) Open Web Platform; (38) Oracle Database; (39) Qt; (40) SAP NetWeaver; (41) Smartface; (42) Vexi; and/OR (43) Windows Runtime.

In some embodiments, exemplary inventive computer-based systems/platforms, exemplary inventive computer-based devices, and/or exemplary inventive computer-based components of the present disclosure may be configured to utilize hardwired circuitry that may be used in place of or in combination with software instructions to implement features consistent with principles of the disclosure. Thus, implementations consistent with principles of the disclosure are not limited to any specific combination of hardware circuitry and software. For example, various embodiments may be embodied in many different ways as a software component such as, without limitation, a stand-alone software package, a combination of software packages, or it may be a software package incorporated as a "tool" in a larger software product.

For example, exemplary software specifically programmed in accordance with one or more principles of the present disclosure may be downloadable from a network, for example, a website, as a stand-alone product or as an add-in package for installation in an existing software application. For example, exemplary software specifically programmed in accordance with one or more principles of the present disclosure may also be available as a client-server software application, or as a web-enabled software application. For example, exemplary software specifically programmed in accordance with one or more principles of the present disclosure may also be embodied as a software package installed on a hardware device.

In some embodiments, exemplary inventive computer-based systems/platforms, exemplary inventive computer-based devices, and/or exemplary inventive computer-based components of the present disclosure may be configured to handle numerous concurrent users (e.g., medical practitioners and staff) that may be, but is not limited to, at least 5 (e.g., but not limited to, 5-10), at least 10 (e.g., but not limited to, 10-20), at least 15 (e.g., but not limited to, 15-25), at least 20 (e.g., but not limited to, 20-30), at least 25 (e.g., but not limited to, 25-35), at least 50 (e.g., but not limited to, 50-74), at least 75 (e.g., but not limited to, 75-99), 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-10,000,000,000).

In some embodiments, exemplary inventive computer-based systems/platforms, exemplary inventive computer-based devices, and/or exemplary inventive computer-based components of the present disclosure may be configured to handle numerous concurrent patients at various stages of care (e.g., at initial presentation, at intake, admitted, at release, during outpatient procedures), in diverse locations within the healthcare system, in different locations within a healthcare facility that may be, but is not limited to, at least 5 (e.g., but not limited to, 5-10), at least 10 (e.g., but not limited to, 10-20), at least 15 (e.g., but not limited to, 15-25), at least 20 (e.g., but not limited to, 20-30), at least 25 (e.g., but not limited to, 25-35), at least 50 (e.g., but not limited to, 50-74), at least 75 (e.g., but not limited to, 75-99), 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-10,000,000,000). The numerous concurrent patients may, for example, be 5-1,000; 5-500; 5-250; 5-100; 5-50; or 5-25.

In some embodiments, exemplary inventive computer-based systems/platforms, exemplary inventive computer-based devices, and/or exemplary inventive computer-based components of the present disclosure may be configured to output to distinct, specifically programmed graphical user interface implementations of the present disclosure (e.g., a desktop, a web app., etc.). In various implementations of the present disclosure, a final output may be displayed on a displaying screen which may be, without limitation, a screen of a computer, a screen of a mobile device, or the like. In various implementations, the display may be a holographic display. In various implementations, the display may be a transparent surface that may receive a visual projection. Such projections may convey various forms of information, images, and/or objects. For example, such projections may be a visual overlay for a mobile augmented reality (MAR) application.

In some embodiments, exemplary inventive computer-based systems/platforms, exemplary inventive computer-based devices, and/or exemplary inventive computer-based components of the present disclosure may be configured to be utilized in various applications which may include, but not limited to, gaming, mobile-device games, video chats, video conferences, live video streaming, video streaming and/or augmented reality applications, mobile-device messenger applications, and others similarly suitable computer-device applications.

As used herein, the term "mobile electronic device," or the like, may refer to any portable electronic device that may or may not be enabled with location tracking functionality (e.g., MAC address, Internet Protocol (IP) address, or the like). For example, a mobile electronic device can include, but is not limited to, a mobile phone, Personal Digital Assistant (PDA), Blackberry™, Pager, Smartphone, or any other reasonable mobile electronic device.

As used herein, terms "proximity detection," "locating," "location data," "location information," and "location tracking" refer to any form of location tracking technology or locating method that can be used to provide a location of, for example, a particular computing device/system/platform of the present disclosure and/or any associated computing devices, based at least in part on one or more of the following techniques/devices, without limitation: accelerometer(s), gyroscope(s), Global Positioning Systems (GPS); GPS accessed using Bluetooth™; GPS accessed using any reasonable form of wireless and/or non-wireless communication; WiFi™ server location data; Bluetooth™ based location data; triangulation such as, but not limited to, network based triangulation, WiFi™ server information based triangulation, Bluetooth™ server information based triangulation; Cell Identification based triangulation, Enhanced Cell Identification based triangulation, Uplink-Time difference of arrival (U-TDOA) based triangulation, Time of arrival (TOA) based triangulation, Angle of arrival (AOA) based triangulation; techniques and systems using a geographic coordinate system such as, but not limited to, longitudinal and latitudinal based, geodesic height based, Cartesian coordinates based; Radio Frequency Identification such as, but not limited to, Long range RFID, Short range RFID; using any form of RFID tag such as, but not limited to active RFID tags, passive RFID tags, battery assisted passive RFID tags; or any other reasonable way to determine location. For ease, at times the above variations are not listed or are only partially listed; this is in no way meant to be a limitation.

As used herein, terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user).

In some embodiments, the exemplary inventive computer-based systems/platforms, the exemplary inventive computer-based devices, and/or the exemplary inventive computer-based components of the present disclosure may be configured to securely store and/or transmit data by utilizing one or more of encryption techniques (e.g., private/public key pair, Triple Data Encryption Standard (3DES), block cipher algorithms (e.g., IDEA, RC2, RC5, CAST and Skipjack), cryptographic hash algorithms (e.g., MD5, RIPEMD-160, RTR0, SHA-1, SHA-2, Tiger (TTH), WHIRLPOOL, RNGs).

The aforementioned examples are, of course, illustrative and not restrictive.

As used herein, the term "user" shall have a meaning of at least one user. In some embodiments, the terms "user", "subscriber" "consumer" or "customer" should be understood to refer to a user of an application or applications as described herein and/or a consumer of data supplied by a data provider. By way of example, and not limitation, the terms "user" or "subscriber" can refer to a person who receives data provided by the data or service provider over the Internet in a browser session, or can refer to an automated software application which receives the data and stores or processes the data.

FIG. 1 depicts a block diagram of an exemplary computer-based system/platform 100 such as a real-time actionable data (RAD) system in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the exemplary inventive computing devices and/or the exemplary inventive computing components of the exemplary computer-based system/platform 100 may be configured to manage a large number of members and/or concurrent transactions, as detailed herein. In some embodiments, the exemplary computer-based system/platform 100 may be based on a scalable computer and/or network architecture that incorporates varies strategies for assessing the data, caching, searching, and/or database connection pooling. An example of the scalable architecture is an architecture that is capable of operating multiple servers.

In some embodiments, referring to FIG. 1, members 102-104 (e.g., clients) of the exemplary computer-based system/platform 100 may include virtually any computing device capable of receiving and sending a message over a network (e.g., cloud network), such as network 105, to and from another computing device, such as servers 106 and 107, each other, and the like. In some embodiments, the member devices 102-104 may be personal computers, multiprocessor systems, microprocessor-based or programmable consumer electronics, network PCs, and the like. In some embodiments, one or more member devices within member devices 102-104 may include computing devices that typically connect using a wireless communications medium such as cell phones, smart phones, pagers, walkie talkies, radio frequency (RF) devices, infrared (IR) devices, CBs, integrated devices combining one or more of the preceding devices, or virtually any mobile computing device, and the like. In some embodiments, one or more member devices within member devices 102-104 may be devices that are capable of connecting using a wired or wireless communication medium such as a PDA, POCKET PC, wearable computer, a laptop, tablet, desktop computer, a netbook, a video game device, a pager, a smart phone, an ultra-mobile personal computer (UMPC), and/or any other device that is equipped to communicate over a wired and/or wireless communication medium (e.g., NFC, RFID, NBIOT, 3G, 4G, 5G, GSM, GPRS, WiFi, WiMax, CDMA, satellite, ZigBee, etc.). In some embodiments, one or more member devices within member devices 102-104 may run one or more applications, such as Internet browsers, mobile applications, voice calls, video games, videoconferencing, and email, among others. In some embodiments, one or more member devices within member devices 102-104 may be configured to receive and to send web pages, and the like. In some embodiments, an exemplary specifically programmed browser application of the present disclosure may be configured to receive and display graphics, text, multimedia, and the like pertaining to RAD tools according to real-time data accessed across the network, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In some embodiments, a member device within member devices 102-104 may be specifically programmed by either Java, .Net, QT, C, C++ and/or other suitable programming language. In some embodiments, one or more member devices within member devices 102-104 may be specifically programmed include or execute an application to perform a variety of possible tasks, such as, without limitation, visualizing and uploading real-time data, including RAD, messaging functionality, browsing, searching, playing, streaming or displaying various forms of content, including locally stored or uploaded messages, images and/or video, and/or games.

In some embodiments, the exemplary network 105 may provide network access, data transport and/or other services to any computing device coupled to it, including between and amongst databases for collecting and storing real-time data uploaded from devices such as the member devices 102-104. In some embodiments, the exemplary network 105 may include and implement at least one specialized network architecture that may be based at least in part on one or more standards set by, for example, without limitation, Global System for Mobile communication (GSM) Association, the Internet Engineering Task Force (IETF), and the Worldwide Interoperability for Microwave Access (WiMAX) forum. In some embodiments, the exemplary network 105 may implement one or more of a GSM architecture, a General Packet Radio Service (GPRS) architecture, a Universal Mobile Telecommunications System (UMTS) architecture, and an evolution of UMTS referred to as Long Term Evolution (LTE). In some embodiments, the exemplary network 105 may include and implement, as an alternative or in conjunction with one or more of the above, a WiMAX architecture defined by the WiMAX forum. In some embodiments and, optionally, in combination of any embodiment described above or below, the exemplary network 105 may also include, for instance, at least one of a local area network (LAN), a wide area network (WAN), the Internet, a virtual LAN (VLAN), an enterprise LAN, a layer 3 virtual private network (VPN), an enterprise IP network, or any combination thereof. In some embodiments and, optionally, in combination of any embodiment described above or below, at least one computer network communication over the exemplary network 105 may be transmitted based at least in part on one of more communication modes such as but not limited to: NFC, RFID, Narrow Band Internet of Things (NBIOT), ZigBee, 3G, 4G, 5G, GSM, GPRS, WiFi, WiMax, CDMA, satellite and any combination thereof. In some embodiments, the exemplary network 105 may also include mass storage, such as network attached storage (NAS), a storage area network (SAN), a content delivery network (CDN) or other forms of computer or machine readable media.

In some embodiments, the exemplary server 106 or the exemplary server 107 may be a web server (or a series of servers) running a network operating system, examples of which may include but are not limited to Microsoft Windows Server, Novell NetWare, or Linux. In some embodiments, the exemplary server 106 or the exemplary server 107 may be used for and/or provide cloud and/or network computing to serve data collected in RAD databases. Alternatively, exemplary server 106 and exemplary server 107 can be implemented as RAD databases according to aspects of the present invention, or serve collected data to the RAD databases for storage. Although not shown in FIG. 1, in some embodiments, the exemplary server 106 or the exemplary server 107 may have connections to external systems like email, SMS messaging, text messaging, ad content providers, etc. Any of the features of the exemplary server 106 may be also implemented in the exemplary server 107 and vice versa.

In some embodiments, one or more of the exemplary servers 106 and 107 may be specifically programmed to perform, in non-limiting example, as authentication servers, search servers, email servers, social networking services servers, SMS servers, IM servers, MMS servers, exchange servers, photo-sharing services servers, advertisement providing servers, financial/banking-related services servers, travel services servers, or any similarly suitable service-base servers for users of the member computing devices 101-104.

In some embodiments and, optionally, in combination of any embodiment described above or below, for example, one or more exemplary computing member devices 102-104, the exemplary server 106, and/or the exemplary server 107 may include a specifically programmed software module that may be configured to send, process, and receive information using a scripting language, a remote procedure call, an email, a tweet, Short Message Service (SMS), Multimedia Message Service (MMS), instant messaging (IM), internet relay chat (IRC), mIRC, Jabber, an application programming interface, Simple Object Access Protocol (SOAP) methods, Common Object Request Broker Architecture (CORBA), HTTP (Hypertext Transfer Protocol), REST (Representational State Transfer), or any combination thereof.

Figure 2:
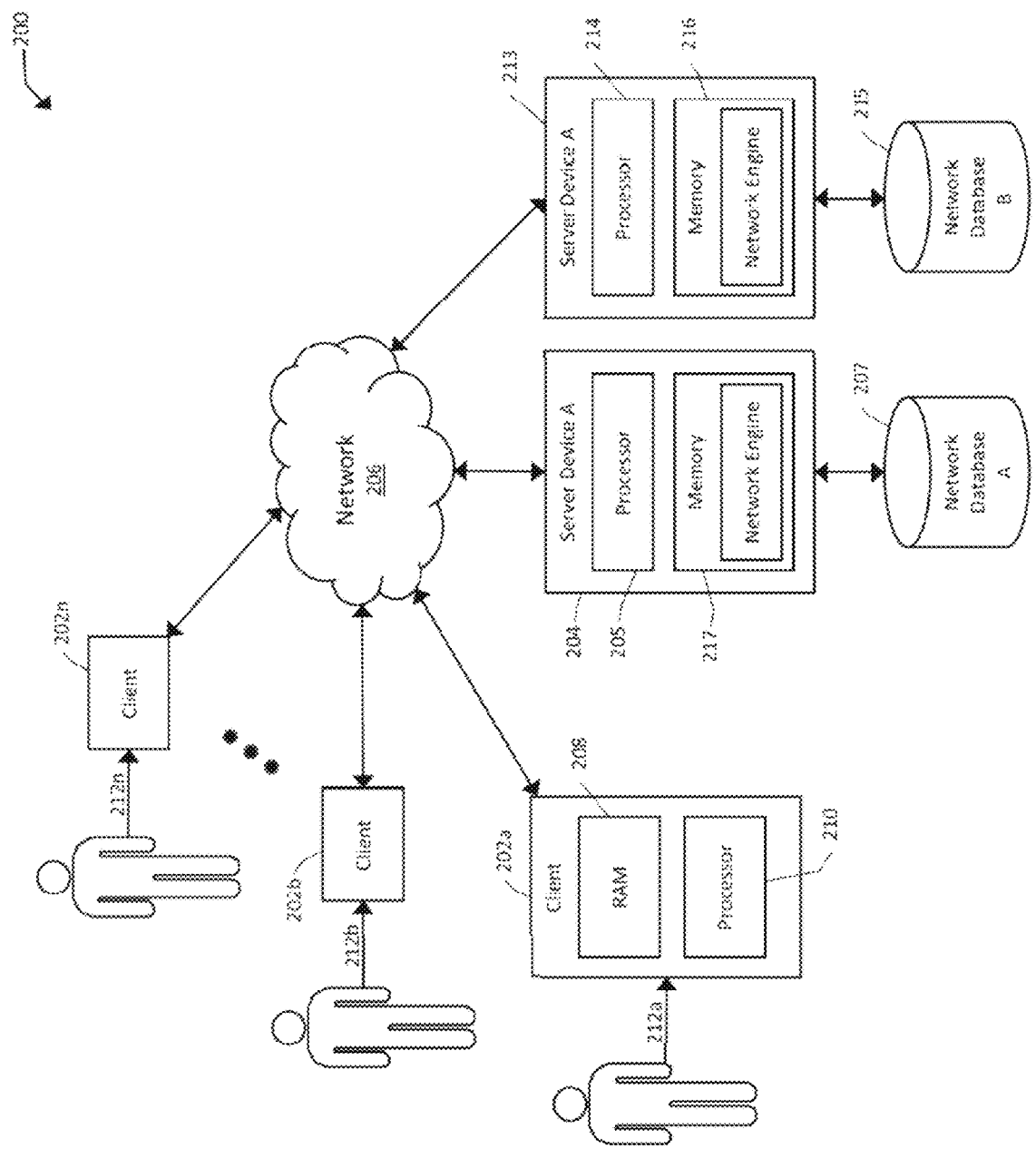

FIG. 2 depicts a block diagram of another exemplary computer-based system/platform 200 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the member computing devices 202*a*, 202*b* thru 202*n* shown each at least includes a computer-readable medium, such as a random-access memory (RAM) 208 coupled to a processor 210 or FLASH memory. In some embodiments, the processor 210 may execute computer-executable program instructions stored in memory 208. In some embodiments, the processor 210 may include a microprocessor, an ASIC, and/or a state machine. In some embodiments, the processor 210 may include, or may be in communication with, media, for example computer-readable media, which stores instructions that, when executed by the processor 210, may cause the processor 210 to perform one or more steps described herein, including steps pertaining to accessing and visualizing RAD database information, and uploading real-time data to the RAD databases. In some embodiments, examples of computer-readable media may include, but are not limited to, an electronic, optical, magnetic, or other storage or transmission device capable of providing a processor, such as the processor 210 of client 202*a*, with computer-readable instructions. In some embodiments, other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. In some embodiments, the instructions may comprise code from any computer-programming language, including, for example, C, C++, Visual Basic, Java, Python, Perl, JavaScript, and etc.

In some embodiments, member computing devices 202*a-n* may also comprise a number of external or internal devices such as a mouse, a CD-ROM, DVD, a physical or virtual keyboard, a display, or other input or output devices. In some embodiments, examples of member computing devices 202*a-n* (e.g., clients) may be any type of processor-based platforms that are connected to a network 206 such as, without limitation, personal computers, digital assistants, personal digital assistants, smart phones, pagers, digital tablets, laptop computers, Internet appliances, and other processor-based devices. In some embodiments, member computing devices 202*a-n* may be specifically programmed with one or more application programs in accordance with one or more principles/methodologies detailed herein for visualizing real-time actionable data and uploading real-time data to a database. In some embodiments, member computing devices 202*a-n* may operate on any operating system capable of supporting a browser or browser-enabled application, such as Microsoft™, Windows™, and/or Linux. In some embodiments, member computing devices 202*a-n* shown may include, for example, personal computers executing a browser application program such as Microsoft Corporation's Internet Explorer™, Apple Computer, Inc.'s Safari™, Mozilla Firefox, and/or Opera. In some embodiments, through the member computing client devices 202*a-n*, users, 212*a-n*, may communicate over the exemplary network 206 with each other and/or with other systems and/or devices coupled to the network 206. As shown in FIG. 2, exemplary server devices 204 and 213 may be also coupled to the network 206. In some embodiments, one or more member computing devices 202*a-n* may be mobile clients.

In some embodiments, at least one database of exemplary databases 207 and 2015 may be any type of database, including a database managed by a database management system (DBMS). In some embodiments, an exemplary DBMS-managed database may be specifically programmed as an engine that controls organization, storage, management, and/or retrieval of data in the respective database, including for the organization, storage, management, and/or retrieval of real-time data for generating real-time actionable data in a centralized, common format. In some embodiments, the exemplary DBMS-managed database may be specifically programmed to provide the ability to query, backup and replicate, enforce rules, provide security, compute, perform change and access logging, and/or automate matching. In some embodiments, the exemplary DBMS-managed database may be chosen from Oracle database, IBM DB2, Adaptive Server Enterprise, FileMaker, Microsoft Access, Microsoft SQL Server, MySQL, PostgreSQL, and a NoSQL implementation. In some embodiments, the exemplary DBMS-managed database may be specifically programmed to define each respective schema of each database in the exemplary DBMS, according to a particular database model of the present disclosure which may include a hierarchical model, network model, relational model, object model, or some other suitable organization that may result in one or more applicable data structures that may include fields, records, files, and/or objects. In some embodiments, the exemplary DBMS-managed database may be specifically programmed to include metadata about the data that is stored.

Figure 3:
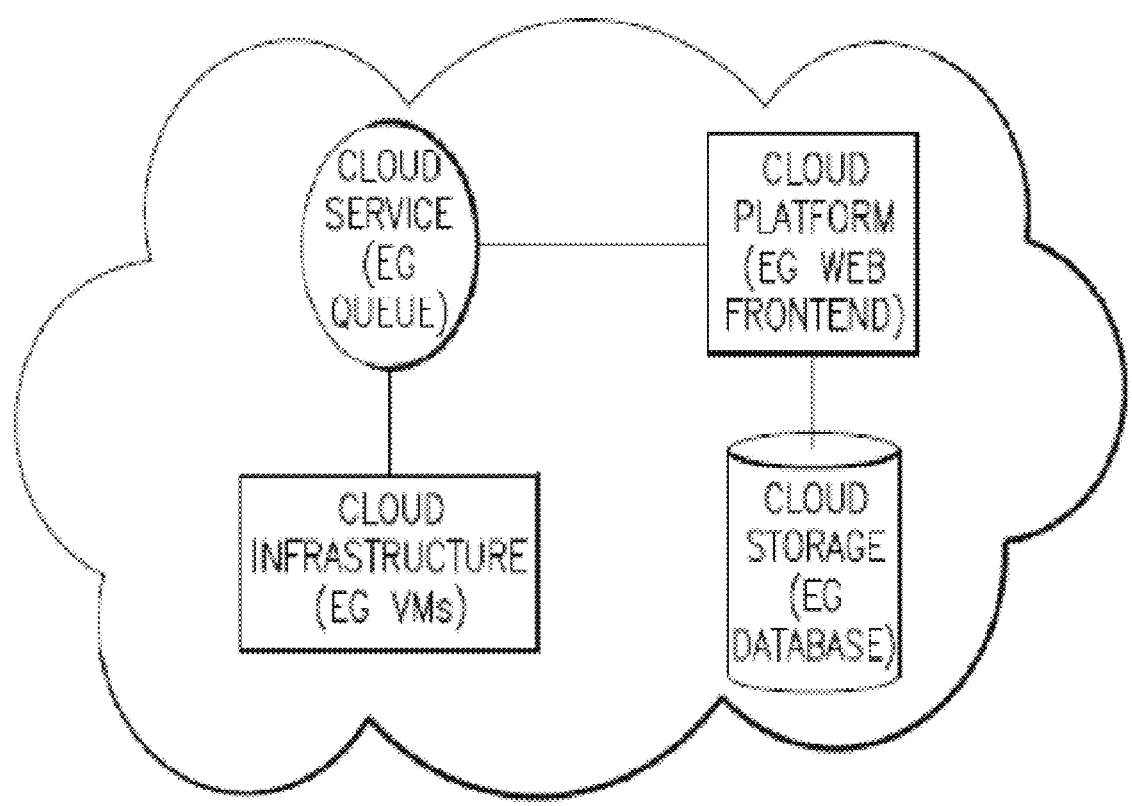
Figure 4:
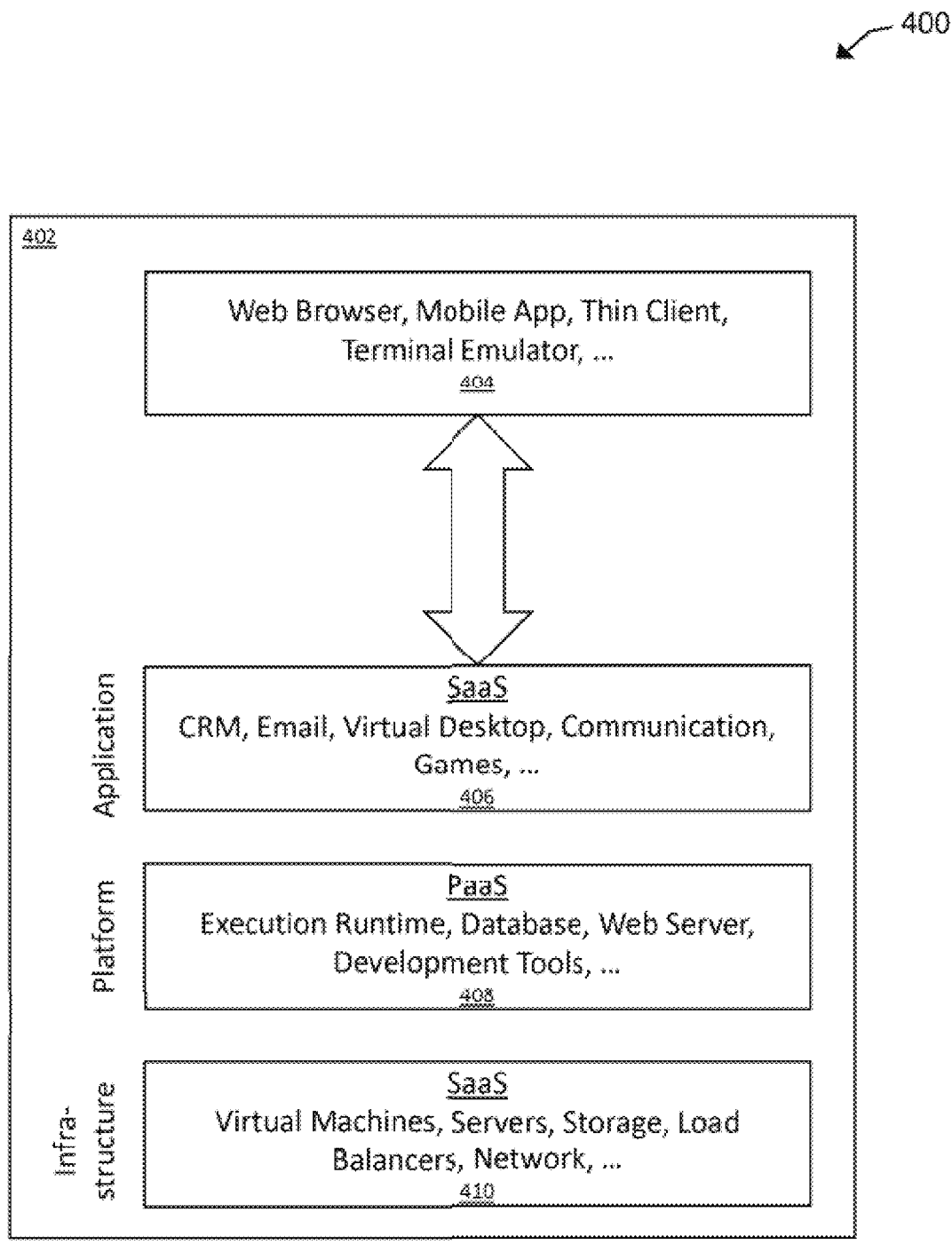

In some embodiments, the exemplary inventive computer-based systems/platforms, the exemplary inventive computer-based devices, and/or the exemplary inventive computer-based components of the present disclosure may be specifically configured to operate in an cloud computing/architecture such as, but not limiting to: infrastructure a service (IaaS), platform as a service (PaaS), and/or software as a service (SaaS). FIGS. 3 and 4 illustrate schematics of exemplary implementations of the cloud computing/architecture(s) in which the exemplary inventive computer-based systems/platforms, the exemplary inventive computer-based devices, and/or the exemplary inventive computer-based components of the present disclosure related to the collection, analysis and visualizing of real-time data in a centralized database and/or cloud storage may be specifically configured to operate.

FIG. 5 through 51 illustrate a system and method of processing and communicating information in real-time involving databases, database integration systems and local devices to provide real-time actionable data for decision making to an end user device from raw data collected, aggregated and normalized from across various vendor specific databases storing data in vendor specific formats. The following embodiments provide technical solutions and/or technical improvements that overcome technical problems, drawbacks and/or deficiencies in the technical fields involving data analytics, data visualization, and data collection pertaining to raw data stored in databases by a diversity of data source vendors. As explained in more detail, below, technical solutions and/or technical improvements herein include aspects of improved querying of vender specific data collection services, real-time collection and aggregation of queried data into common centralized formats through normalization of the data represented in disparate vendor specific formats, data point prioritization according to a scoring system for actionable information, and visualization of the data for real-time decision making applications including the generation of an actionable medical directive according to the real-time actionable data. Based on such technical features, further technical benefits become available to users and operators of these systems and methods. Moreover, various practical applications of the disclosed technology are also described, which provide further practical benefits to users and operators that are also new and useful improvements in the art.

Figure 5:
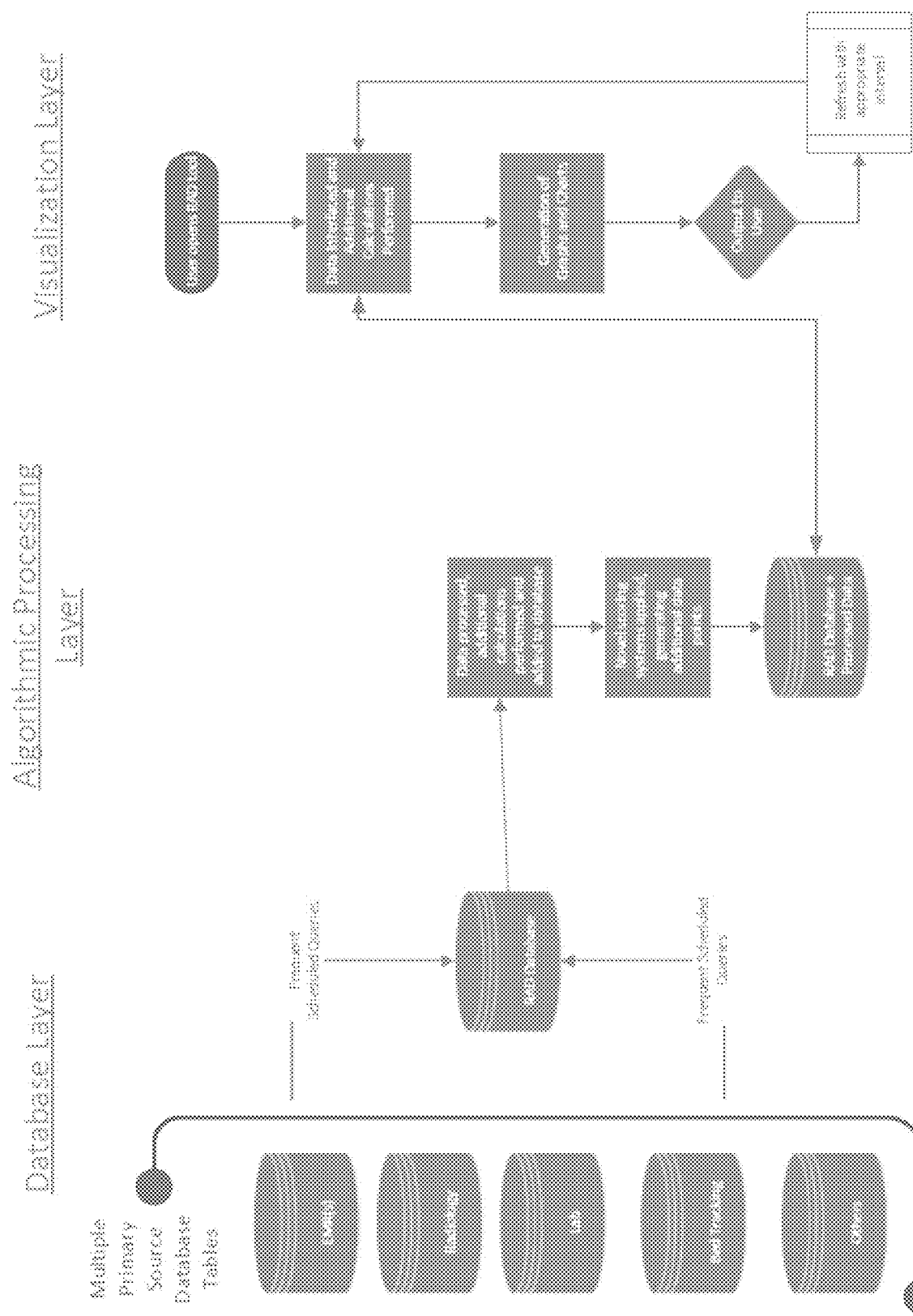

FIG. 5 illustrates a database layer of a real-time actionable data (RAD) database according to an embodiment of the present invention. In an embodiment, Real Time Actionable Data (RAD) is a suite of tools designed to gather data from a variety of sources, process and normalize it, and display it to the user in graphic and tabular fashions that are intuitive and directly related to real time decisions necessary in the operation of a medical business unit. In several cases, the normalized data is processed algorithmically using novel scoring systems to provide previously unknown insights and direct real-time decision making. In an embodiment, the RAD tools are designed to be HIPPA compliant, primary data source vendor agnostic, and able to be visualized by the end user on a variety of devices using only a web browser. In an embodiment, most tools can be used on phones, tablets, or desktop computers.

In an embodiment, a database layer queries data from multiple primary source tables of patient-related data in intervals of between, e.g., about 1 minutes and about 5 minutes. In an embodiment, the primary source tables correspond to multiple vendors of electronic medical record (EMR) services. The primary source tables collect raw data from users, such as workers, staff, customers, patients, or other personnel in real-time, for example, every 5 minutes. In an embodiment, the raw data can be collected by an application on a mobile device, such as a tablet or smartphone, or by any suitable digital entry solution by an on-site user recording the raw data in real-time. In some embodiments, the primary source tables may include data collected from medical measurement devices, such as, e.g., pulse oximeters, sphygmomanometers, magnetic resonance imaging (MRI), computer-aided tomography (CAT) scans, positron-emission tomography (PET) scans, x-ray images, blood glucose meters, cholesterol blood analysis devices, among other biomarker measuring devices and systems.

In some embodiments, the raw data relates to patient care, including, e.g., intake, discharge, test and lab results, lab test and other test status, bed occupancy, patient care professionals, among others, in addition to raw data related to healthcare facility administration, such as workforce monitoring, finance, billing, among others. In an embodiment, the primary source tables can be organized or categorized according to record type, such as; EMR, radiology orders and result, lab orders and results, bed tracking including occupancy or vacancy, and other suitable types, including, e.g., workforce monitoring data, finance, billing, among others.

In an embodiment, the primary source tables are queried at regular intervals to form a RAD database from across the primary source tables and the vendors. For example, clinical data can be queried in intervals between about 1 minute and about 5 minutes, historical data and calculations can be queried in intervals of between about 1 hour and about 1 day, and workforce monitoring data can be queried in intervals of up to about 1 month.

In an embodiment, the database layer can perform pre-processing of the queried data, such as, e.g., normalization, cleansing, or other pre-processing techniques to produce, e.g., normalized patient-related data. In some embodiments, the normalization, cleansing and other pre-processing facilitates restructuring the raw data, including the patient-related data from various vendors into a normalized, common format to produce common format normalized patient-related data. In an embodiment, the database layer can maintain the data in a database for a desired amount of time, such as a year or more. In another embodiment, the database layer can maintain the data in the RAD database indefinitely or for a selected amount of time.

In an embodiment, the RAD database is a centralized database. The queried data is pulled from the primary source tables, which may be stored in multiple databases, such as the databases of multiple different vendors. Thus, the primary source tables may be located in separate security domains or within a single security domain. In an embodiment, the RAD database can query each security domain to access all of the primary source tables regardless of vendor on a regular basis, such as in intervals between about 1 minute and about 5 minutes, between about 1 hour and about 1 day, or up to about 1 month or more, depending on data type.

In an embodiment, an algorithmic processing layer can analyze data in the centralized RAD database. In an embodiment, the algorithmic processing layer utilizes additional calculations, such as statistical analysis and data science techniques to determine statistical patterns, trends, and other characteristics and metrics of the data in the RAD database. The processed data is then added into the RAD database in intervals between about 1 minute and about 5 minutes, between about 1 hour and about 1 day, or up to about 1 month or more, depending on data type.

According to an embodiment of the present invention, the algorithmic processing layer can include software and/or hardware for generating the analyses, calculations and scoring described above, including a software program stored in a memory device with instructions performed by a processing device. The processing device can be located at the RAD database to communicate directly with the normalized data stored therein, or remotely on a remote user device or in a cloud application or web server. In some embodiments, the software and/or hardware can include a server in communication with the RAD database configured to process the normalized data, e.g., the common format normalized patient-related data, using a server architecture designed for implementing a server language, such as, e.g., Structured Query Language (SQL), Tableau, or other suitable database management system.

In an embodiment, the algorithmic processing layer can also implement scoring to determine prioritization of data. In an embodiment, scoring is performed by generating numerical scores for each item corresponding to the primary source tables. For example, a numerical score can be generated according to a look-up table with scores for conditions associated with each item. In an embodiment, the numerical scores are assigned algorithmically according to a scoring formula In some embodiments, the numerical scores are assigned based on metrics that define subsets of the patient-related data. In some embodiments, such metrics may include health markers such as heart rate, blood pressure, electrocardiogram results, a need for restraints, fall risk level, disposition (e.g., admitted, discharged, wait time, etc.), among others. Thus, in some embodiments, the metrics may be used to determine a patient-related data point associated each metric according to the patient-related data. A patient-related data point refers to a combination of a metric and an associated score in, e.g., points based on a scoring methodology. For example, a vitals data point of about 20 points can be determined based on vitals in the common format normalized patient-related data not being measured within a given threshold condition, such as, vitals not being measured within a range of about 10 and about 19. Thus, in some embodiments, analyzing the common format normalized patient-related data may be analyzed based on the metrics to deduce a data point including a score for each metric based on threshold conditions. Herein, the "threshold condition" refers to a set of predetermined thresholds specific to each metric that define a score for the data point associated with each metric for each patient. See, for example, FIG. 11.

In some embodiments, the scoring formula may include a scoring for healthcare facility-related metrics. In some embodiments, such metrics relate to operations of the healthcare facility, such as, e.g., finances, workforce management and monitoring, facility performance related to, e.g., wait times, bed occupancy, lab test orders and order completion, transportation, among other metrics pertaining to the operation, administration and management of the healthcare facility. Thus, the data, e.g., the common format normalized patient-related data, is scored based on the metrics and associated threshold conditions for scoring each metric.

In an embodiment, the data items can then be ordered sequential to form an order of priority. In an embodiment, the order data items and the scores are added to the RAD database and associated with the data items. In an embodiment, analysis by the algorithmic layer can be performed periodical to maintain real-time information corresponding to the data, such as in an interval of between about 1 minute and about 5 minutes, between about 1 hour and about 1 day, or up to about 1 month or more, depending on data type.

In some embodiments, the algorithmic processing layer may employ the order of priority to identify or otherwise determine resource needs and cause at least one real-time operational change to address the resource needs by generating at least one actionable medical directive. For example, in some embodiments, the order or priority may define higher or highest risk patients (high priority patients). Thus, in some embodiments, the higher or highest risk patients may be identified to match resources based on need/s, including modifications to resource deployments such as a redeployment of staff and/or equipment, among other resources. As a result, the algorithmic processing layer may then generate an actionable medical directive contemporaneously with the scoring to alert a user or administrator to address the resource needs. For example, in some embodiments, the actionable medical directive may include a notification to match resources, e.g., staff, such as nurses, doctors, and/or support staff, with a location within a healthcare facility having high priority patients; and/or to match equipment, such as bandages, splints, medications (for, e.g., oral, intravenous, intramuscular, or sub-cutaneous administration and equipment required to administer same), equipment for drawing blood (e.g., catheters, needles, collecting vessels), gurneys, surgical equipment, x-ray equipment, ultrasound equipment, electrocardiogram (EKG/ECG) equipment, and other equipment (e.g., portable and stationary units) in a location within a healthcare facility having high priority patients. In some embodiments, a high priority patient or location in a healthcare facility having high priority patients is identified via actionable medical directive as needing resources, such as, for example, access to specific medical equipment, ministrations by specialized medical staff, increased surveillance via medical monitoring equipment and/or medical staff, immediate access to a medication/s, a change in dosing of a medication/s or therapeutic regimen, and/or a clinical reevaluation.

High priority patients may be identified at least in part via a patient-related data metric relating to, for example, a high risk of falling, evidence of trauma, sepsis, cardiac arrest, ST elevation acute myocardial infraction (STEMI), delirium, mental instability, and/or violent behavior, which metrics are analyzed by the algorithmic processing layer to generate a patient related data point, which in turn is ranked. See also, for example, FIGS. 11, 50, and 51.

In some embodiments, matching of resources may include increasing resources, reducing resources, reallocating resources, and/or redistributing resources among other matchings. In some embodiments, the order of priority may identify patients experiencing long wait times in a given department. Thus, the actionable medical directive may include a notification to increase a priority of lab orders from the department, and/or redistribute equipment to the department (e.g., gurneys, wheelchairs, and/or medications) to reduce wait times.

In some embodiments, allocation of resources may include matching of medical equipment based on healthcare facility-related data metrics relating to patient's previous experience at the healthcare facility and feedback received pertaining to the experience. Such data metrics may be acquired via, for example, Press Ganey patient satisfaction survey results. In an embodiment, if a particular patient was chronically cold during an initial visit to the healthcare facility and required additional allocation of resources (e.g., blankets, hot compresses, socks, and/or hot drinks) to be comfortable during the initial visit, then upon re-admittance to the healthcare facility or another healthcare facility in the system, the potential need for similar allocation of resources for that particular patient would be analyzed by the algorithmic processing layer and may be presented by the visualization layer.

In some embodiments, allocation of resources may include matching of a particular combination of resources with at least one particular patient in at least one particular location of at least one of the particular healthcare facilities in the healthcare system. For example, a medical practitioner (a medical practitioner with, e.g., a particular skill set, personality, and/or medical equipment), medical practitioners, and/or medical equipment is matched to a particular healthcare facility location or particular patient in need thereof to match care provided to a particular need. Such matching could be performed iteratively to match a particular resource or combination of resources sequentially to different particular healthcare facility locations and/or particular patients in need thereof. Other actionable medical directives are contemplated.

With respect to iterative matching of a particular resource or combination of resources sequentially to different particular healthcare facility locations and/or particular patients in need thereof, the algorithmic processing layer would analyze metrics relating to completion of task/s pertaining to a first matching of particular resources to a particular need, as well as utilization capacity of resources. A medical practitioner having a particular skill set, medical equipment, and/or personality may have a utilization capacity of a plurality of patients, which capacity varies based on a variety of factors, such as, the location in the healthcare facility (e.g., operating room, emergency room, intensive care unit, maternity floor, pediatric unit, regular floor, etc.— each of which has patients requiring different intensities of attention), severity of the conditions of patients being treated, the age of patients, and/or level of independence of the patients. In some embodiments, the utilization capacity of the medical practitioner can be one patient, at least one patient, at least two patients, at least three patients, at least four patients, at least five patients, at least ten patients, 2-5 patients, 3-5 patients, 2-10 patients, 3-10 patients, 2-15 patients, 3-15 patients at a time. Utilization capacity of a resource may also refer to the utilization capacity of, for example, medical equipment or a suite of medical equipment (combination of medical equipment that can be used in conjunction such as those used in operating rooms) in a healthcare facility or facilities. In some embodiments, the utilization capacity of a resource such as a medical equipment unit or suite thereof may be one patient, at least one patient, at least two patients, at least three patients, at least four patients, at least five patients, at least ten patients, 2-5 patients, 3-5 patients, 2-10 patients, 3-10 patients, 2-15 patients, 3-15 patients at a time. In a particular embodiment, the utilization capacity of a medical equipment unit or suite thereof is one patient at a time.

The algorithmic processing layer analyzes the utilization capacity of a particular resource at a particular healthcare facility location at an initial matching and at each iterative match thereafter.

In a particular embodiment of iterative matching of a particular resource or combination of resources sequentially to different particular healthcare facility locations and/or particular patients in need thereof, the algorithmic processing layer analyzes metrics indicating that a task/s pertaining to a first matching of particular resources to a particular need has been completed, thereby returning the resource to the pool of available resources as reflected by the healthcare facility-related data. In a particular embodiment, the particular resource is, e.g., a portable ultrasound machine. Upon completion of the first matching, the ultrasound machine is available for a second matching of a particular resource to a particular need as reflected by the healthcare facility-related data and analyzed by the algorithmic processing layer accordingly. In another particular embodiment, the particular resource is a medical practitioner having a particular skill set, medical equipment, and/or personality, who upon completion of a task/s relating to a first matching of particular resources to a particular need, is identified as an available resource in the pool of available resources as reflected by the healthcare facility-related data. Such a medical practitioner may also be identified as an available resource in the pool of available resources as reflected by the healthcare facility-related data due to analysis of the practitioner's utilization capacity and a determination that the practitioner can be matched as a resource to additional particular needs without exceeding the practitioner's utilization capacity. Upon completion of the first matching or identification of additional available utilization capacity for the medical practitioner, the medical practitioner having a particular skill set, medical equipment, and/or personality is available for a second matching of a particular resource to a particular need as reflected by the healthcare facility-related data and analyzed by the algorithmic processing layer accordingly. In an embodiment, a visualization layer can present the information in the RAD database to users on demand, including scores, metrics and actionable medical directives produced by the algorithmic layer. In an embodiment, when each tool is activated by the end user, the visualization layer opens a connection to all necessary tables created in the database and algorithmic processing layers in each of the necessary security domains.

According to an embodiment of the present invention, the visualization layer can include software and/or hardware for generating the visualization tools described above, including a software program stored in a memory device with instructions performed by a processing device.

The processing device can be located at the RAD database to communicate directly with the normalized data stored therein, or remotely on a remote user device or in a cloud application or web server. In an embodiment, the visualization layer includes a server and/or a server or database management language, such as SQL or Tableau, among other suitable languages to form a processing system configured to manipulate the normalized data of the RAD database to generate user-centric tools.

In an embodiment, further calculations are performed upon the data as necessary to support creation of visualizations that are intuitive and interactive for the end user. For example, these visualizations may include (but are not limited to): charts (bar, line, area, scatter plots, control charts, tree diagrams), tables, interactive elements (hovers, click-through explanations, etc.) and other visualizations. In an embodiment, when appropriate, the visualization layer will automatically refresh with whatever frequency is necessary to keep the data being visualized current against the data being updated in the database and algorithmic processing layers. In general, this refresh frequency can be approximately every 3 to 5 minutes. In an embodiment, the visualizations are interactive and self-explanatory using legends, hovers, and other modalities. The visualizations can provide real time, specific, actionable information not previously available in a centralized location. Additionally, the visualizations provide data generated by the algorithmic processing layer which was not previously available in any fashion at all.

Figure 6:
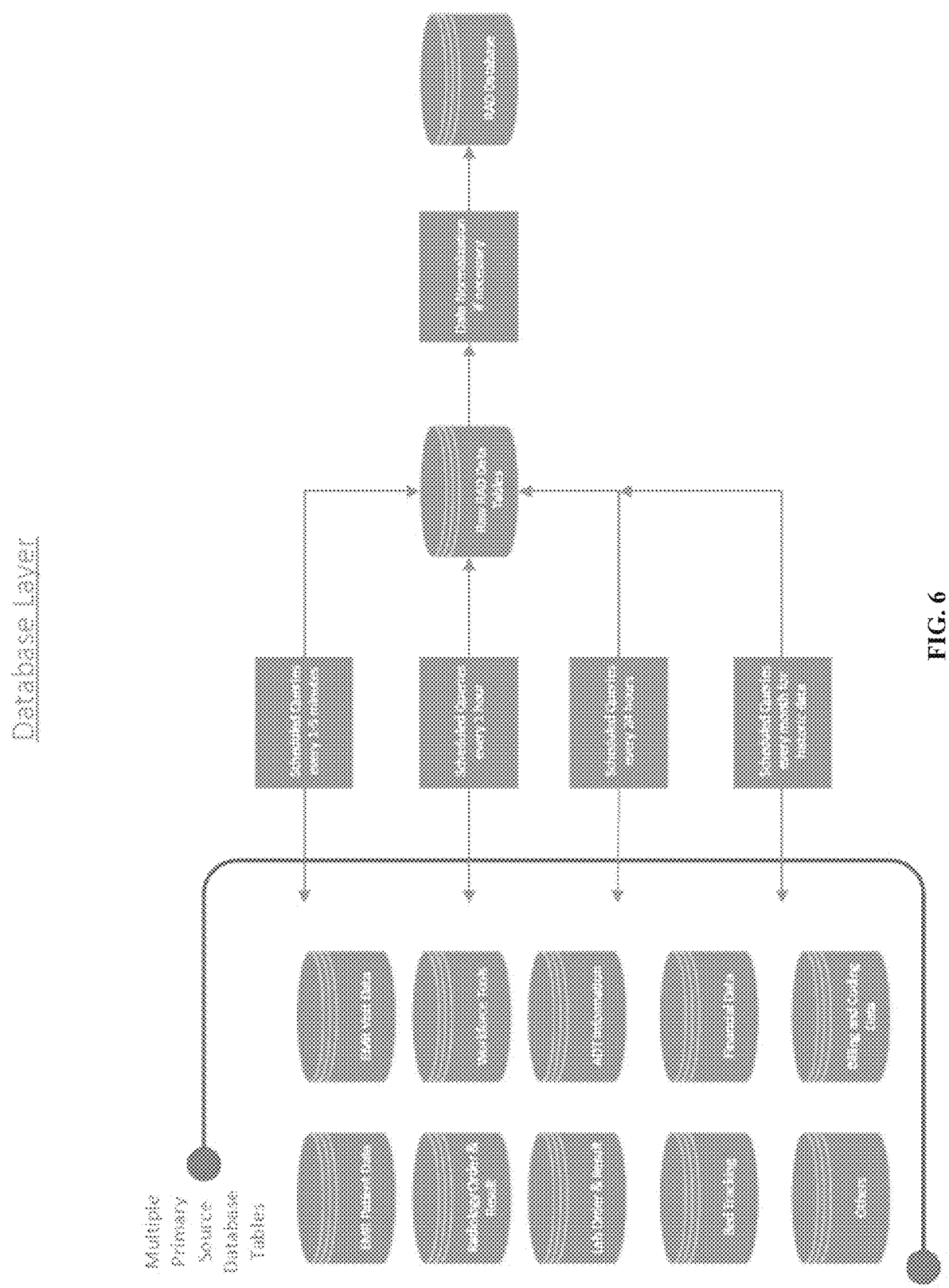

FIG. 6 illustrates a database layer of a RAD suite for medical services according to an embodiment of the present invention. In an embodiment, the database layer includes multiple primary source database tables, including, but not limited to, (1) EMR patient data, (2) EMR visit data, (3) Radiology orders and results, (4) Lab orders and results, (5) Bed tracking, (6) Workforce tools, (7) ADT information, (8) Financial data, (9) Billing and Coding data, and (10) any other pertinent data. The primary source database tables can be provided and maintained by one or more data storage vendors, such as, e.g., cloud service vendors, on-premises storage vendors, data management software vendors, or other vendors suitable for maintaining the primary source database tables. The primary source database tables can also be associated with a particular facility, a ward or department within a particular facility, or with multiple facilities. In an embodiment, the primary source database tables are included within a common security domain. Here, a security domain refers to any set of elements, e.g., physical or virtual network of data storage and processing devices, security policy, security authority and/or a set of security-relevant activities, in which the elements are managed in accordance with a common security policy. For example, in an embodiment, the primary source database tables are maintained on a common network behind a firewall.

In an embodiment, a raw RAD database queries each of the primary source database tables to compile raw medical service related data from across facilities and vendors. These queries occur in a variety of time intervals depending upon how current the necessary data must be in order to operate in the desired RAD tool. In an embodiment, this varies from every 1 to 5 minutes for most clinical data, 1 hour to 1 day for data used for historical calculations to up to every 1 month for historical workforce monitoring tools, coding and billing. In an embodiment, the raw RAD database stores the queried data in raw RAD tables.

In an embodiment, the raw RAD tables a preprocessed. In an embodiment, the preprocessing includes data normalization to normalize the raw RAD tables across vendor and primary source table formats. The RAD database is then updated with the normalized RAD tables. The updating can include, e.g., replacing the unnormalized data, adding the normalized RAD tables, or other suitable database updating techniques. Thus, in an embodiment, the RAD database forms a centralized database of normalized data from a variety of primary source tables produced by multiple different vendors and facilities within a security domain.

In an embodiment, the data normalization can normalize the raw data in the primary source tables for common formatting and common statistical representation. The data normalization facilitates consistent processing and analysis of data collected in different ways and by different vendors. For example, a primary source table can include data from multiple vendors, each of which may have collected relevant data using different metrics. For example, one provider may record a time of arrival and a time of provider visit, but not recording wait duration, while another provider may record a time of arrival and wait duration, but not time of provider visit. Data normalization corrects for differences in the representations of each metric of the patient-health service relationship to facilitate more accurate and reliable analysis of data.

Figure 7:
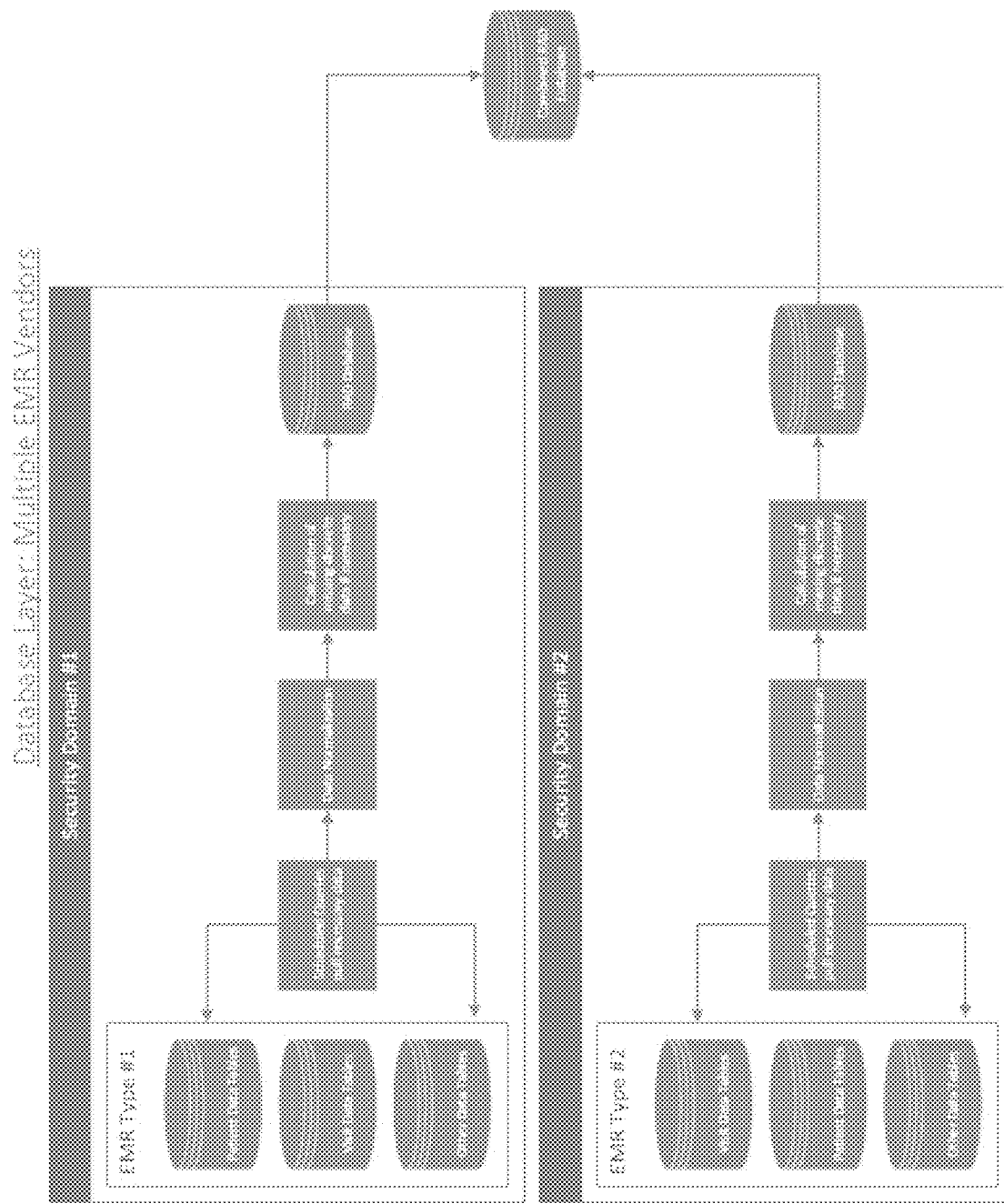

FIG. 7 illustrates a database layer querying data within two distinct security domains according to an embodiment of the present invention.

In an embodiment, data is acquired from several different clinical electronic medical record systems from different vendors with vastly different database structures located across different security domains. Similar to above, here, a security domain refers to any set of elements, e.g., physical or virtual network of data storage and processing devices, security policy, security authority and/or a set of security-relevant activities, in which the elements are managed in accordance with a common security policy. Each security domain can include primary source tables having information collected and maintained by one or more distinct vendors.

To facilitate the data acquisition, separate data acquisition processes are run within each different security domain. Each data acquisition process stores the data in a respective RAD database within a corresponding security domain. In an embodiment, each data acquisition process includes scheduled queries of primary source tables of a respective EMR type, normalization of the queried data, such as the normalization described above, and calculation of missing discrete data where necessary. The primary source tables are queried in intervals between about 1 minute and about 5 minutes, between about 1 hour and about 1 day, or up to about 1 month or more, depending on data type The acquired data can be normalized so that data from one vendor's database can be equally compared against data from another vendor's database. Here, normalization refers to the application of formal rules to the representation of data in the database. The formal rules can be designed to reduce data redundancy and proper enforcement of dependencies such that the same data is represented in same form while reducing anomalies. Thus, the data normalization reformats the representation of data to conform to a particular set of formal rules that results in a particular representation of that data corresponding to subject of the data. For example, patient census data is formatted to conform to specific formal rules concerning how the population and movement of patients are represented in, e.g., a data table. In this example, upon normalization, all patient census data is formatted according to the formal rules for patient census data, and thus all share a common format to the representation of the patient census data.

Additionally, normalization can also include statistical normalization. Here, the statistical normalization can include the adjustment of values measured on different scales to a common scale and different distributions of data to a normal distribution. Because different vendors may have measured and collected data for a given database of primary source data tables, the data contained therein may have been measured according to different methodologies, resulting in different scales. Normalization can convert raw data from the various methodologies into a common scale and distribution such that further statistical analysis can be more effectively and accurately performed.

Examples of this normalization can include, but are not limited to a formal rule ensuring that data types are consistent (string vs. integer, string vs. float, float vs. integer, etc), and formal rules concerning what fields are used to represent information, thus accounting for data that is not maintained in one of the vendor's record in a discrete state. For example, one vendor's product may not maintain a specific length of stay duration as a discrete data element. In such a case, the value would be calculated from the necessary timestamps during the data normalization process to enforce a formal rule concerning a field for duration of stay in patient census data.

Thus, in an embodiment, the data normalization process compares data of similar types and determines differences in recorded information, including format differences, and missing or additional data points or other statistically significant variations in data representation. Data normalization constructs a common data format for the corresponding data type and applies the format to all of the data of that type, calculating any missing information and adjust the data representations. As a result, data collected by different vendor solutions implementing different data recordation methods can be compared against one another.

In an embodiment, the data from each RAD database in each security domain is pulled and compiled into a combined RAD database to form a global RAD database with normalized data from each security domain. In an embodiment, the data from each RAD database is pulled in intervals between about 1 minute and about 5 minutes, between about 1 hour and about 1 day, or up to about 1 month or more, depending on data type.

Figure 8:
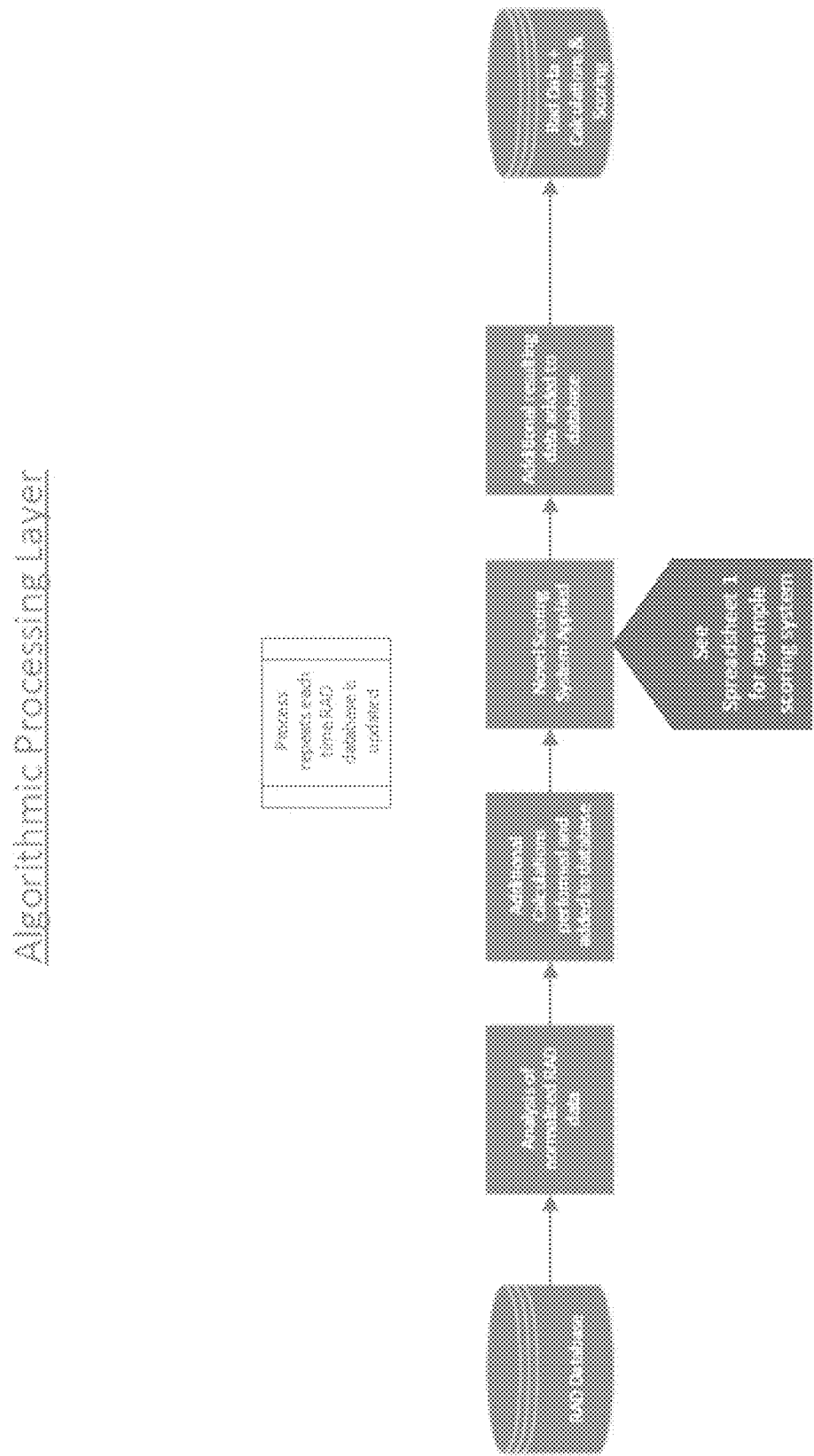

FIG. 8 illustrates algorithmic processing layer of a RAD suite according to an embodiment of the present invention.

In an embodiment, normalized data is pulled from the centralized RAD database for analysis. In an embodiment, the analysis can include a statistical analysis of the normalized data to represent trends and behaviors pertaining to services and outcomes. For example, means, standard deviations, and statistical distributions, among other analyses can be performed. The results of the analysis and calculations are provided to the centralized RAD database for storage with the normalized data in intervals between about 1 minute and about 5 minutes, between about 1 hour and about 1 day, or up to about 1 month or more, depending on data type.

In an embodiment, after the various data elements are acquired, normalized and stored in a centralized RAD database, a separate algorithmic scoring process is applied to create additional data points. In an embodiment, the algorithmic scoring process is also done in an ongoing scheduled fashion with whatever frequency is necessary to support the necessary RAD tool of the RAD suite. In an embodiment, the frequency varies from every 1 to 5 minutes to every 1 hour.

In an embodiment, a variety of the data elements are analyzed and compared using a standardized scoring system to produce numerical scores that allow items (such as currently active patients or tasks) to be placed into sequential order based on the results of the calculations. In an embodiment, the results of these calculations are also written to the centralized RAD database location. The calculations can be performed concurrently with the additional analysis, such as the statistical analysis described above. In an embodiment, the scoring calculations are performed periodically, independently from the above described analyses, in intervals between about 1 minute and about 5 minutes, between about 1 hour and about 1 day, or up to about 1 month or more, depending on data type.

Figure 9:
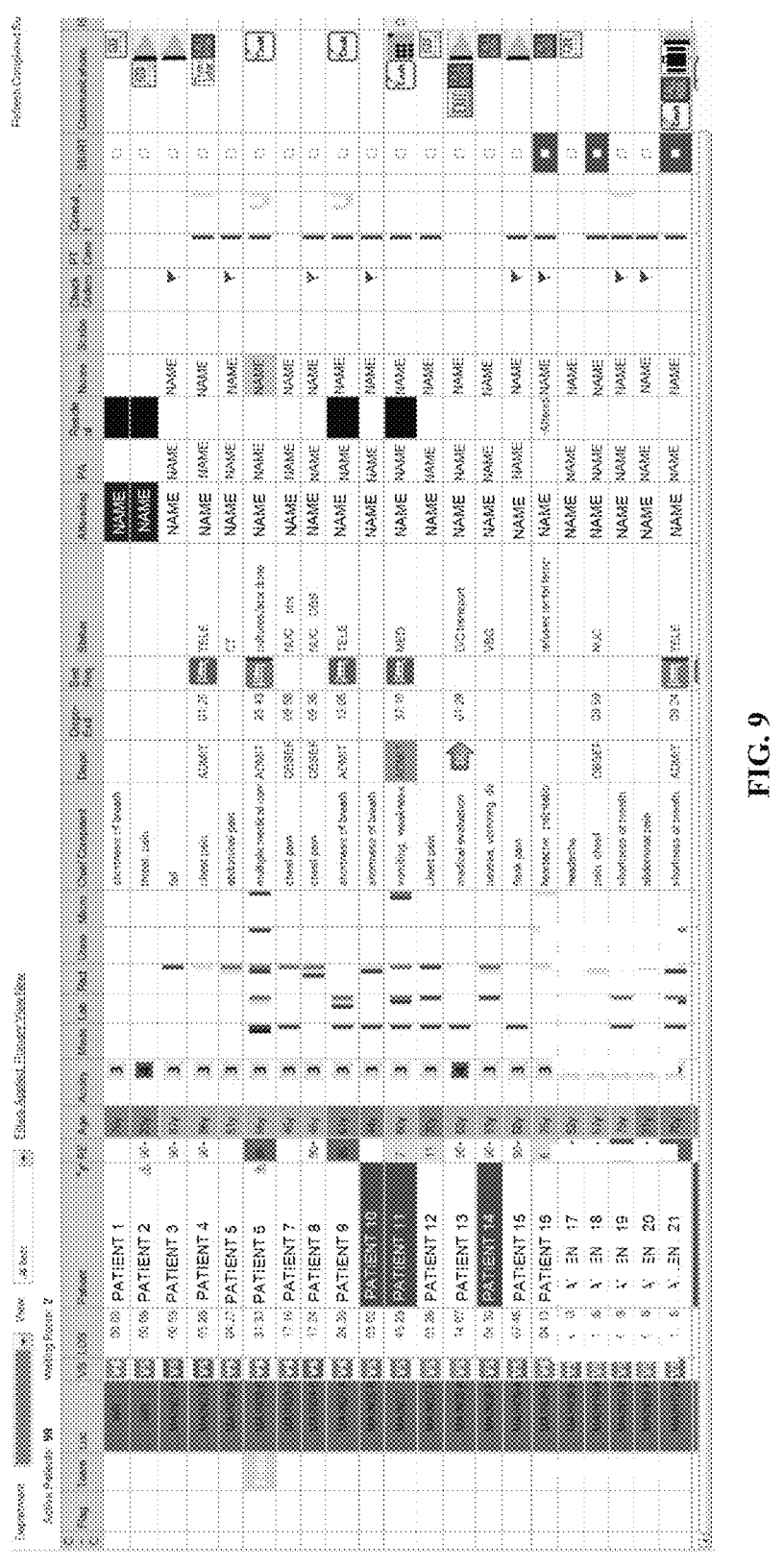

FIG. 9 illustrates a conventional patient tracking board. The tracking board shows patients and corresponding data, such as location, services provided, attending health professionals and other information. However, the tracking board does not provide historic or predictive analytics, only shows 21 patients at a time, requires frequent scrolling, and is cumbersome to use.

Figure 10:
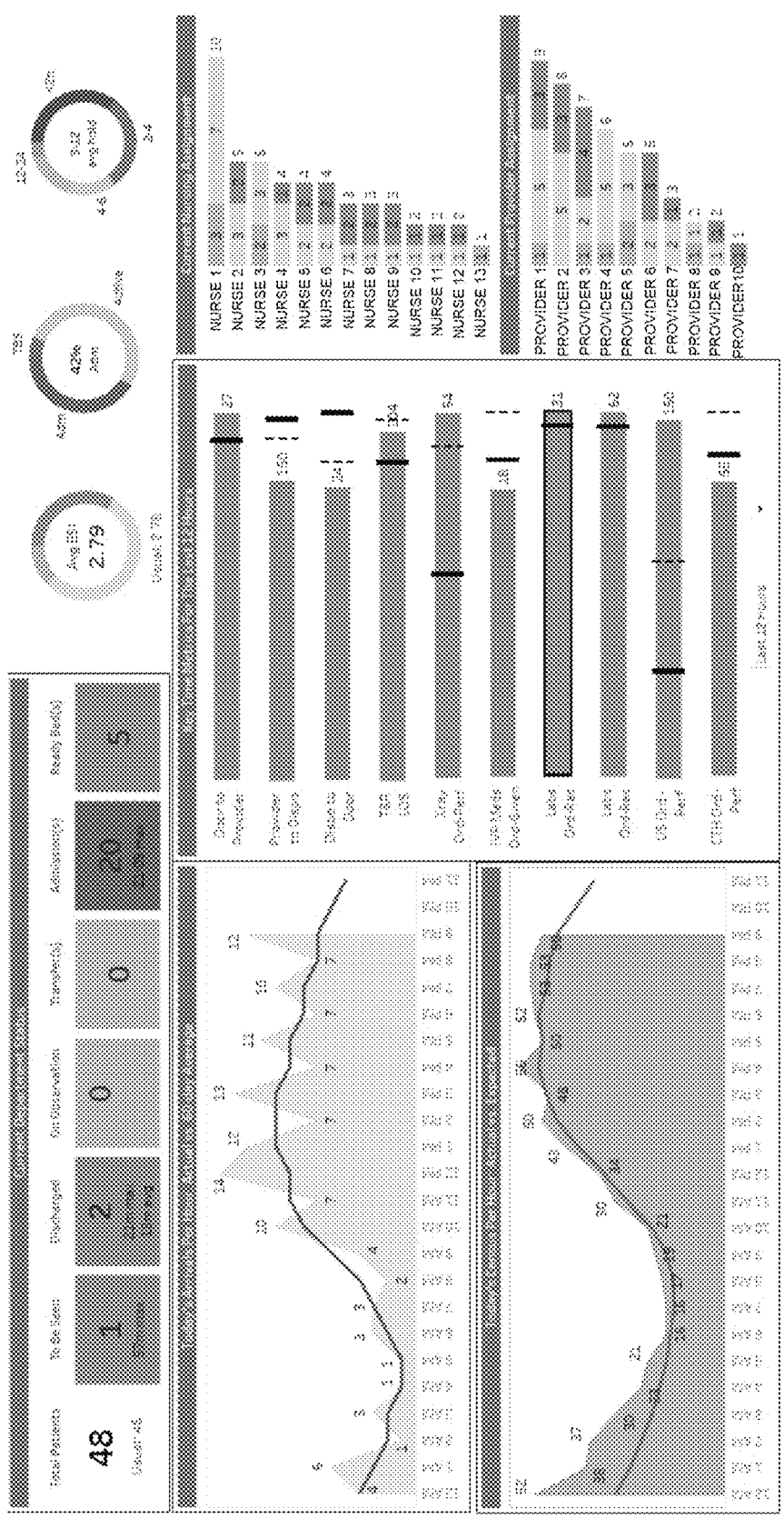

FIG. 10 illustrates a data visualization screen according to an embodiment of the present invention. According to one embodiment, the data visualization screen displays historic, current, and predictive analytics related to patient admission, from time of admission to time of discharge. In one embodiment, the visualization screen depicts time metrics for a variety of patient services, patient arrival statistics, census statistics, staff workload, and other real-time data. Previously unavailable metrics are now available and update every 5 minutes.

According to an embodiment, the metrics are queried by a database layer. In an embodiment, the database layer queries each EMR vendor database every 5 minutes directly from each of the following database source tables: (a) EMR patient and visit observation tables, (b) EMR vital sign and other flowsheet tables, (c) ADT arrival/discharge information (using interface data), (d) ADT quick/full registration status (using interface data), (e) ADT copay collection requirement status (*certain sites only), (f) ED patient location tables, (g) Nurse/Provider assignment tables, (h) Inpatient bed assignment and tracking tables (using interface data), (i) Lab order and result tables, (j) Radiology order and result tables, (k) Medication order and administration status tables, (1) Other miscellaneous order and status tables (EKG, restraints, etc), and (m) Historical patient satisfaction survey response data tables. In an embodiment, the collected data is normalized across each vendor's system and stored in a centralized database of normalized RAD tables.

In an embodiment, queries can be run for radiology order status tables, lab order status tables and general order status tables every, e.g., hour. In an embodiment, queries every, e.g., 24 hours can be run for EMR patient and visit observation tables and ADT arrival/discharge tables.

In an embodiment, the queried data, past 60-day performance metrics are calculated for key department indicators such as door to doctor time, treat and release length of stay, etc., which are stored in a centralized table. This data can also be used to create snapshots of hourly arrival and census data for each department which is stored centrally and used for several RAD tools as well as EDSTATs.

In an embodiment, the data in the centralized tables can be analyzed by an algorithmic processing layer. In an embodiment, the algorithmic processing layer determined a current average patient acuity (as indicated by Emergency Severity Index) by calculating and comparing data with same department, day of week and hourly adjusted historic averages, and then flagged appropriately. Flagged patients can be presented to a user, such as a health care professional or administrator to determine a most effective allocation of resources for treating patients with the highest possible care. For example, as depicted in FIG. 10, nurses and providers can be organized by patient counts, categorized by the Emergency Severity Index. Thus, a workload for each personnel member can be easily determined and patient care can be allocated to more efficiently distribute workloads, thus resulting in better and more efficient care provided to the patients.

Current average patient acuity (as indicated by Emergency Severity Index) is calculated and compared with same department, day of week and hourly adjusted historic averages and flagged appropriately.

Similarly, in an embodiment, current patient counts in each disposition status as well as average and maximum patient times in status are calculated and compared with same site, day of week and hour of day adjusted historic averages and flagged appropriately. Likewise, in an embodiment, arrivals by hour and census by hour are calculated and compared with same site, day of week adjusted historic averages and flagged appropriately. In an embodiment, calculations are performed on hourly data to determine key department time metrics such as door to provider, treat and release length of stay as well as performance intervals such as radiology time from ordered to performed, etc. These calculated metrics are compared with pre-determined department goals as well as calculated 60-day department averages and flagged appropriately. Accordingly, patient volumes and treatment metrics can be easily viewed by a user across a network of departments and facilities. As a result, allocation of personnel and routing of ambulances can be more efficiently planned to make better use of resources at each facility or department. These uses as well as others can increase the efficiency of transportation and treatment of patients, reducing wait times and increasing the quality of care.

In an embodiment, multiple patient and visit characteristics are used in a novel scoring system to determine patient risk of danger or bad patient experience. Each patient is assigned a score which allows them to be prioritized in a variety of ways.

In an embodiment, a visualization layer can use the calculated metrics to form real-time tools for visualization of real-time actionable data. For example, in an embodiment, an operations monitor including multiple additional calculations to support summation of values and creation of visualizations. In an embodiment, normalized data, processed data, and flagging information created in the database and visualization layer are used to create 6 different interactive data display elements: (1) current department status, (2) arrivals per hour metrics, (3) census per hour metrics, (4) key time metrics, (5) current nursing assignments, and (6) current provider assignments. Each of these visualizations provides facility managers and personnel with easily understandable information regarding the performances and status of providers, nurses, departments, tasks and the healthcare network overall. As a result, a user can easily deduce choke points in patient processing and treatment, and re-allocate personnel and resources to eliminate the choke point and increase efficiency and quality of care. Thus, actionable medical directive can be generated to improve the patient care experience by improving efficiency and quality. Ultimately, the improvements in efficiency and quality results in reduced patient wait times and a better standard of care that can save lives and reduce the risk of errors and complications in treatment that may lead to long term health problems with the patient or recurring conditions.

In an embodiment, the visualization layer can also generate an "Open Tasks" tool and a "Safety/Rounding Assistant" tool for visualization of task and patient safety metrics.

FIG. 11 illustrates patient prioritization according to patient risk of danger or bad patient experience via a scoring method according to an embodiment of the present invention. In an embodiment, a patient can be prioritized according to score in an algorithm layer, such as the algorithm layer described above with reference to FIGS. 8 and/or 10. The score is determined by applying points for each metric according to specified conditions of those metrics to establish a data point including a metric and its associated score for a patient based on patient-related data, such as, e.g., common format normalized patient-related data. In an embodiment, the points are correlated to a patient metric according to a condition as shown in FIG. 11, including a threshold condition that defines threshold intervals specific to each metric for assigning points. In an embodiment, the patient score is determined by summing the points for each satisfied threshold condition for a patient. In an embodiment, a number of points for each patient metric can be applied using a predetermined look-up table specifying a number of points for each pre-defined condition of a metric. However, other embodiments are contemplated. For example, in another embodiment, a numerical measurement corresponding to a metric can be weighted to produce a score. The weights applied to the measurement can be a constant value for each metric, or the weight can be set according to various measurement ranges. Other methods and algorithms are contemplated.

The patient score is an example of the scoring mechanism of the present invention that can quantify the quality and efficiency of patient care. For example, wait times for various basic health services, such as measurement of vitals and electrocardiogram (EKG) measurements can be scored according to the amount of time a request for such services take to be performed. The sum of the scores for each metric can produce a quantifiable indication of the quality of care for a particular patient.

Healthcare personnel can easily view an indication of patient scores to deduce which patients need to the most immediate treatment. As a result, the score can assist personnel with prioritizing patients in, e.g., triage decisions. Thus, in an embodiment, patient and task scores can provide easily understandable and actionable information regarding the efficacy of a current allocation of personnel and resource in real-time. However, scores for other aspects of healthcare operations are also contemplated.

Figure 12:
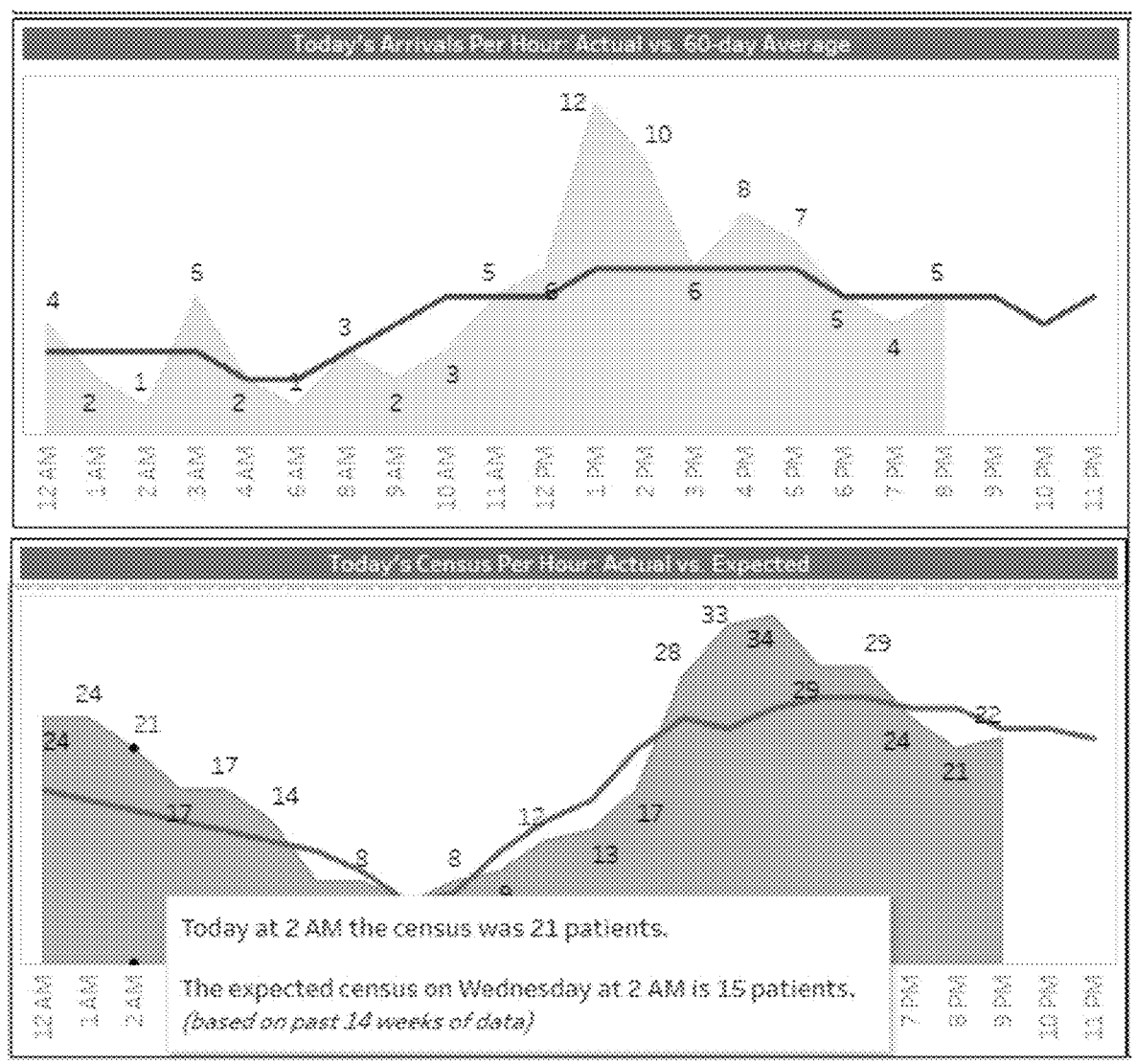

FIG. 12 illustrates an hourly arrivals data visualization and an hourly census visualization according to an embodiment of the present invention. In one embodiment, hour by hour arrival and census information are compared with historical averages (matched for day of the week). In an embodiment, the ability to look at any specific day in history as well as overall averages and maximums is also possible. This information can inform staffing decisions when flexible staffing models are used by scheduling personnel at the times of day with the highest patient traffic.

Figure 13:
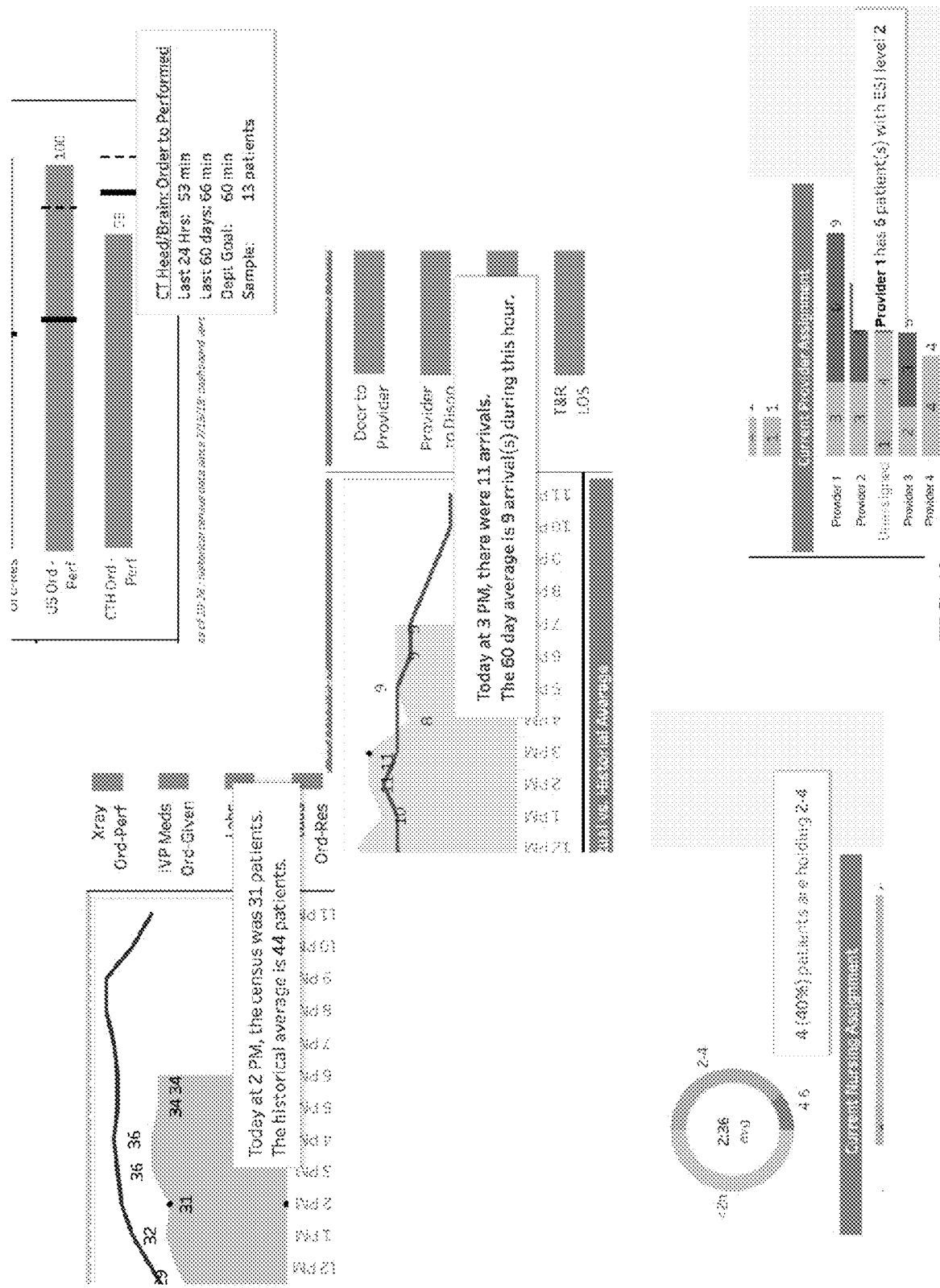

FIG. 13 illustrates hover boxes over various visualization elements according to an embodiment of the present invention. In an embodiment, each table, graph or other element for visualizing data can produce additional information by hover a selection mechanism over the visualization element. For example, an embodiment of the present invention includes hovering a mouse cursor over a data visualization, such as a graph, to produce a hover box including real-time data descriptions corresponding to the time at which the mouse cursor is located. Using the hover box, a user can see both the overall trends for, e.g., patient censuses, while concurrently being able to see details of, e.g., a patient census at a particular time. Any problems corresponding to treatment of patients or slow-downs in department operations can be easily deduced from the hover boxes. Thus, the hover-boxes can provide easily understandable and actionable information regarding the efficacy of a current allocation of personnel and resource in real-time.

Figure 14:
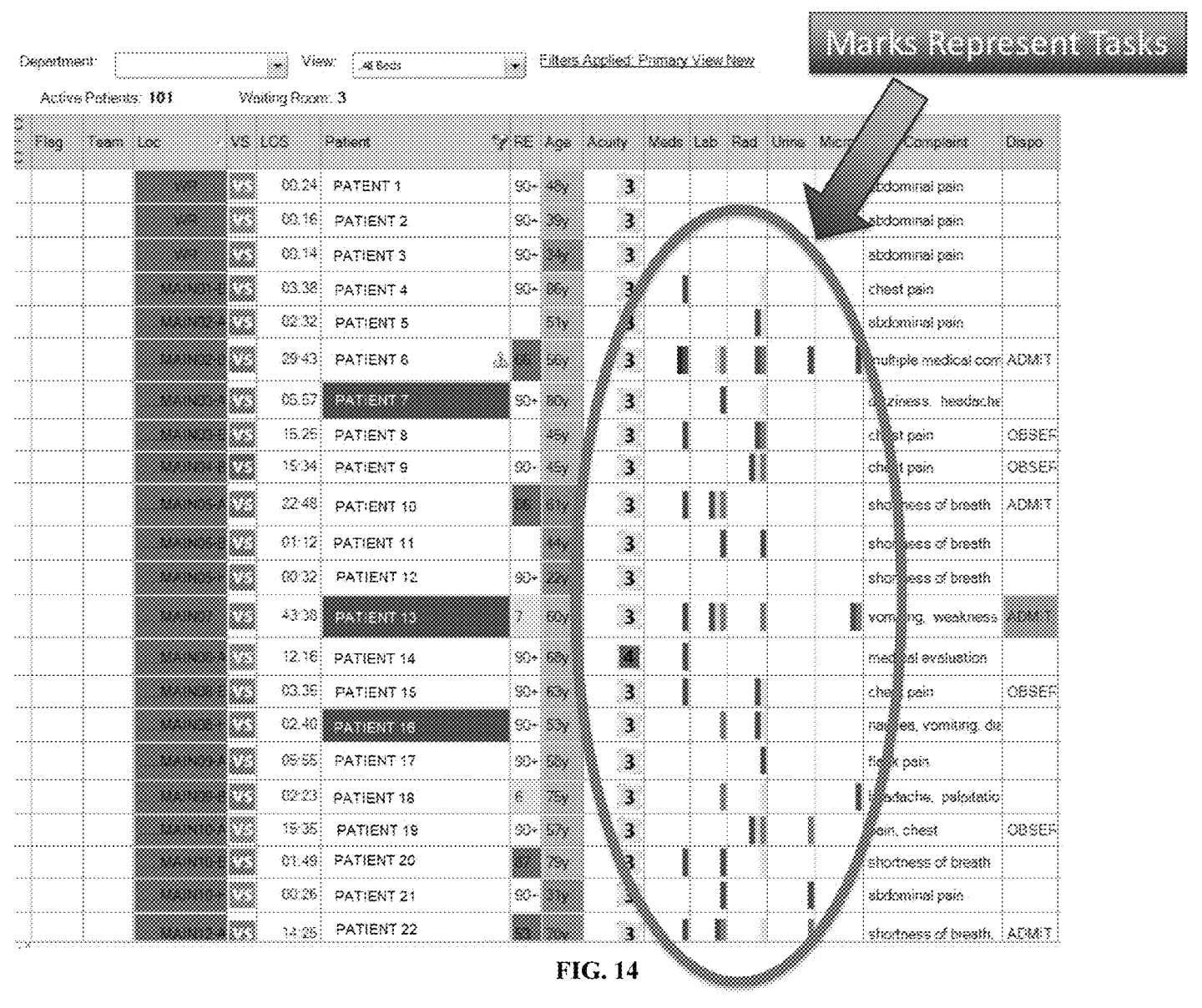

FIG. 14 illustrates a conventional patient tracking board, similar to that of FIG. 1. Patient tracking boards may represent tasks corresponding to a particular patient by showing a simple marking in a box for the represented task. Representing tasks to be performed and tasks already performed in an understandable and digestible fashion is another major challenge.

Figure 15:
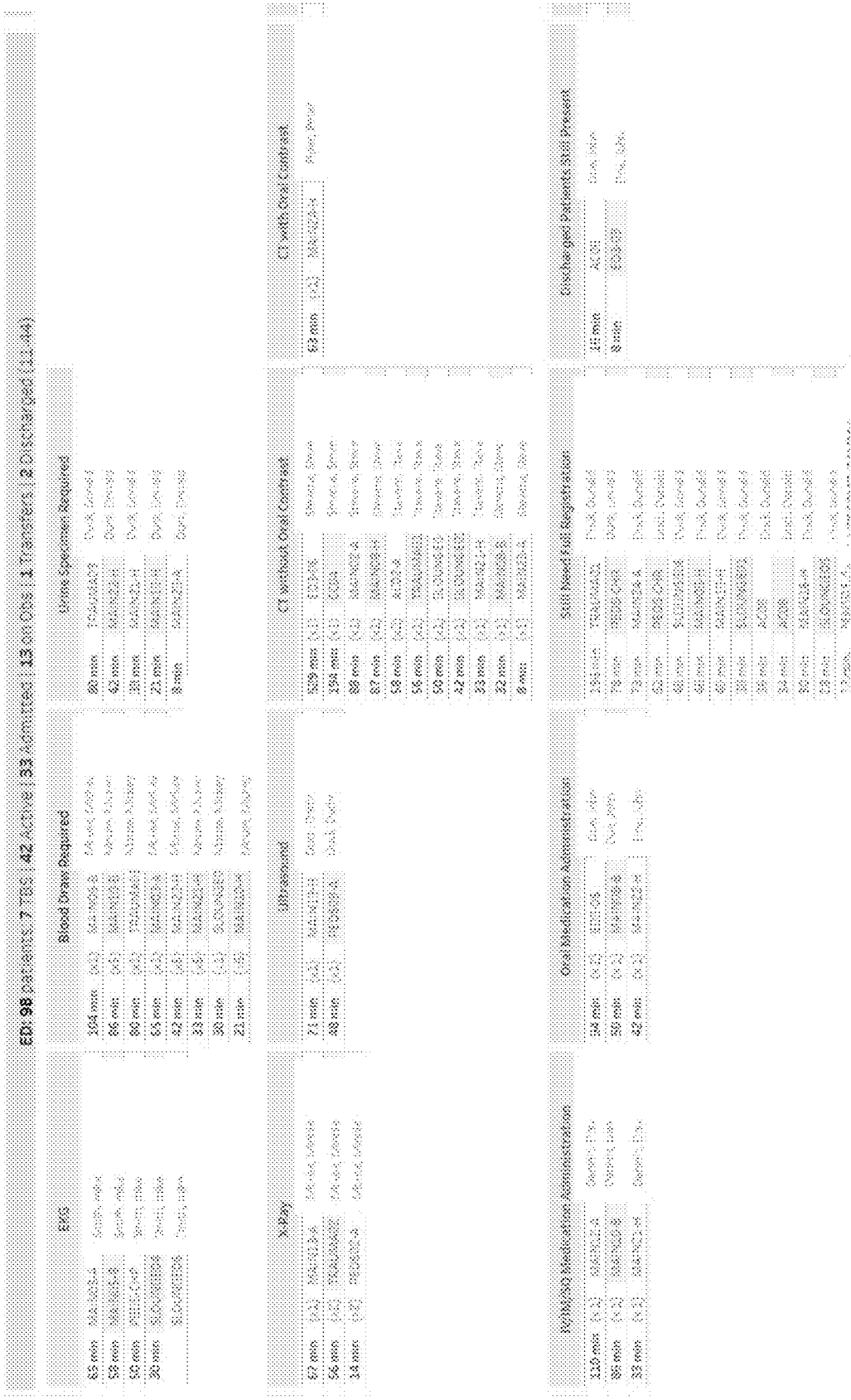

FIG. 15 illustrates a task-based visualization of patient services according to an embodiment of the present invention. The task-based visualization organizes scheduled or required tasks according to tables corresponding to each task. In an embodiment, the tables depict real-time statistics with prioritized lists for patients utilizing the respective service.

In an embodiment, the task-based visualization can be implemented as an "Open Tasks" tool, such as the "Open Tasks" tool described above with reference to FIG. 10. In an embodiment, Additional calculations are performed to determine number of minutes between ordering of each item and the current time. Tables can be generated for each common task type with an interactive prioritized list of all patients currently awaiting that task and how long they have been waiting. In an embodiment, a user can view the task-based visualization and easily see patients and services that are causing slow-downs or receiving insufficient resources. As a result, the task-based visualization can show a user where resources could be redirected to improve operations, and ultimate improve patient care. Additionally, the task-based visualization in conjunction with the patient and/or task scoring can order the patients and tasks in lists such that a user can deduce at-a-glance the patients and tasks that need the most immediate attention and/or resources for effective care. Thus, the task-based visualization tool can provide easily understandable and actionable information regarding the efficacy of a current allocation of personnel and resource in real-time.

FIG. 16 illustrates task-based visualization of patient services according to an embodiment of the present invention. In an embodiment, each box displays everyone in the selected department/zone with a given type of open task, organized by how long the task has been open. Second column displays how many tasks of this type are still open. Hovering will display specific items, allowing rapid sorting of tasks by importance. For example, in an "Open Tasks" tool, such as the "Open Tasks" tool described above with reference to FIG. 15, for some task types such as medication administration, hovers provide additional insights such as medication type/name. As described above, theses task-based visualizations can provide quick, at-a-glance information to a user regarding the patients and tasks that would benefit most from increased resource and personnel allocation. Thus, the task-based visualization tool can provide easily understandable and actionable information regarding the efficacy of a current allocation of personnel and resource in real-time.

Figure 17:
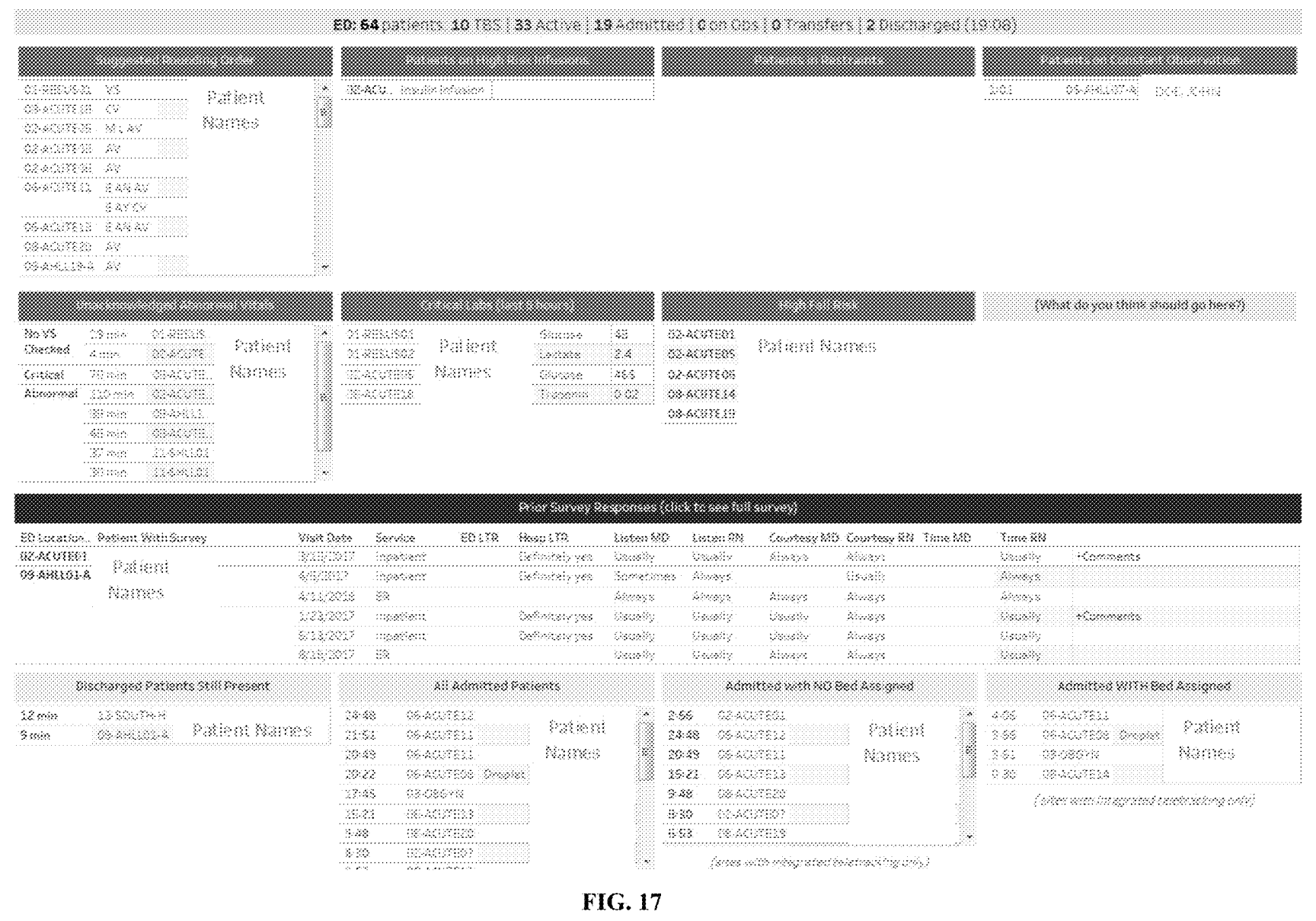

FIG. 17 illustrates a real-time department monitor according to an embodiment of the present invention. In an embodiment, the real-time department monitor includes a safety and rounding assistant with prioritization of high risk patients in rounding order, as well as safety risk analysis for each patient.

In an embodiment, tables are generated for many of the commonly known high risk indicators with an interactive list of patients that have that indicator. Indicators include those patients in restraints, on constant observation, those with abnormal/critical or missing vital signs, those with recent critical lab values, those identified to be at high fall risk and those on high risk infusion medications. When appropriate, time in that status can be calculated and displayed.

In an embodiment, a table is generated indicating any currently present patient that has completed a patient experience survey in the past 2 years. The patient's responses to several key questions are demonstrated and flagged if negative. If the user selects one of these lines, the entire patient survey is displayed including any patient comments.

In an embodiment, tables are generated to indicate patients that are in high risk disposition categories such as discharged but still present, admitted (with or without bed assignment) and those on isolation for possible infectious diseases. These lists are prioritized by calculated time in status. For example, in an embodiment, patients can be prioritized in, e.g., provider and nurse rounding schedules using the output of a scoring system used in an algorithmic layer, such as the novel scoring system described above with reference to FIGS. 10 and 11. For example, a table can be generated displaying a "Suggested Rounding Order". In an embodiment, this table prioritizes the currently present patients based on their likelihood of benefiting from a leadership rounding visit. The reasons for the suggestion (as generated by the scoring system) are provided with additional information available in a hover. Thus, in an embodiment, the rounding assistant tool can provide easily understandable and actionable information regarding the efficacy of a current allocation of personnel and resource in real-time.

FIG. 18 illustrates a patient survey with comments according to an embodiment of the present invention. In an embodiment, a click reveals a new window showing the patient's entire survey and comments. In an embodiment, closing this window returns to a rounding assistant, such as the rounding assistant depicted in FIG. 17. The patient survey can provide a user, such as a manager, administrator, provider and/or nurse with useful information regarding the any deficiencies in the providing of care and treatment to individuals. Where a rounding assistant tool, such as the rounding assistant depicted in FIG. 17, provides quantitative visualization of treatment efficiency and quality, the patient surveys can provide a qualitative assessment. Both in conjunction and independently, the rounding assistant tool and the patient surveys can provide easily understandable and actionable information regarding the efficacy of a current allocation of personnel and resource in real-time.

Figure 19:

FIG. 19 illustrates a "Rounding Assistant, to go" for mobile applications according to an embodiment of the present invention. In an embodiment, the tools of the rounding assistant depicted in FIG. 17 are also available in a phone and tablet edition which are more convenient for use while rounding in a unit. In an embodiment, selecting a patient's name will explain why the patient was selected for suggested rounding. In an embodiment, a tool to assist during a data-driven rounding visit is also contemplated to provide accountability and collection of data to help determine the root cause of quality and satisfaction issues.

In an embodiment, the "Rounding Assistant, to go" can be a "Safety/Rounding Assistant" as described above with reference to FIG. 17 in a mobile friendly (large or small tablet as well as phone sized) display to facilitate easy use while rounding. In an embodiment, these versions also allow for detailed filtering of the suggested rounding order based on current departmental priorities (for instance, focusing on decreasing boarding time for admitted patients, or improving patient satisfaction scores for patients in a rapid treatment area).

Figure 20:

FIG. 20 illustrates visualization for real-time status by department according to an embodiment of the present invention.

FIG. 21 illustrates visualization for real-time status of departments including real-time current holds for each department according to an embodiment of the present invention. The current holds can include a number of admitted patients, as well as wait times, updated in real-time, or in regular intervals, e.g., between about every 1 minute and about every 5 minutes, or between about every 5 minutes and about every 1 hour, or other suitable update interval. Thus, a user can easily deduce departments with insufficient resources. As a result, the current holds visualization tool can provide easily understandable and actionable information regarding the efficacy of a current allocation of personnel and resource in real-time.

Figure 22:
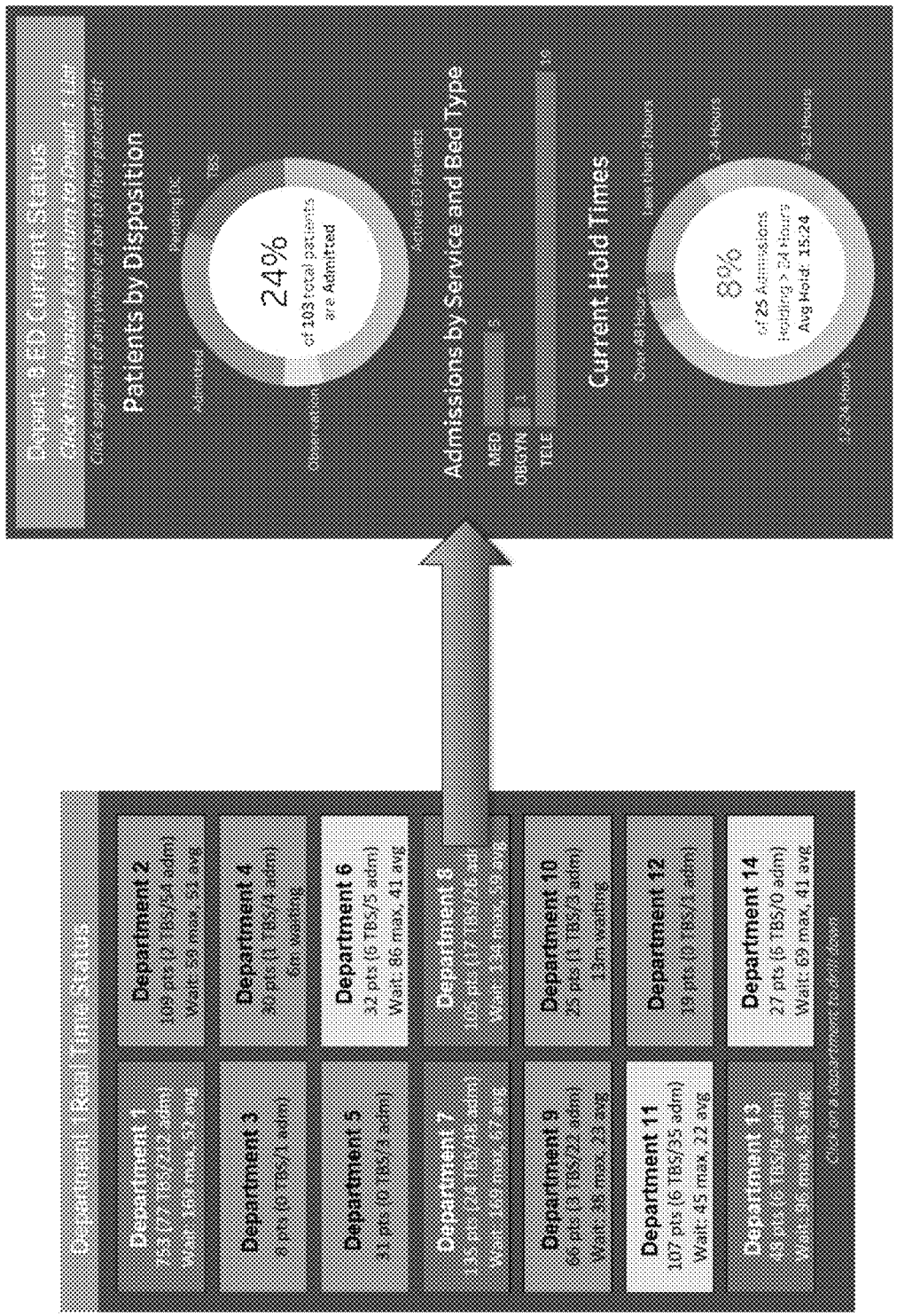

FIG. 22 illustrates detailed data visualization for a given department selected from a real-time departmental status screen according to an embodiment of the present invention.

Figure 23:
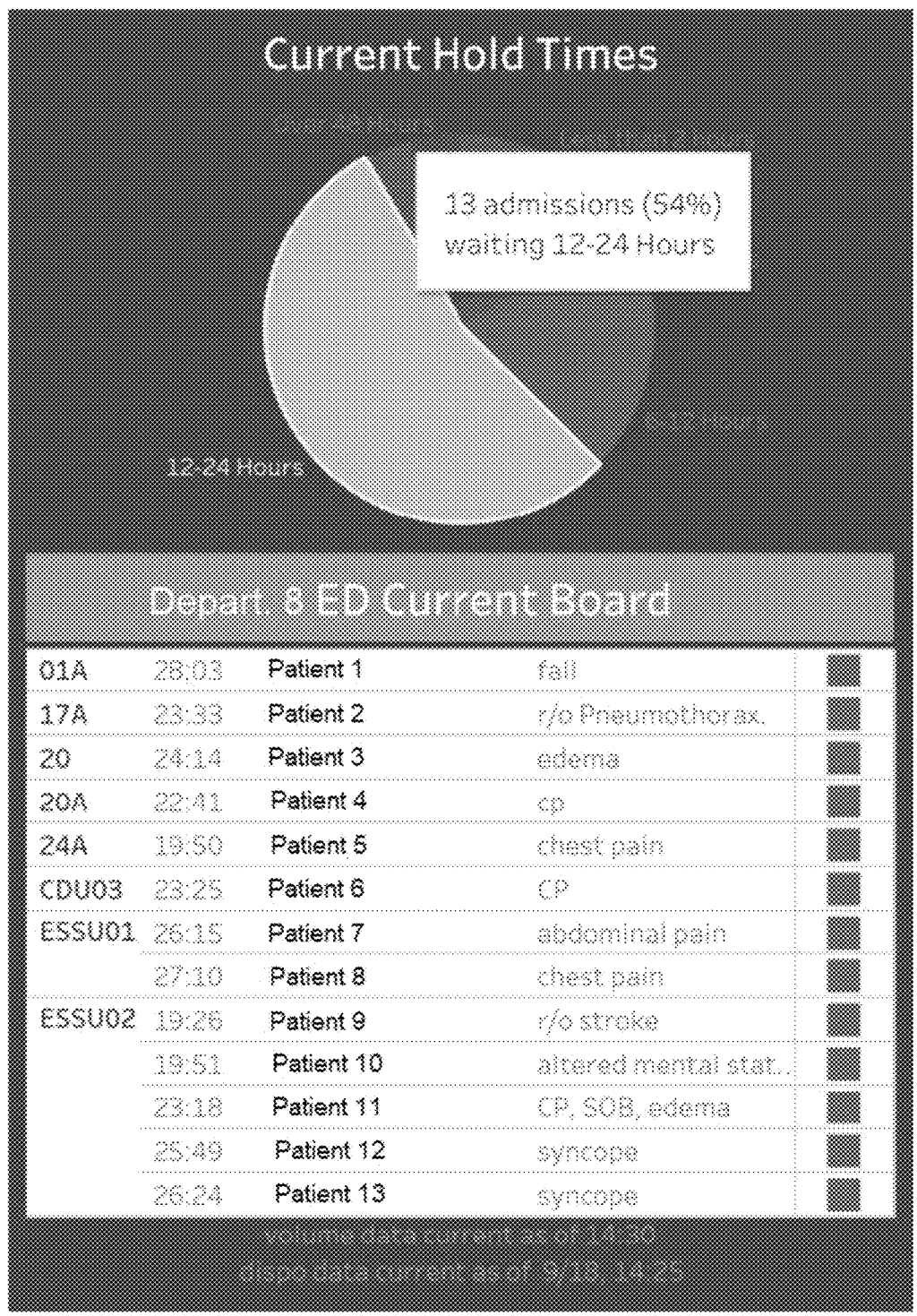

FIG. 23 illustrates detailed hold time statistics in real-time for a selected department according to an embodiment of the present invention. In an embodiment, all lists immediately filter based on any selection and hovering over any data element will explain it and offer additional insights. These insights can provide a user with additional details that may assist with determining any insufficiencies in personnel or resource allocations. Thus, the insights can facilitate easily understandable and actionable information regarding the efficacy of a current allocation of personnel and resource in real-time.

Figure 24:
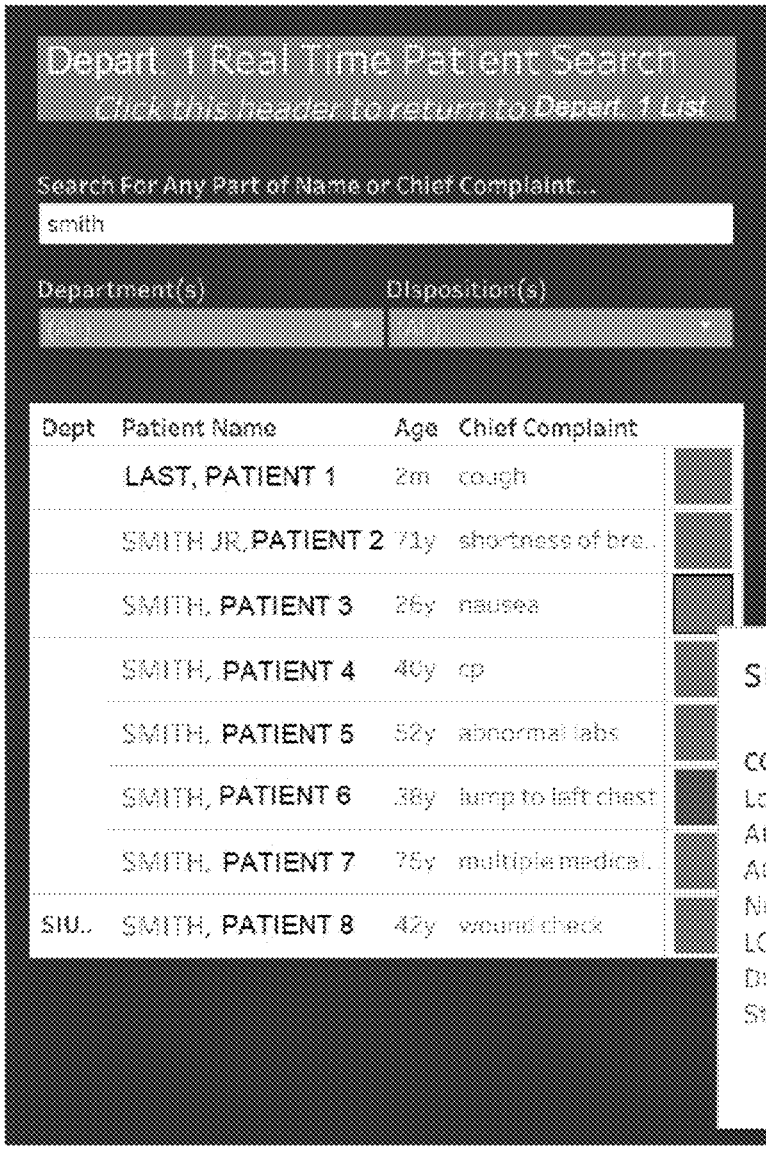

FIG. 24 illustrates a real-time patient search according to an embodiment of the present invention. In an embodiment, a patient can be located anywhere in real-time by entering any portion of a patient's name or chief complaint. In an embodiment, matches anywhere in the Service Line are presented. In an embodiment, hovering provides visit data. Previously this was only possible by calling each ED individually. Personnel can use the search tool to determine in real-time, where a patient is located and what treatment they are receiving. As such, specific patient treatment can be monitored and tracked, and the patient can be easily found where communication with the patient is desired. For example, where updated treatment information or inquiry is available, or where a family member arrives, a user can find the appropriate patient and provide the patient with the updated treatment information or inquiry, or direct the family to the patient's location.

Figure 25:
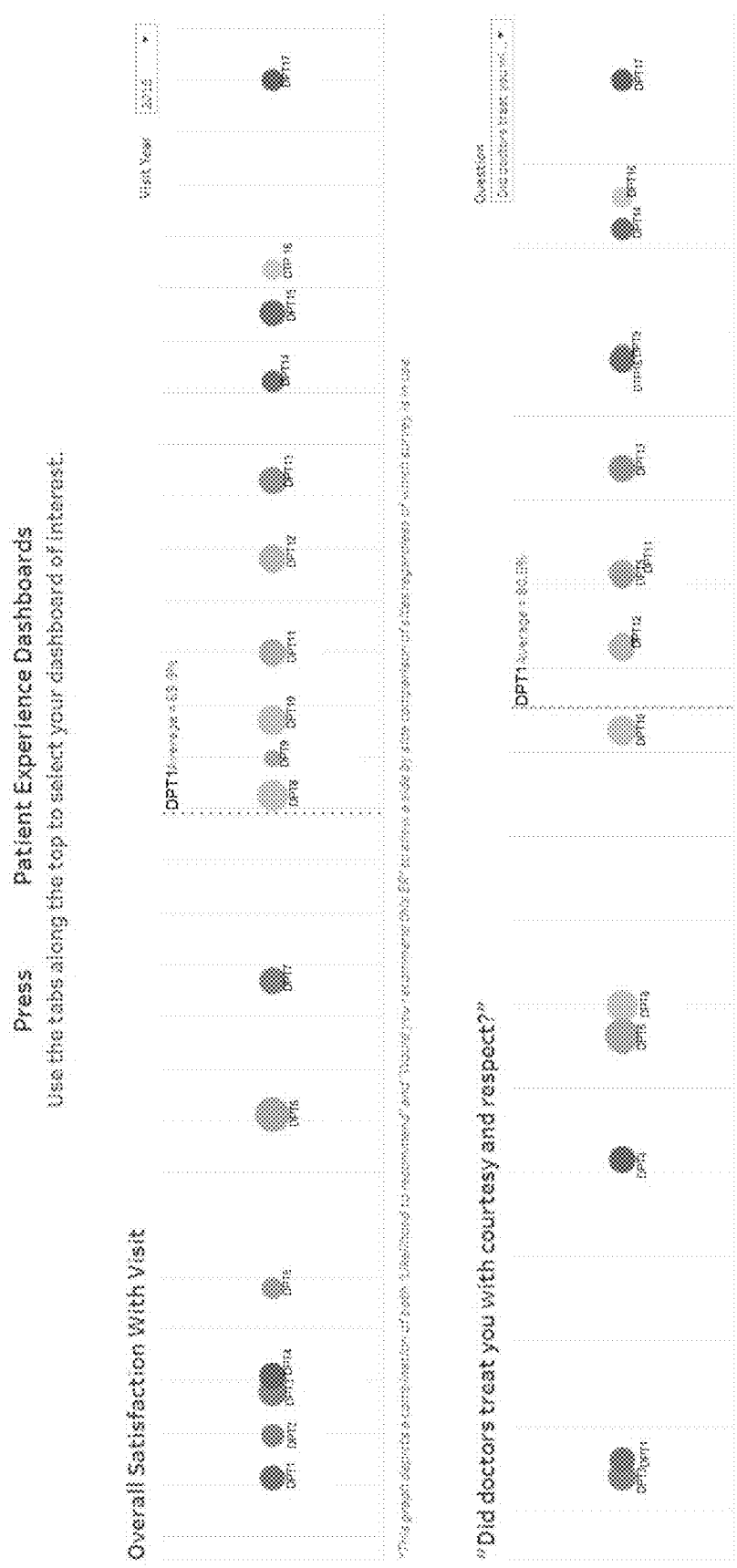

FIG. 25 illustrates survey statistics in real-time from a Service Line View according to an embodiment of the present invention. In an embodiment, the Service Line View includes all facilities in communication with RAD database of the present invention. The survey statistics provide an easily viewable and understandable representation of the quality of patient care at each department according to patient feedback. Thus, a user can easily identify departments that would benefit from improved personnel and resource allocation. Thus, this tool can provide easily understandable and actionable information regarding the efficacy of a current allocation of personnel and resource in real-time.

Figure 26:
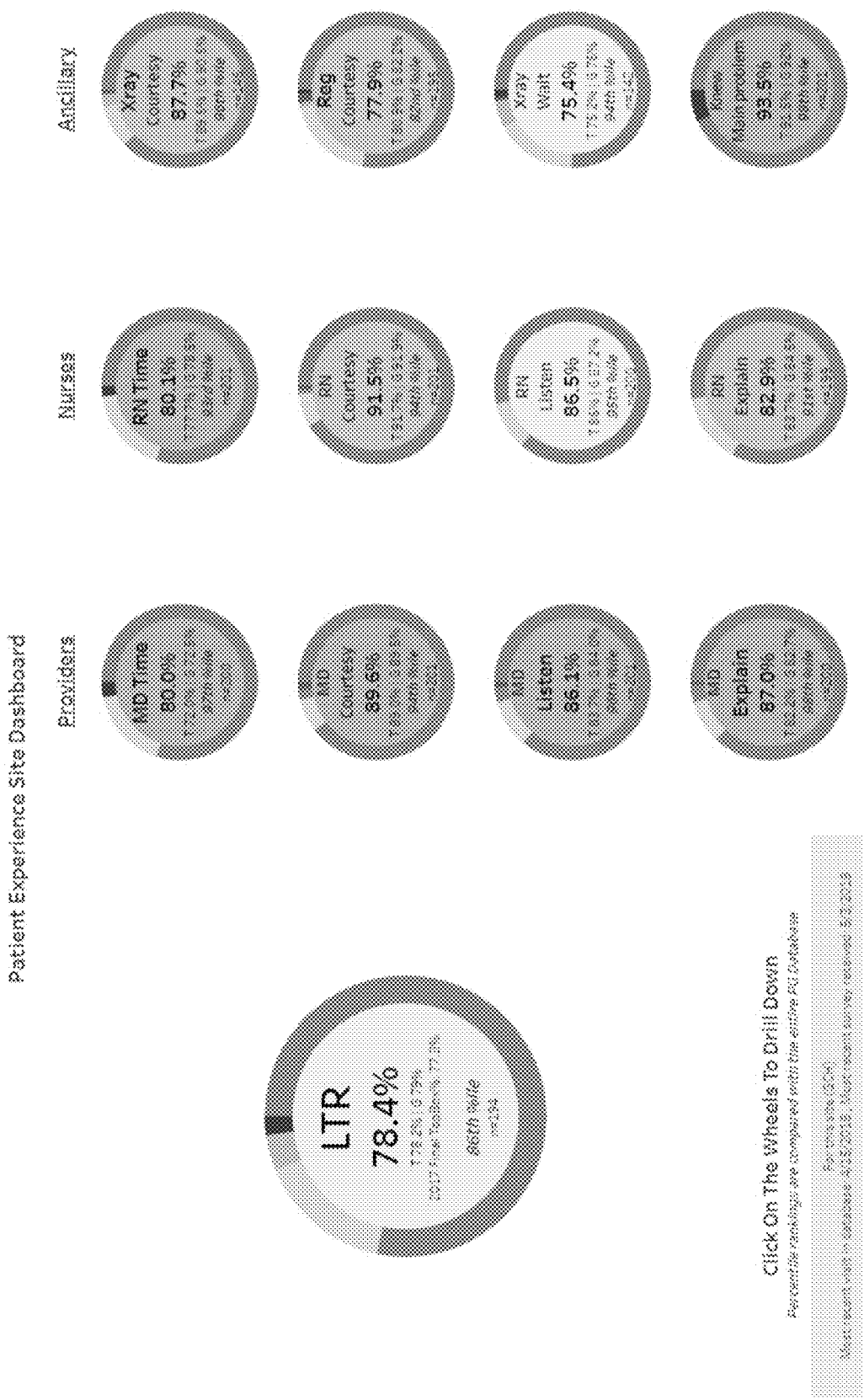

FIG. 26 illustrates a dashboard with real-time patient experience data according to an embodiment of the present invention. In an embodiment, clicking on a category can generate a drill-down screen with detailed real-time data related to, e.g., aspects of a relationship between a patient and healthcare professionals according to user surveys. In an embodiment, the visualizations can be color coded charts or graphs, such as pie charts, with additional information regarding survey statistics. The statistics and data that the visualizations are based on can be updated in real-time or substantially real-time, such as updated in intervals ranging from about every 1 minute to about every 5 minutes, or up to about every 1 hour or more. A user can view the visualizations to easily deduce areas of improvement in the care-giving relationship for personnel to improve patient care quality and experience.

Figure 27:
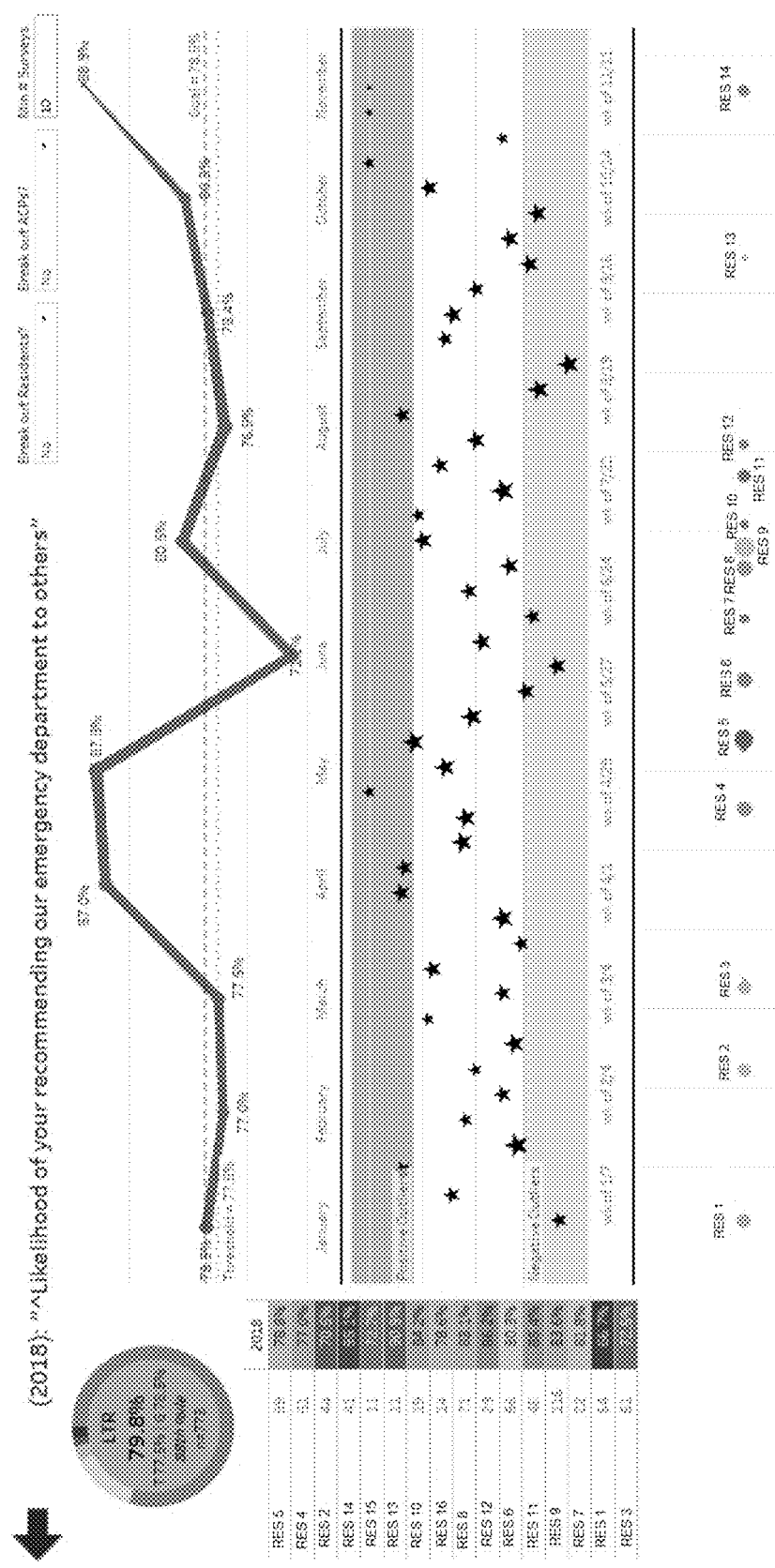

FIG. 27 illustrates a detailed view of real-time patient experience data for a category of the patient experience according to an embodiment of the present invention. In an embodiment, the detailed view corresponds to a drill-down screen as described with reference to FIG. 26 above. In an embodiment, the drill-down screen can include historical tracking through time of a particular survey question for a particular aspect of the patient experience, such as the likelihood of recommending a particular emergency department to others. A user can, therefore, track patient satisfaction through time to easily deduce how changes in personnel and service management affect the patient experience through time. A user can correlate the changing patient experience with changes that may bring improvements to care and satisfaction.

Figure 28:
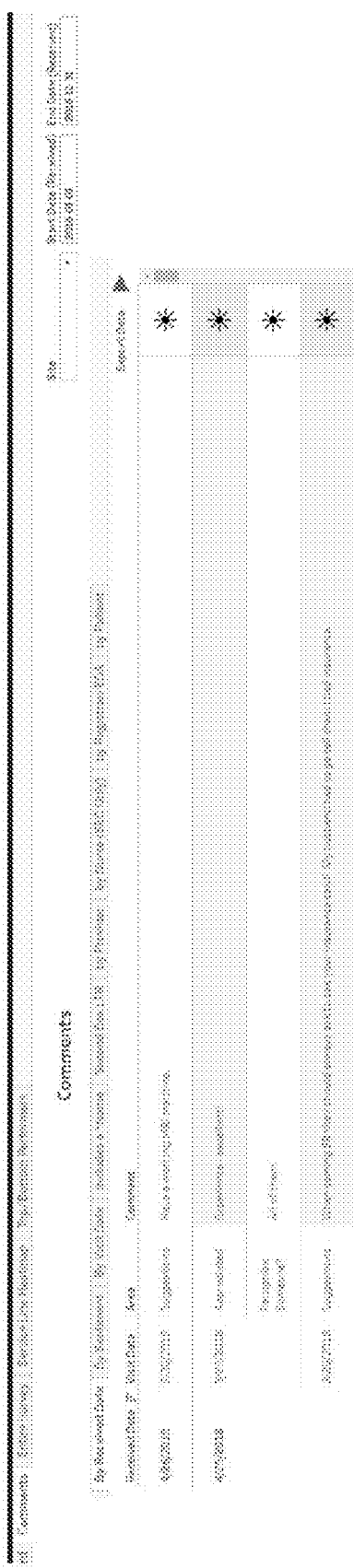

FIG. 28 illustrates a comments section for real-time patient experience data according to an embodiment of the present invention. In an embodiment, the comments section can be sorted by received date, visit date, sentiment, comments that include someone's name, patients who gave a "4" for LTR, as well as by provider, nurse (SEC), registrar (LHGV), and patient. In an embodiment, comments can be filtered by received date, and exported directly to Excel. The comments can be updated in real-time or substantially real-time, such as updated in intervals ranging from about every 1 minute to about every 5 minutes, or up to about every 1 hour or more. This gives a user quick and real-time access to specifics about a patient's reasoning for particular survey response, thus potentially affecting personnel and resource decision making in real-time.

Figure 29:

FIG. 29 illustrates a hover box in a comments section for real-time patient experience data according an embodiment of the present invention. In an embodiment, more detail can be present in a box upon hovering a selection mechanism over a field of the comments section. For example, an embodiment of the hover box includes detailed visit information associated with each comment by hovering over a sun symbol. The details can be updated in real-time or substantially real-time, such as updated in intervals ranging from about every 1 minute to about every 5 minutes, or up to about every 1 hour or more. This gives a user quick and real-time access to specifics about a patient's status and progression related to a particular survey response, thus potentially affecting personnel and resource decision making in real-time.

Figure 30:
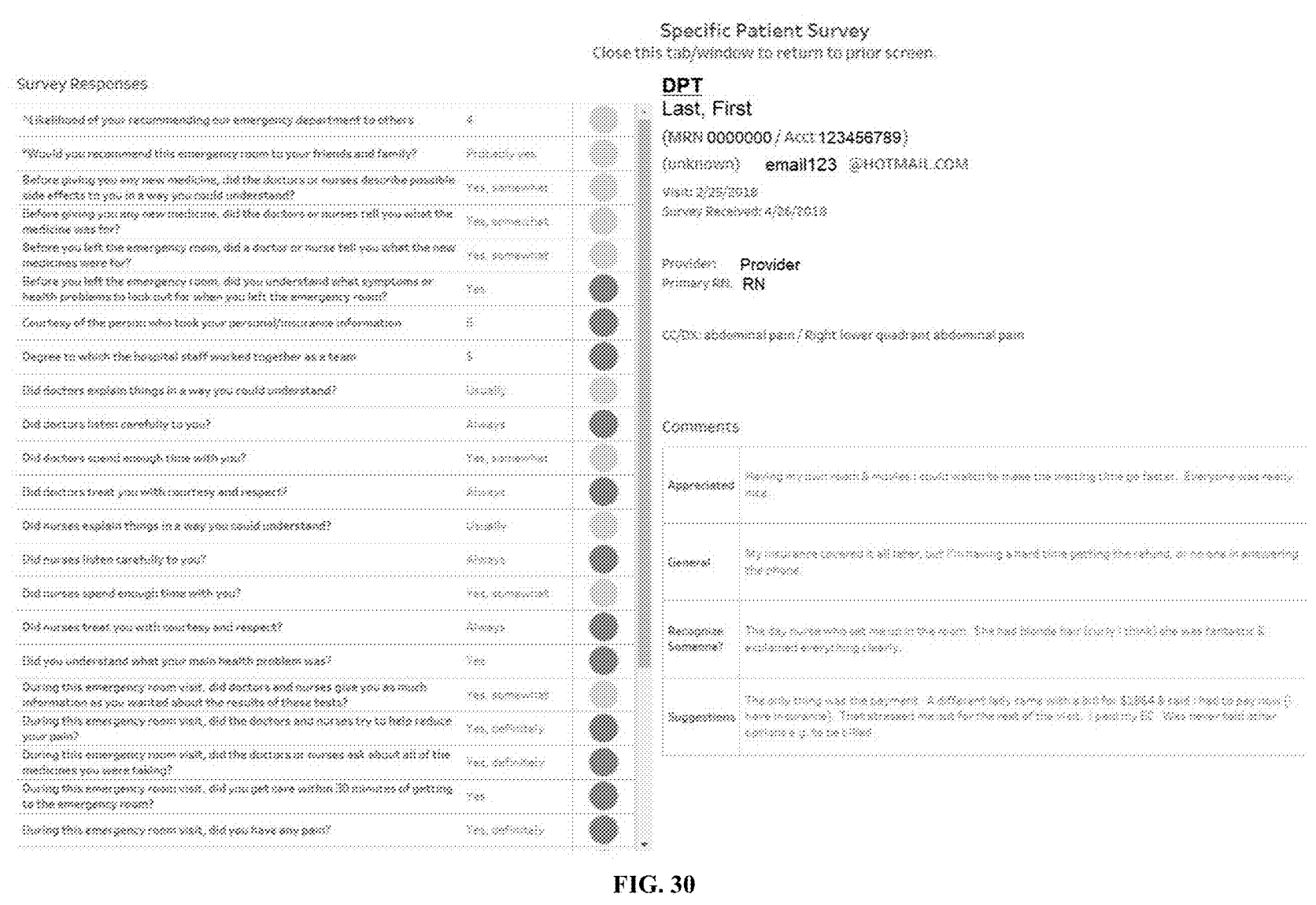

FIG. 30 illustrates a completed patient survey upon selecting a sun symbol corresponding to a patient from a comments section for real-time patient experience data according an embodiment of the present invention. The patient survey can include, e.g., color-coded indicia that facilitate quick and easy deduction of a patient's satisfaction with regards to each survey question. The survey can also include patient and health-care provider details, comments, and any other pertinent survey information. The comments can be updated in real-time or substantially real-time, such as updated in intervals ranging from about every 1 minute to about every 5 minutes, or up to about every 1 hour or more. This gives a user quick and real-time access to specifics about a patient's reasoning for particular survey response, thus potentially affecting personnel and resource decision making in real-time.

FIG. 31 illustrates real-time and historical patient survey statistics for a facility in communication with a RAD database according to an embodiment of the present invention. In an embodiment, survey question statistics at a specific site can be visualized, broken down by month. In an embodiment, the survey statistics can be represented in a color-coded grid according to a percentage rating based on survey responses. For example, a survey question can be coded red in a given month if survey responses averaged below, e.g., 50.0% for that month. In an embodiment, the color-coding is a color gradient from red for percentages below about 50.0% to dark green for percentages of about 100.0%.

The real-time and historical patient survey statistics can be updated in real-time or substantially real-time, such as updated in intervals ranging from about every 1 minute to about every 5 minutes, or up to about every 1 hour or more. This gives a user quick and real-time access to the performance through time of a particular facility with respect to each aspect of the patient surveys. This can potentially affect personnel and resource decision making in real-time.

Figure 32:
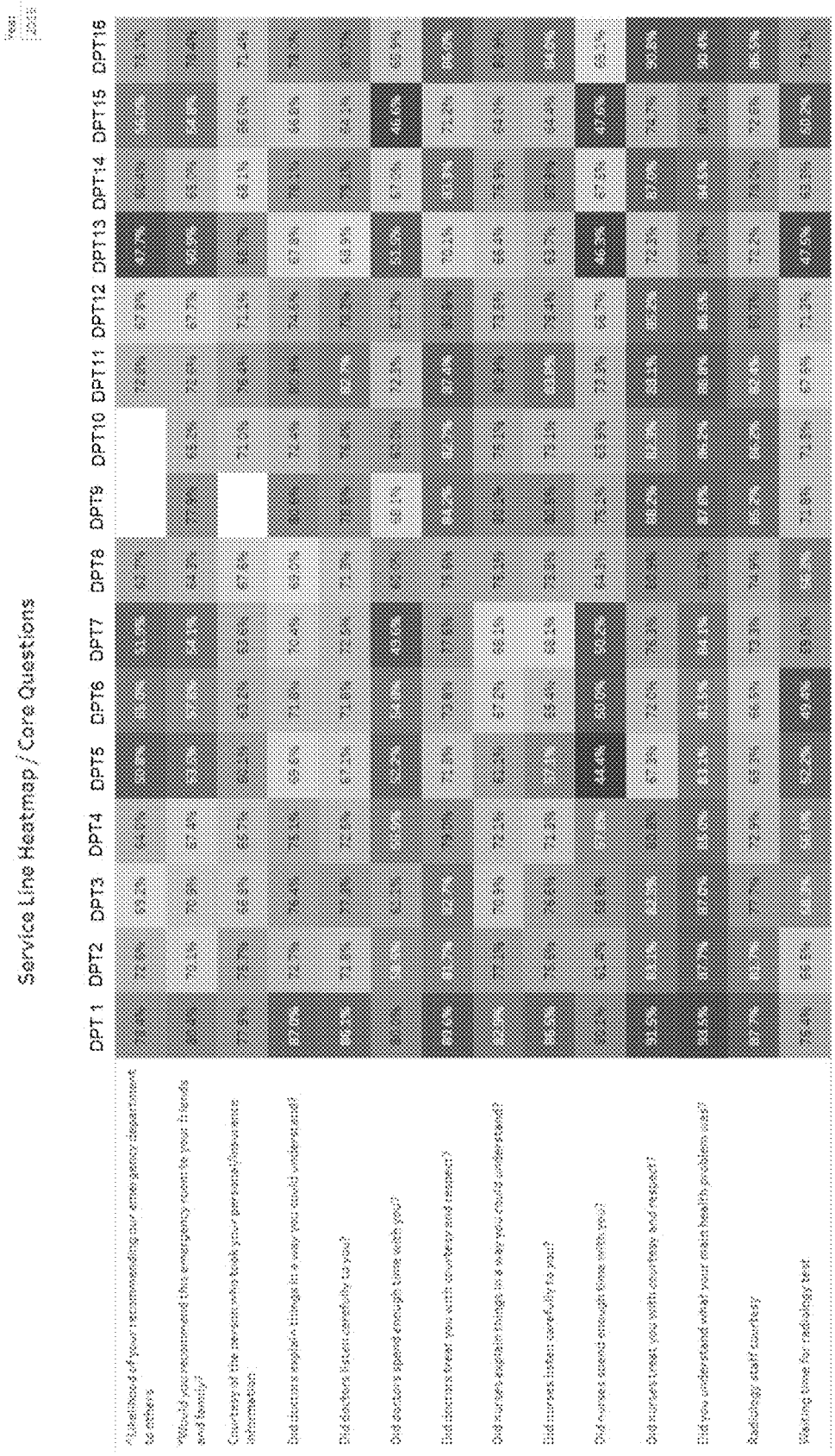

FIG. 32 illustrates real-time visualization of patient survey statistics for each survey question, broken down by department according to an embodiment of the present invention.

In an embodiment, real-time survey question statistics can be visualized, broken down in a grid by department and survey question. In an embodiment, the survey statistics can be represented in a color-coded grid according to a percentage rating based on survey responses. For example, a survey question can be coded red in a given department if survey responses are averaging below, e.g., 50.0% for that department.

In an embodiment, the color-coding is a color gradient from red for percentages below about 50.0% to dark green for percentages of about 100.0%. The real-time and historical patient survey statistics can be updated in real-time or substantially real-time, such as updated in intervals ranging from about every 1 minute to about every 5 minutes, or up to about every 1 hour or more. This gives a user quick and real-time access to the performance through time of a particular facility with respect to each aspect of the patient surveys. This can potentially affect personnel and resource decision making in real-time.

In an embodiment, the real-time statistics can be for a rolling period. For example, the statistics for each department can be represented for, e.g., the past 30 days, past 2 weeks, past week or past day, or any suitable time period for representing real-time performance of each department. In an embodiment, the rolling period can be user selectable to represent performance at varying time frames.

Figure 33:
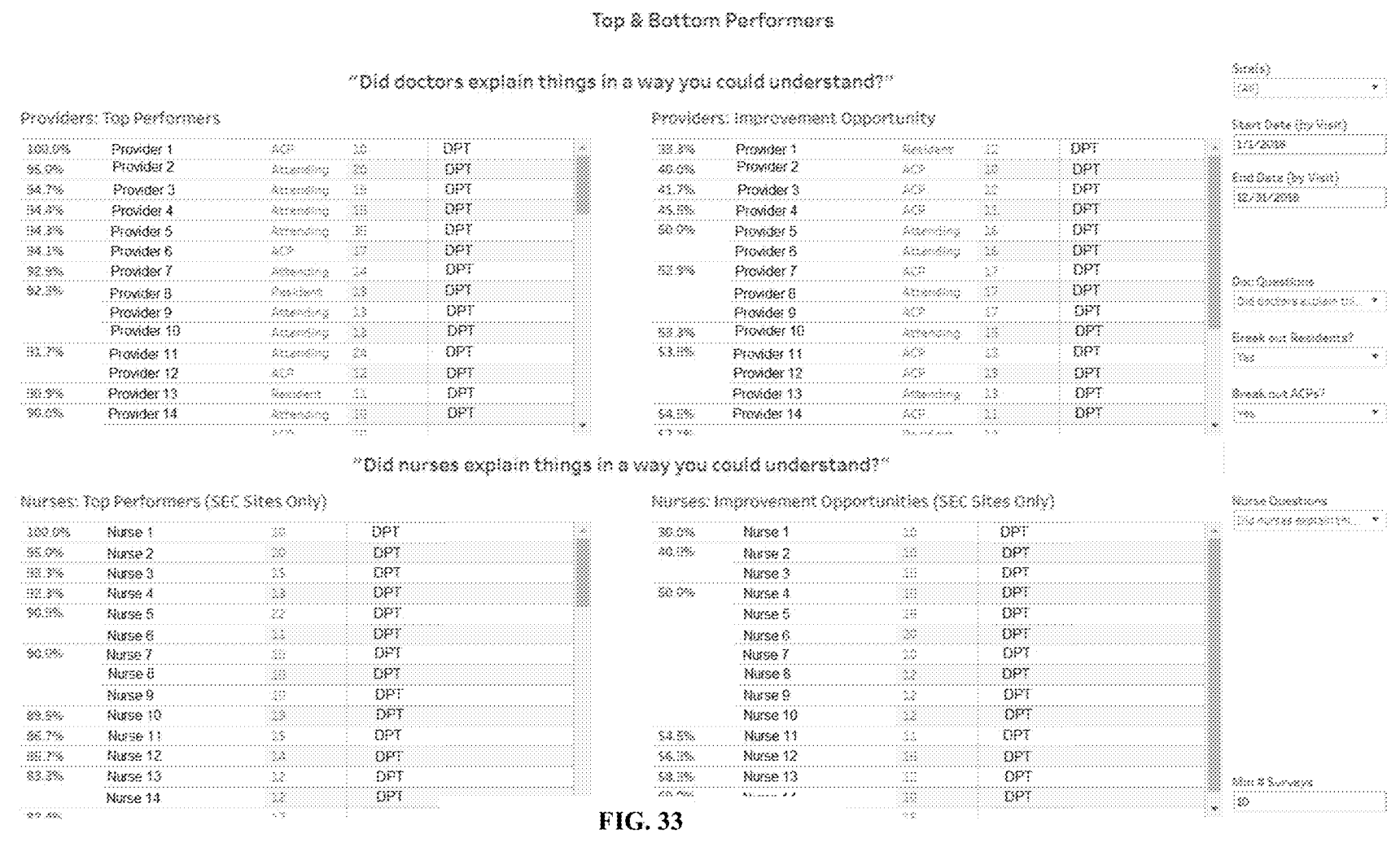

FIG. 33 illustrates employee performance rankings corresponding to patient survey questions according to an embodiment of the present invention. In an embodiment, best and worst performers can be ranked by site and/or service line.

The performance rankings can be updated in real-time or substantially real-time, such as updated in intervals ranging from about every 1 minute to about every 5 minutes, or up to about every 1 hour or more. This gives a user quick and real-time access to the performance through time of a particular facility with respect to each aspect of the patient surveys. This can potentially affect personnel and resource decision making in real-time according to personnel performance with respect to the patient experience.

Figure 34:
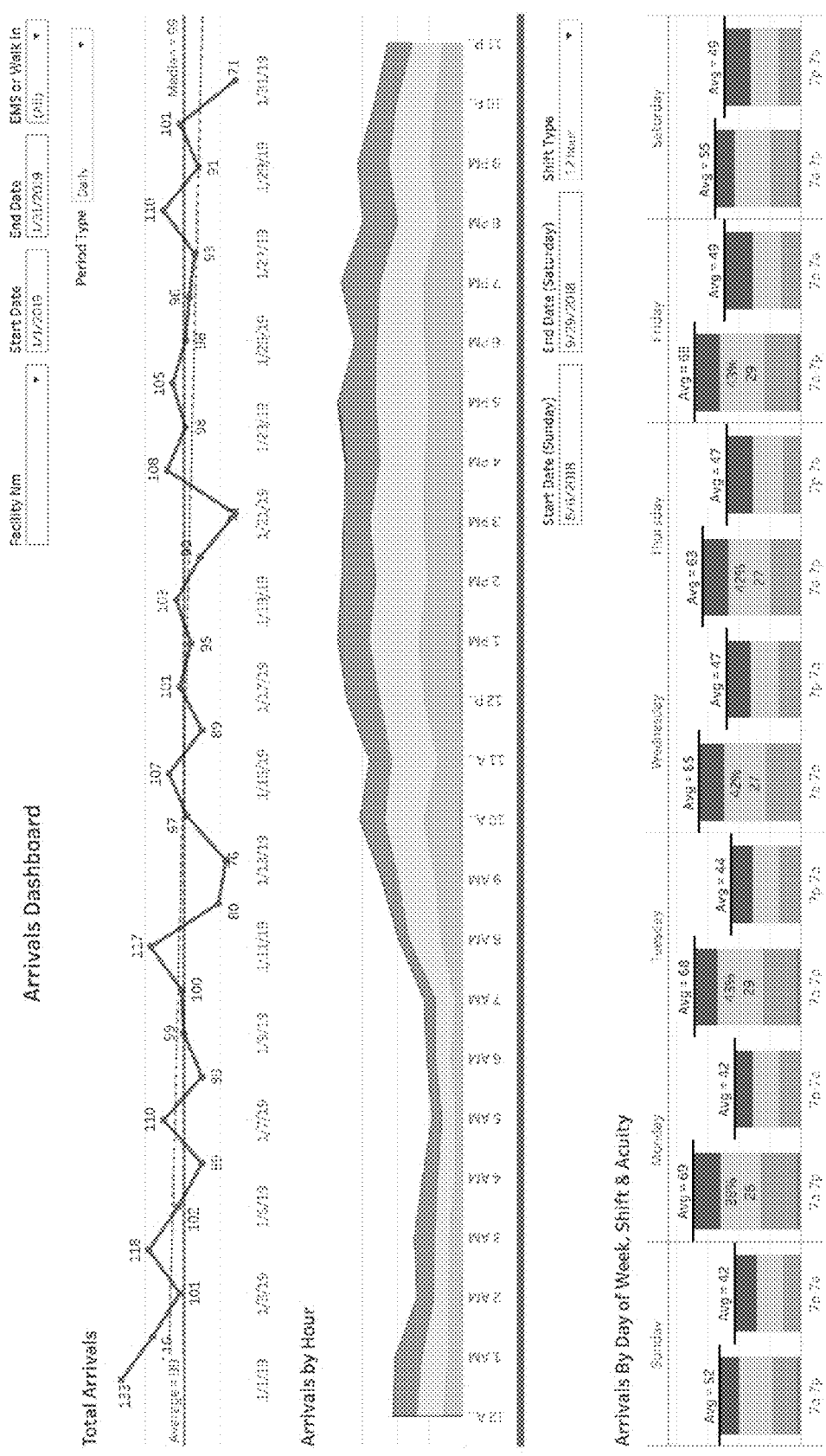

FIG. 34 illustrates a patient arrival dashboard for real-time and historical patient arrival information according to an embodiment of the present invention. The patient arrival information can be used to track workloads through time to easily deduce personnel and resource decision making using easily understand visual representations. The arrival information can be updated in real-time or substantially real-time, such as updated in intervals ranging from about every 1 minute to about every 5 minutes, or up to about every 1 hour or more.

Figure 35:
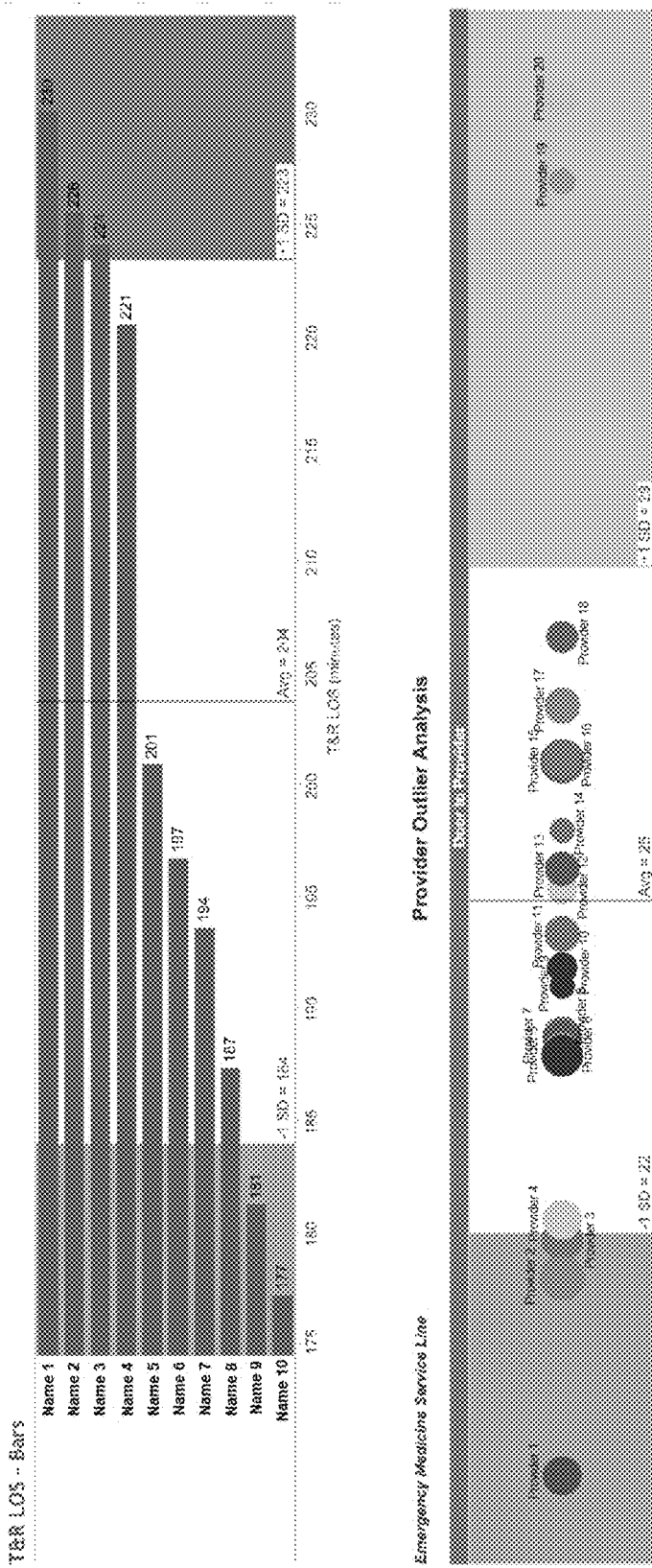

FIG. 35 illustrates real-time data analysis and visualization for at-a-glance determination of outliers according to an embodiment of the present invention. In an embodiment, the outlier analysis visualization can be performed for emergency medical service transport times, however other real-time data can be similarly visualized. In an embodiment, a visualization of provider outliers can be depicted to easily understand outside-the-norm patient care. For example, for patient wait time scenarios, an outlier could indicate that a provider took an uncommon amount of time to visit a patient, which may indicate, e.g., that the prior patient took longer than most of that provider's patient. This information can be easily interpreted from the visual representation to deduce either poor performance, or exigent circumstances with regards to the substandard care for a given patient. Such circumstances may affect evaluation of the provider, or it may indicate a need for additional personnel and resources for a corresponding department or service.

In an embodiment, the data analysis and visualization information can be updated in real-time or substantially real-time, such as updated in intervals ranging from about every 1 minute to about every 5 minutes, or up to about every 1 hour or more.

Figure 36:
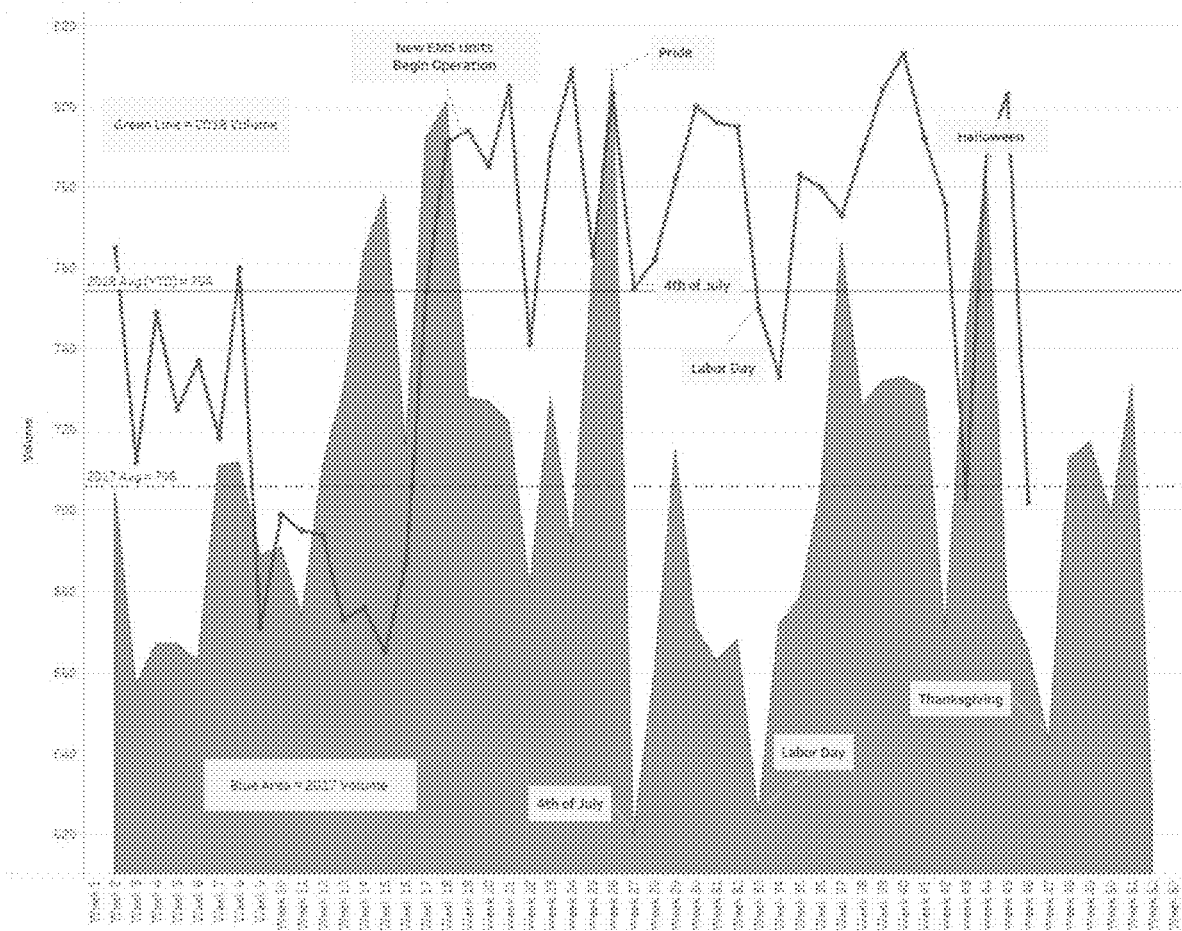

FIG. 36 illustrates real-time service volume data according to an embodiment of the present invention. In an embodiment, volume data from multiple time periods can be overlaid to compare volume trends across periods. In an embodiment, holidays and other significant events can be specified on the visualization of the volume data. Thus, relationships can be drawn between times of year and total patient volume. This information can influence personnel and resource management decisions.

Figure 37:
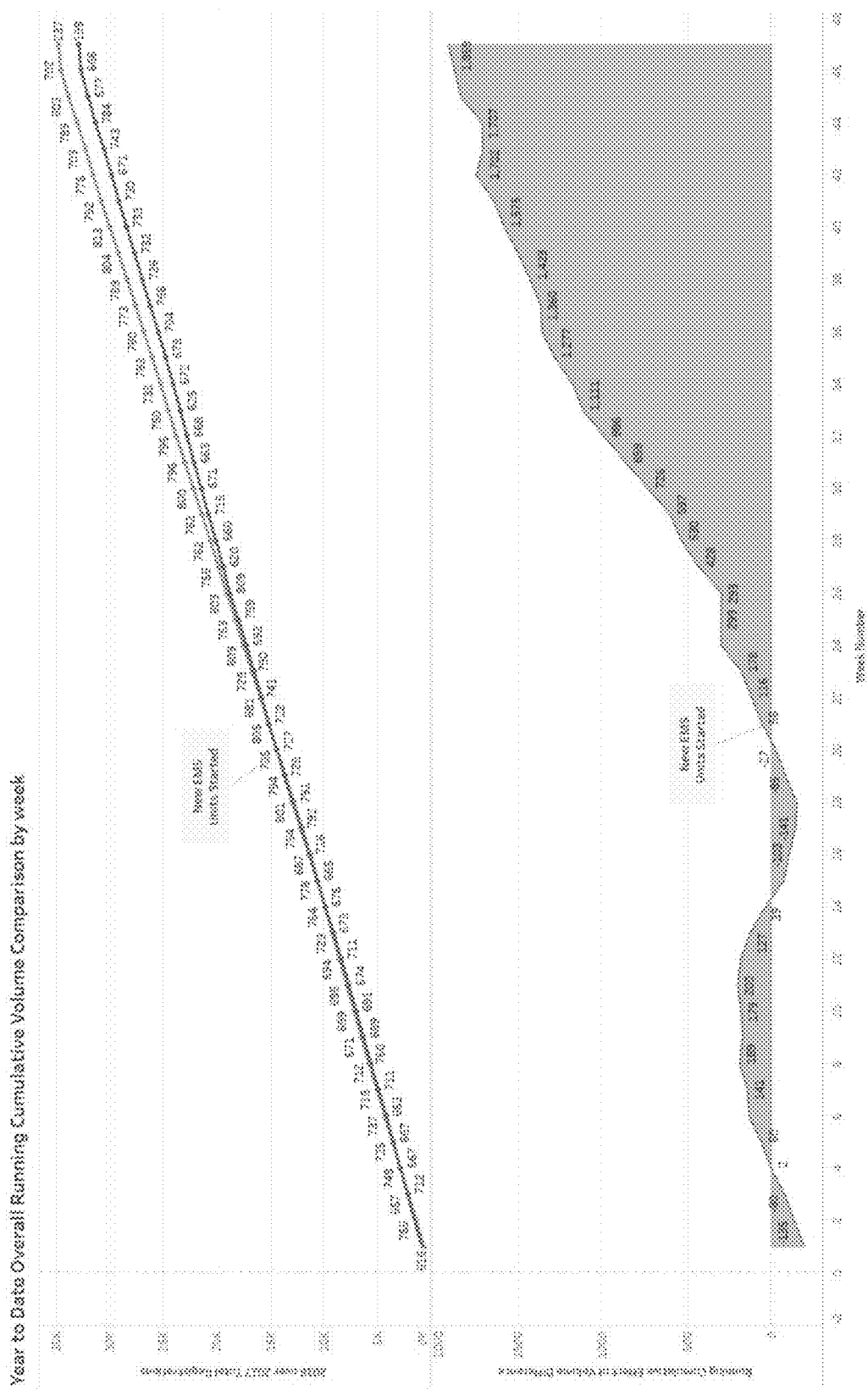

FIG. 37 illustrates real-time cumulative service volume data according to an embodiment of the present invention. In an embodiment, volume data from multiple time periods can be overlaid to compare cumulative volume trends across periods. In an embodiment, holidays and other significant events can be specified on the visualization of the volume data. In an embodiment, a running cumulative effect of volume differences between time periods can be displayed side-by-side with the cumulative volume for real-time impact analysis. Thus, relationships can be drawn between times of year and total patient volume. This information can influence personnel and resource management decisions.

Figure 38:
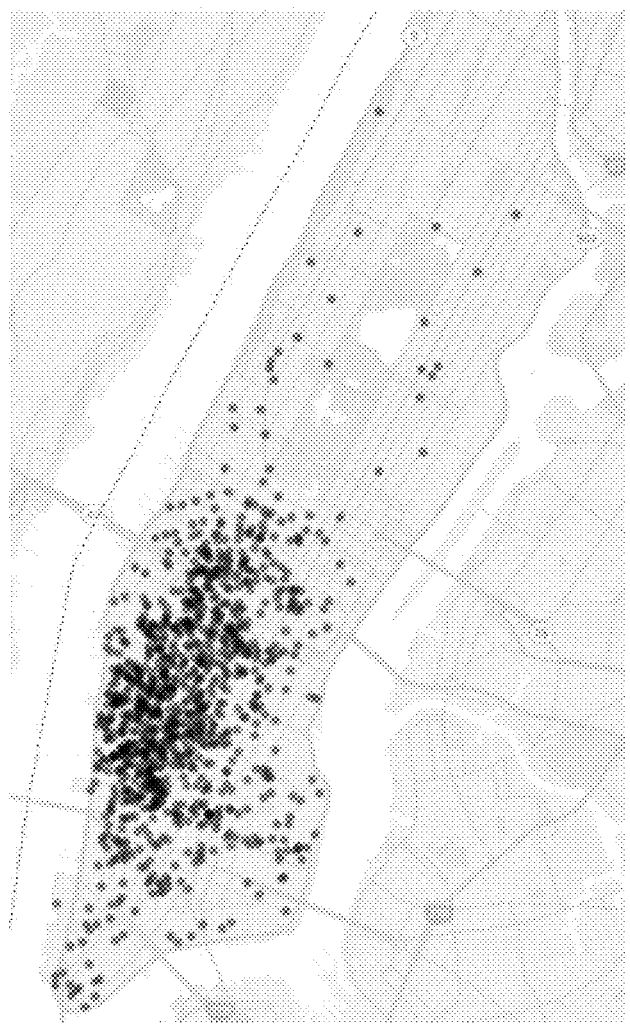

FIG. 38 illustrates a real-time hot-spot map according to an embodiment of the present invention. In an embodiment, real-time data can be utilized to generate service volume hot-spots by geographic region, depicted on a map for at-a-glance geographic service volume analysis. Thus, relationships can be drawn between location and total patient volume. This information can influence personnel and resource management decisions, including ambulance routing.

Figure 39:
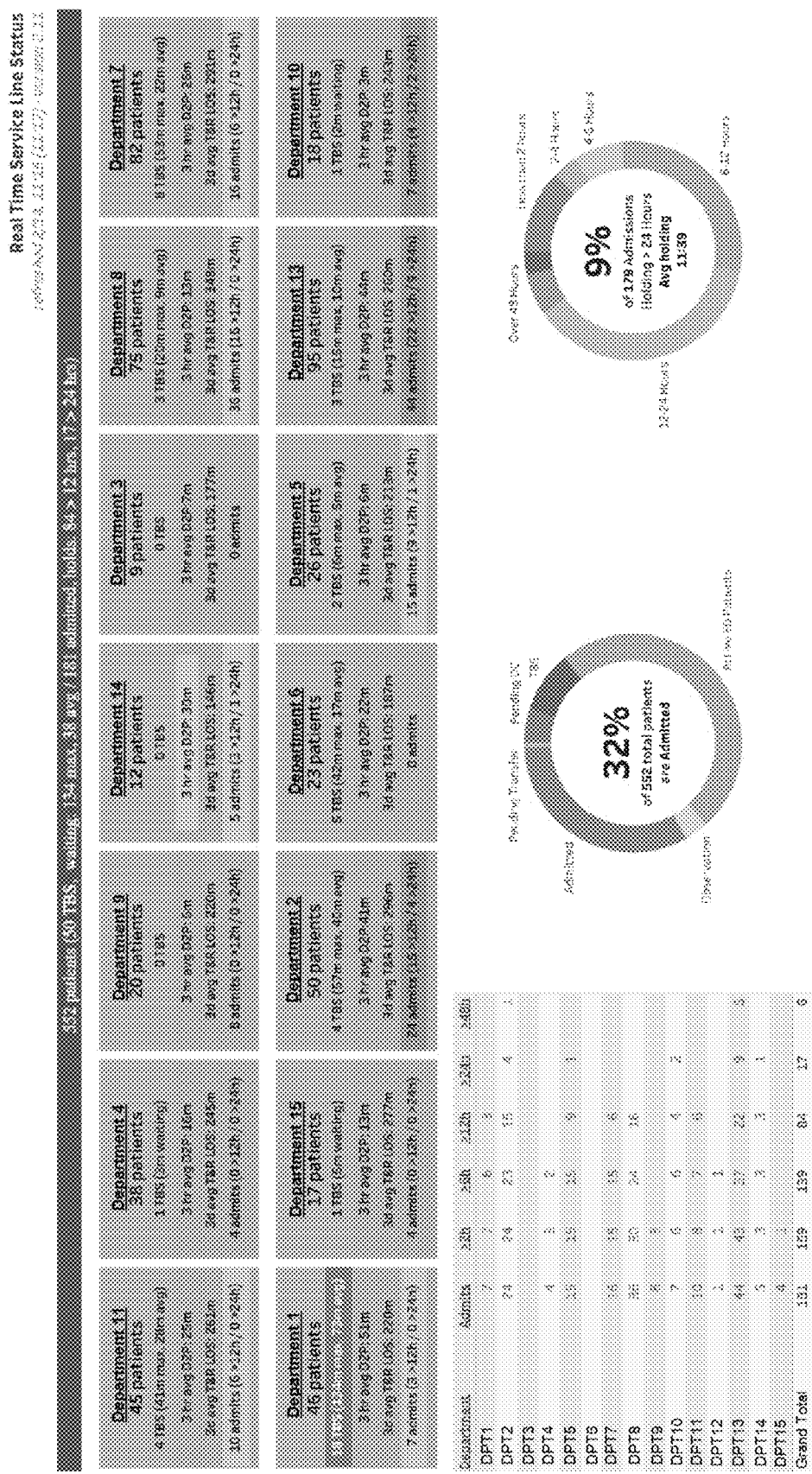

FIG. 39 illustrates real-time multi-facility service metrics according to an embodiment of the present invention. In an embodiment, data queries to real-time databases of each facility can provide service metrics compiled and analyzed to display visualizations across a facility network with real-time service status and metrics.

Figure 40:
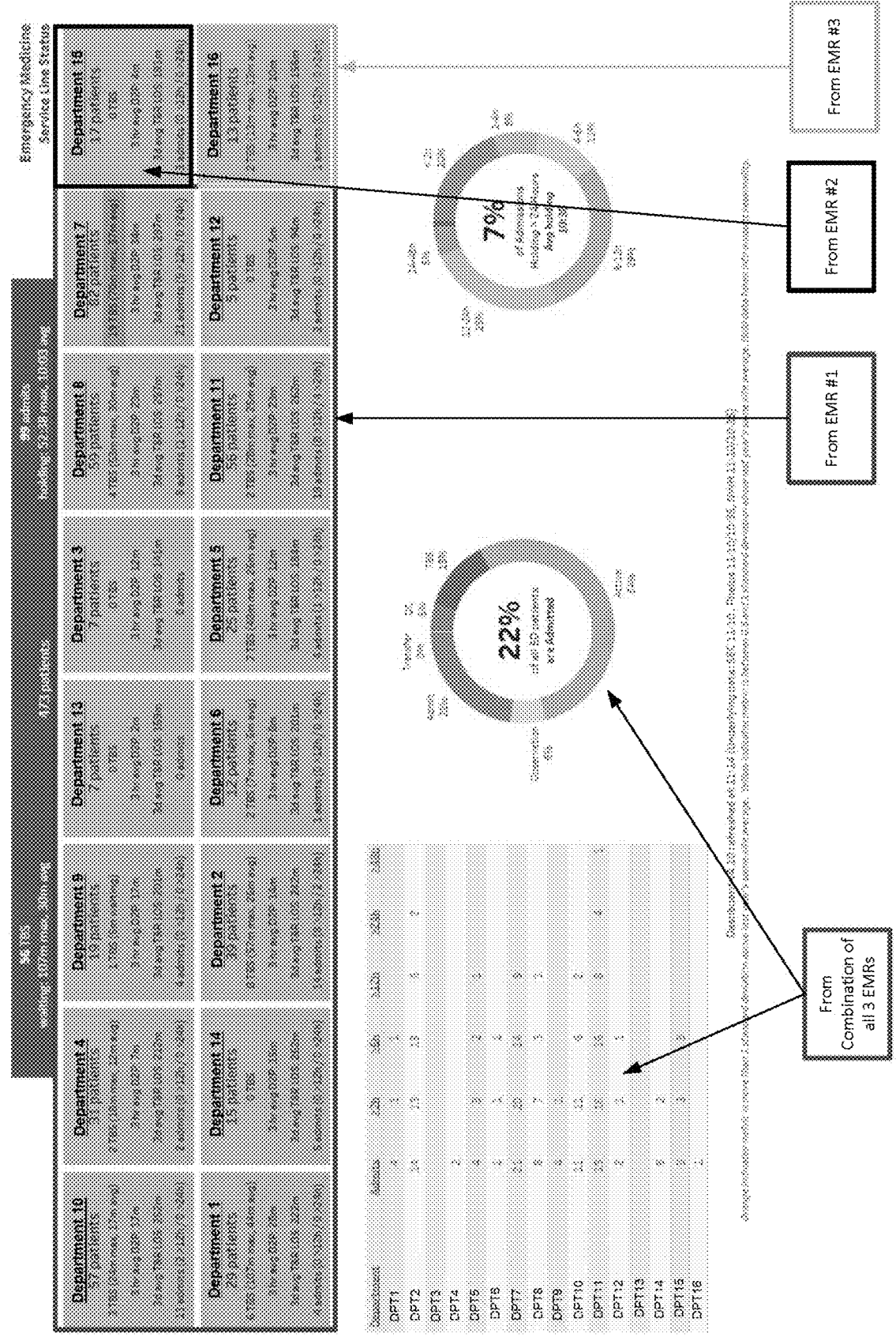

FIG. 40 illustrates real-time multi-facility service metrics according to an embodiment of the present invention. In an embodiment, data queries to real-time databases of each facility can provide service metrics for individual facilities as well as combined real-time service status and metrics. Thus, personnel and resource deficiencies and surpluses can be quickly and easily deduced with a glance according to each department's real-time status. This information can influence personnel and resource management decisions, including allocation across the departments.

In an embodiment, the department statuses can be updated in real-time or substantially real-time, such as updated in intervals ranging from about every 1 minute to about every 5 minutes, or up to about every 1 hour or more.

In an embodiment, this RAD tool serves to provide a centralized view of the current status of the entire health system's 16 emergency departments. The tool uses current and historical data to provide alerting when any of the departmental metrics are currently out of range based on algorithmically processed calculations. This alerting helps senior level executives to potentially change resource allocation between departments based on performance and need. This information was not previously available in any fashion.

In an embodiment, multiple electronic medical records (EMR) vendors collect real-time data about clinical medical records for patients and patient visits. In an embodiment, a database layer of the RAD tool runs queries every 5 minutes to collect clinical medical records for patients and patient visits from each EMR vendor. Each vendor can hold data in a separate security domain. In an embodiment, the database layer can also run queries every hour for recent historical visit data from each vendor. In an embodiment, the database layer normalizing collected data across the each vendor's database structures to form a central table of real-time data from all vendors.

In an embodiment, an algorithmic processing layer analyzes each metric and flags each metric according to a level of importance. For example, in an embodiment, each performance metric is compared against same department, seasonally, day of week, and hour of day adjusted historical norms. Each metric is then flagged as either within limit, at warning level or at problem level. In an embodiment, the flags can be determined according to statistic comparison. For example, the within limit flag can corresponding to a less than 0.5 standard deviations from the historical mean, while the warning level corresponding to between 0.5 and 1 standard deviations, and a problem level corresponding to above 1 standard deviation.

In an embodiment, the real-time multi-facility service metrics can be generated and visualized by a visualization layer. In an embodiment, the visualization layer opens a connection to the normalized data tables created in each of the three security domains of the vendors. Additional calculations are performed to summarize the data and to support creation of tabular and graphical representations of key data elements. Graphical representations of each department and its key metrics are displayed with color coding to represent the flagging (within limit, warning level, or problem level) determined in the algorithmic processing layer.

In an embodiment, the dashboard is automatically refreshed to reflect the most up to date data available (every 3-5 minutes). Furthermore, in an embodiment, the visualization layer automatically detects if the database layer or algorithmic processing layer's output is not current and warns the user (if it is only mildly delayed) or displays an "unavailable" message if the output is significantly delayed. This helps the user to not make decisions based off of stale data.

Figure 41:
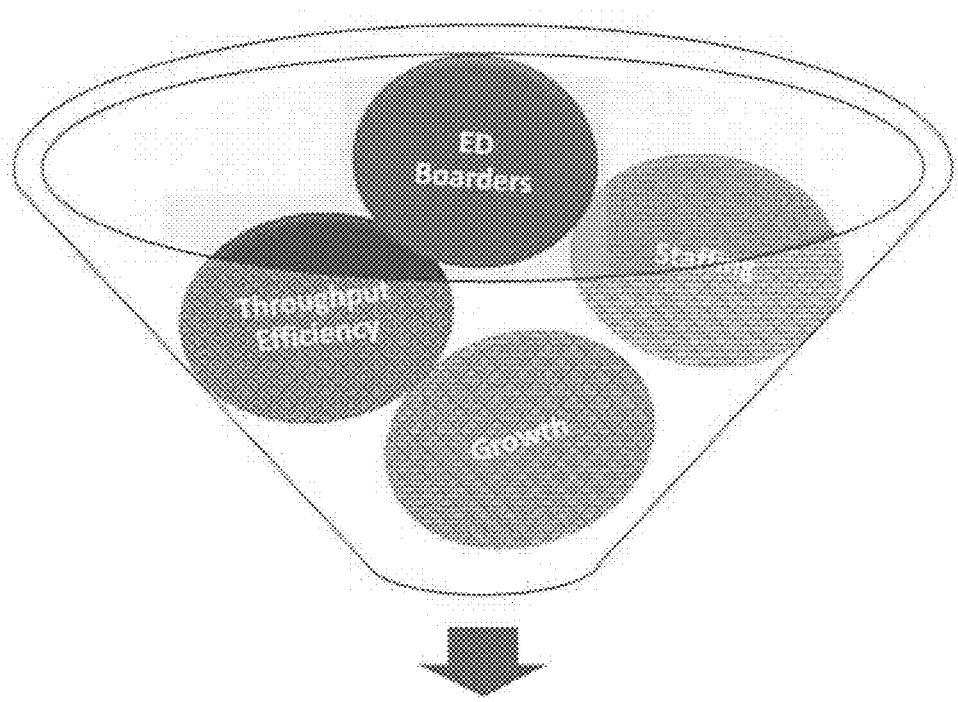

FIG. 41 illustrates challenges to emergency departments in medical facilities. Emergency departments are often overcrowded and over capacity, choking growth, efficiency, staffing and boarders with too few resources to address these demands.

Figure 42:
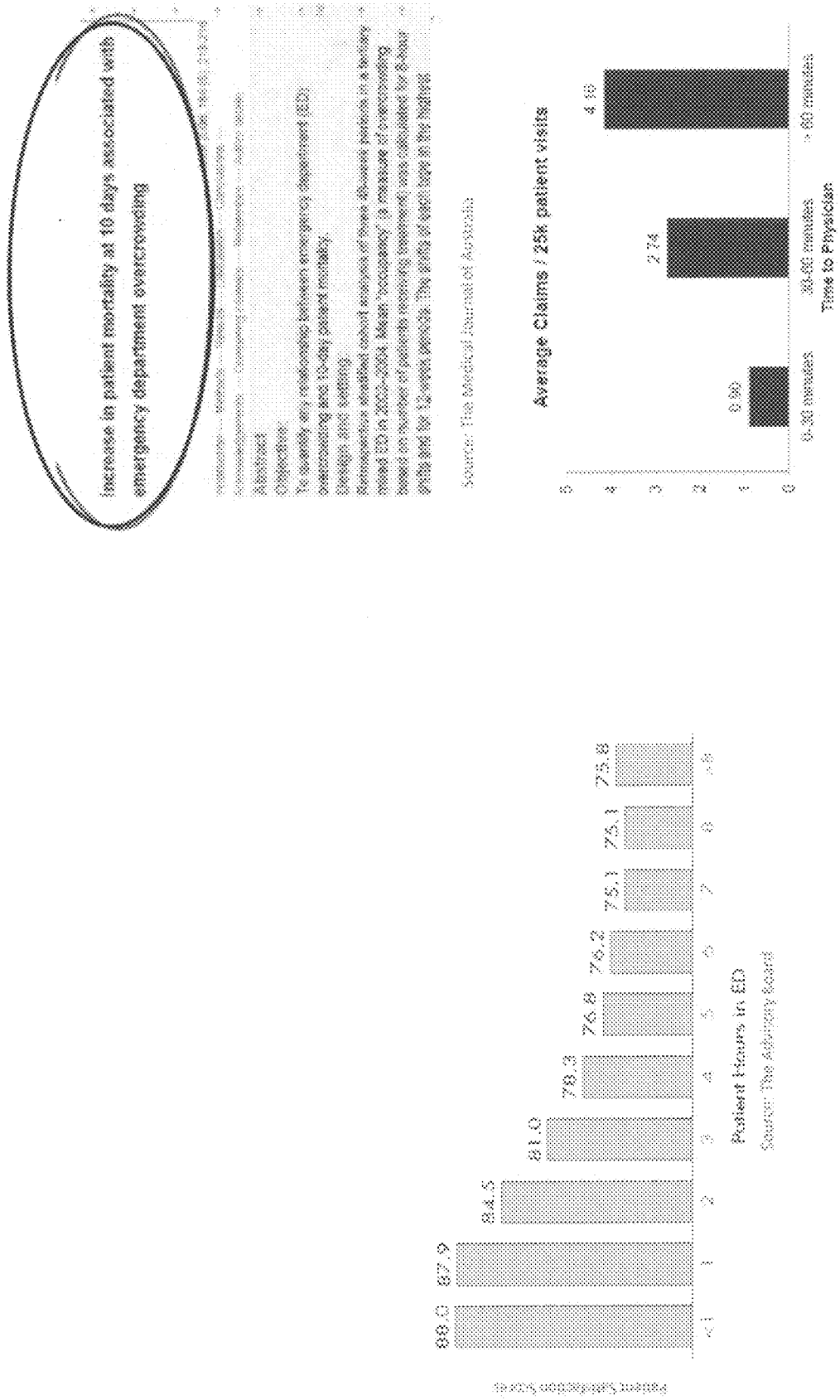

FIG. 42 illustrates the effect of length of stay on positive health outcomes. Emergency department (ED) length of stay (LOS) plays a role in every patient encounter. ED LOS affects: patient satisfaction, quality measures—morality, patients that left-without-being-evaluated (LWOBEs), medical errors, ED capacity, inpatient length of stay, finances—LWOBEs, diversion time, risk of malpractice.

FIG. 43 illustrates ED overcrowding consequences, including increased wait to receive care, increased LOS, increased walkouts and LWOBEs, decreased quality of care, increased mortality and ambulance diversions.

Figure 44:
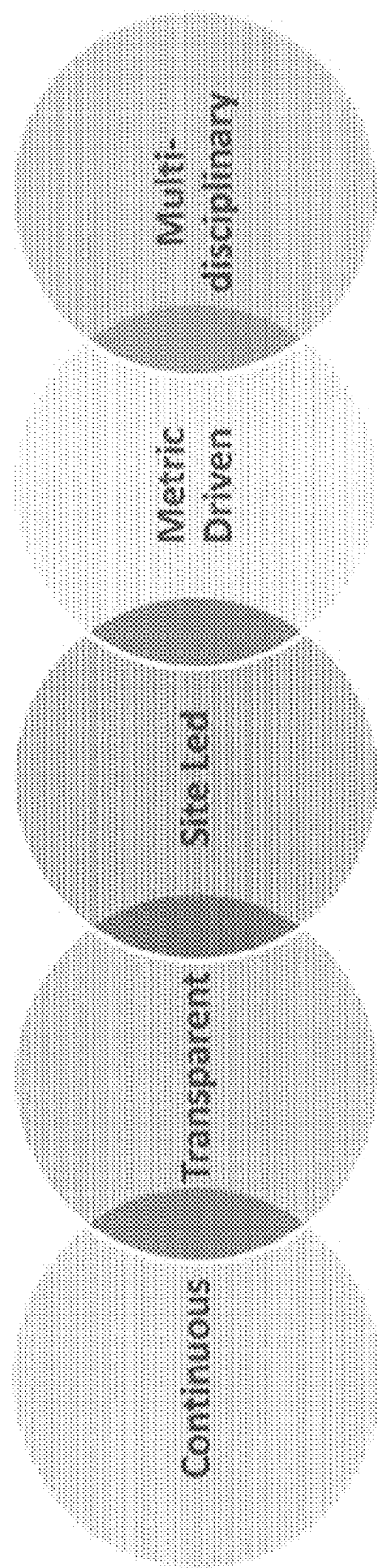

FIG. 44 illustrates a framework of process improvement according to an embodiment of the present invention. Create a culture in all departments of continuous introspective review and enhancement using improved scientific techniques to match diverse operations to provide the best care and treatment of patients and family members.

FIG. 45 illustrates a sample of emergency medicine data metrics according to an embodiment of the present invention. In an embodiment, the depicted metrics are only a portion of over 200 metrics captured at each emergency medicine facility. The metrics can be monitored to match patient needs to the right resources. However, in a raw form, such uses can be difficult and inefficient.

Figure 46:
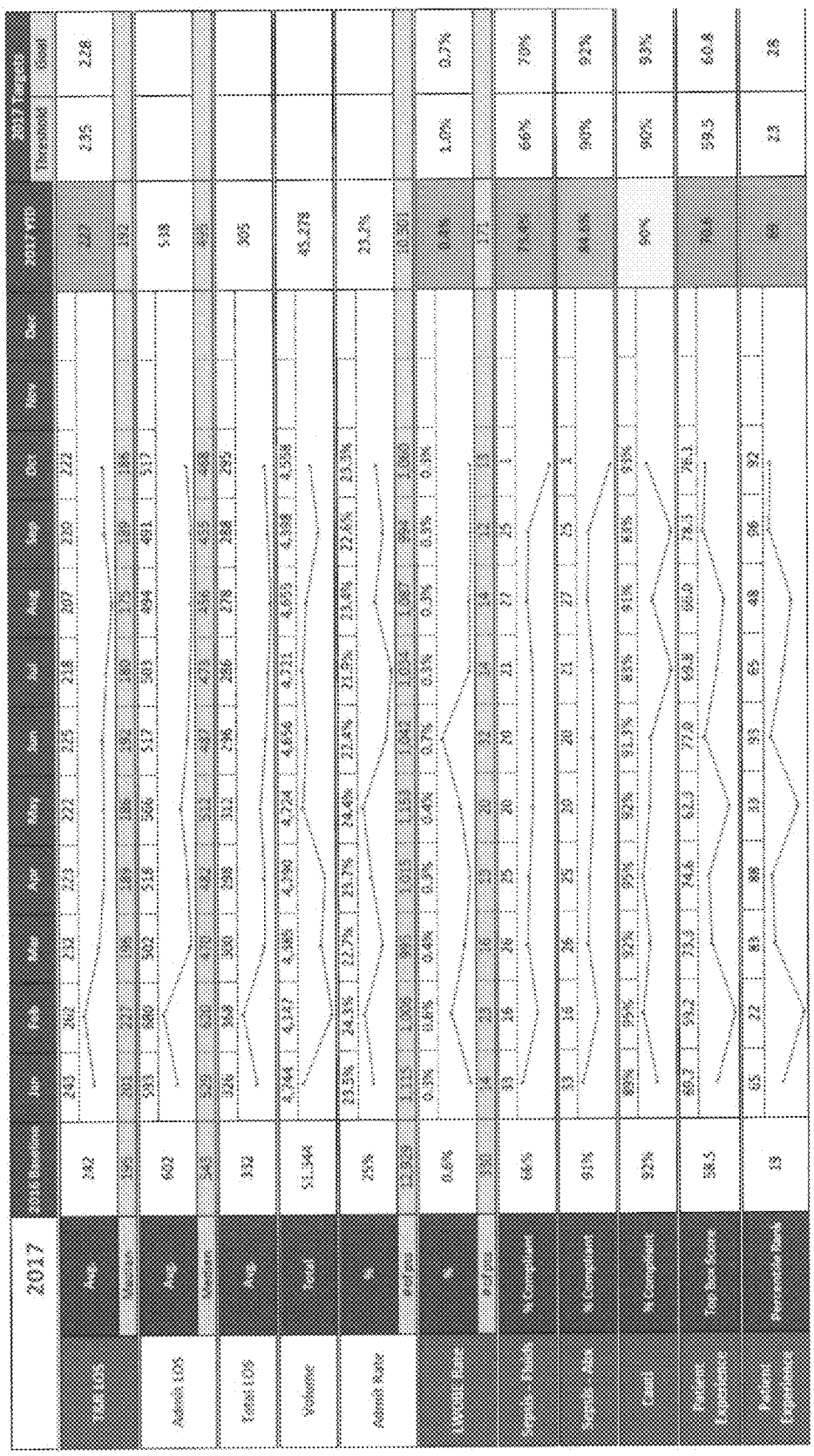

FIG. 46 illustrates a static monthly dashboard of patient statistics according to an embodiment of the present invention.

Figure 47:
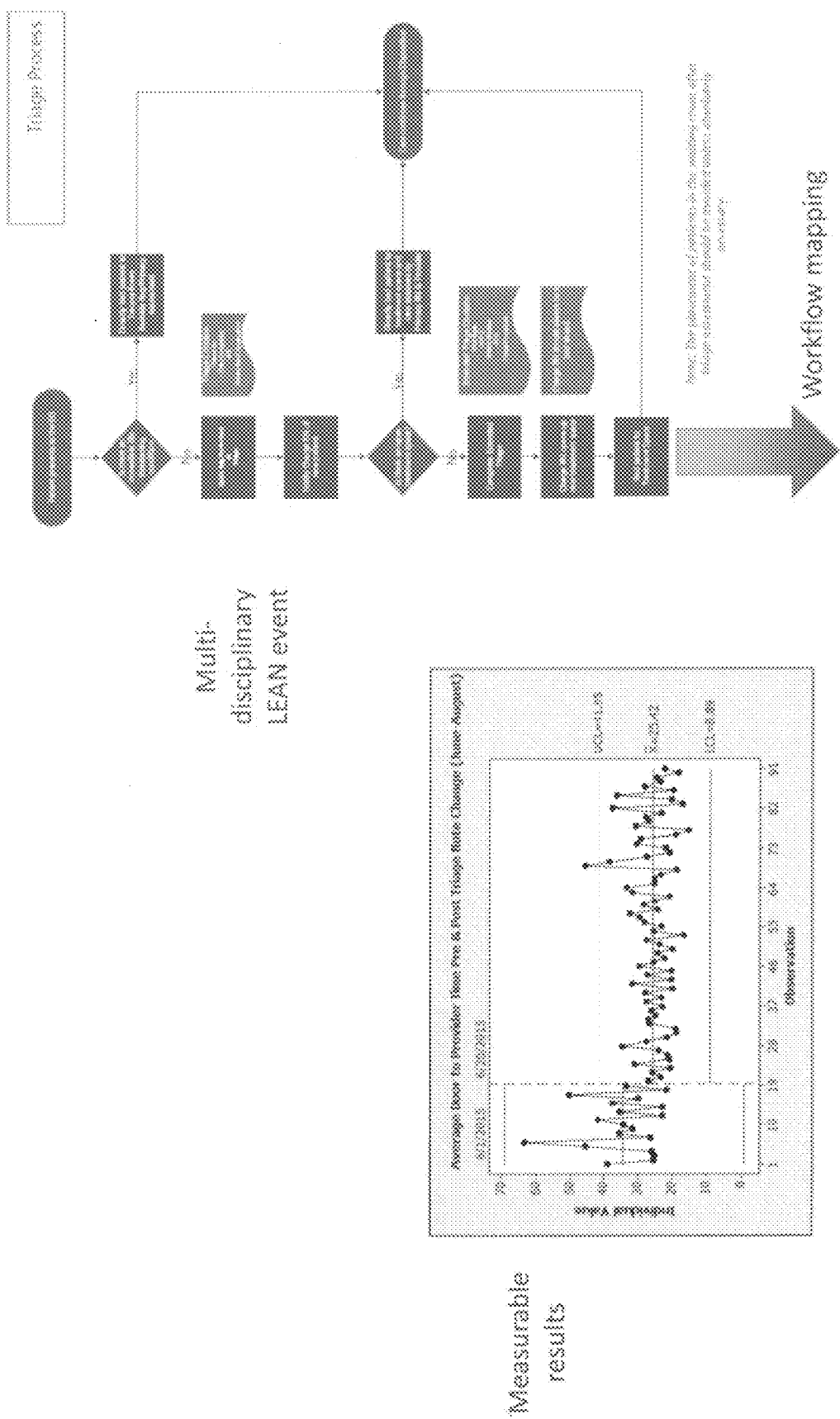

FIG. 47 illustrates a workflow process for decreasing triage times according to a multi-disciplinary LEAN event according to an embodiment of the present invention. The effects of decreasing door to provider triage to less than 30 minutes shows positive results.

Figure 48:
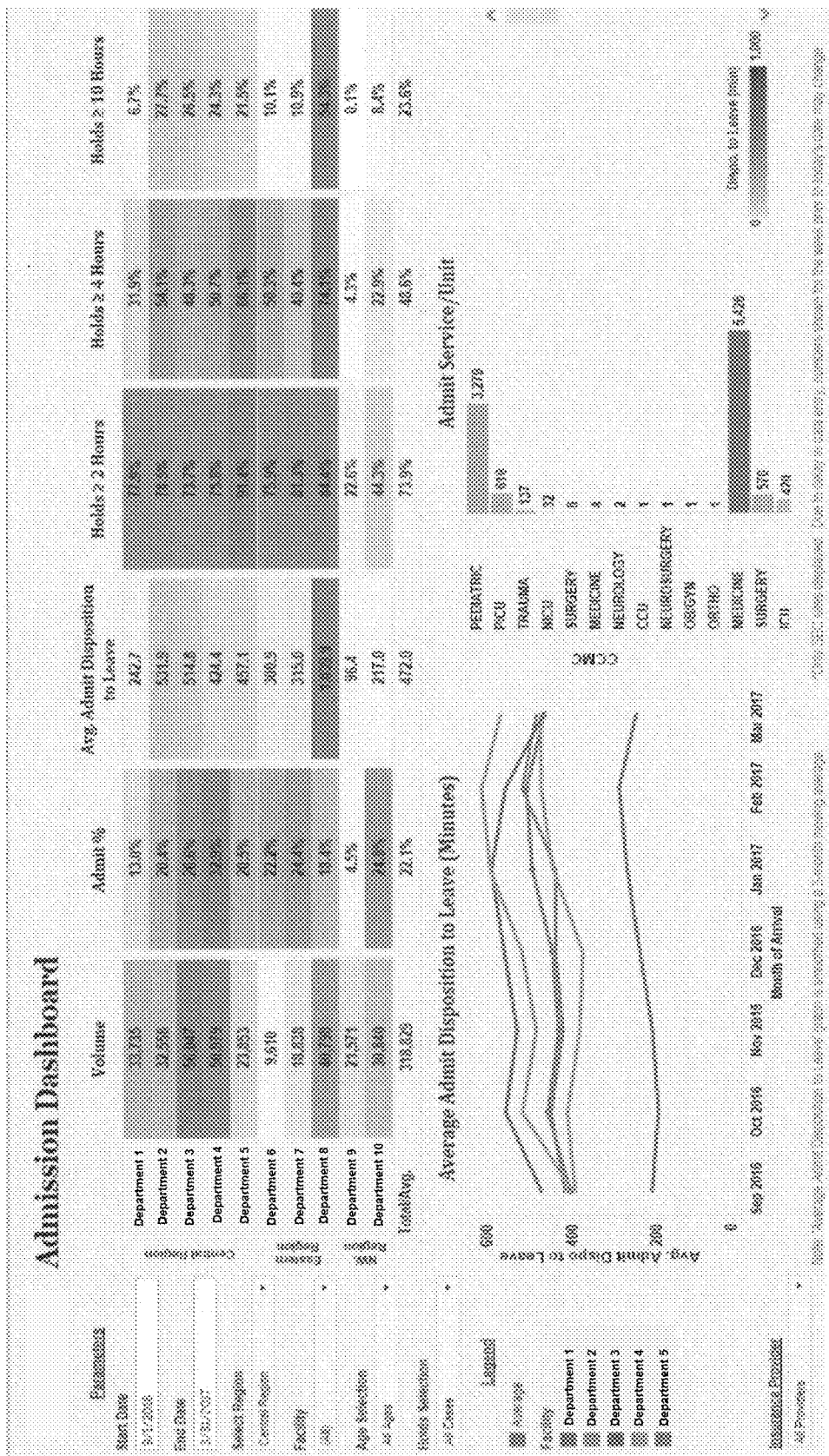

FIG. 48 illustrates a real-time dashboard of patient admission statistics according to an embodiment of the present invention. In an embodiment, statistics can be broken down by department, service or care provided, holds, time from admission to leave, and other metrics pertinent to the quality and efficiency of care. Thus, personnel and resource requirements can be quickly and easily deduced with a glance according to each department's real-time volume data. This information can influence personnel and resource management decisions, including allocation across the departments.

In an embodiment, the department statuses can be updated in real-time or substantially real-time, such as updated in intervals ranging from about every 1 minute to about every 5 minutes, or up to about every 1 hour or more.

Figure 49:
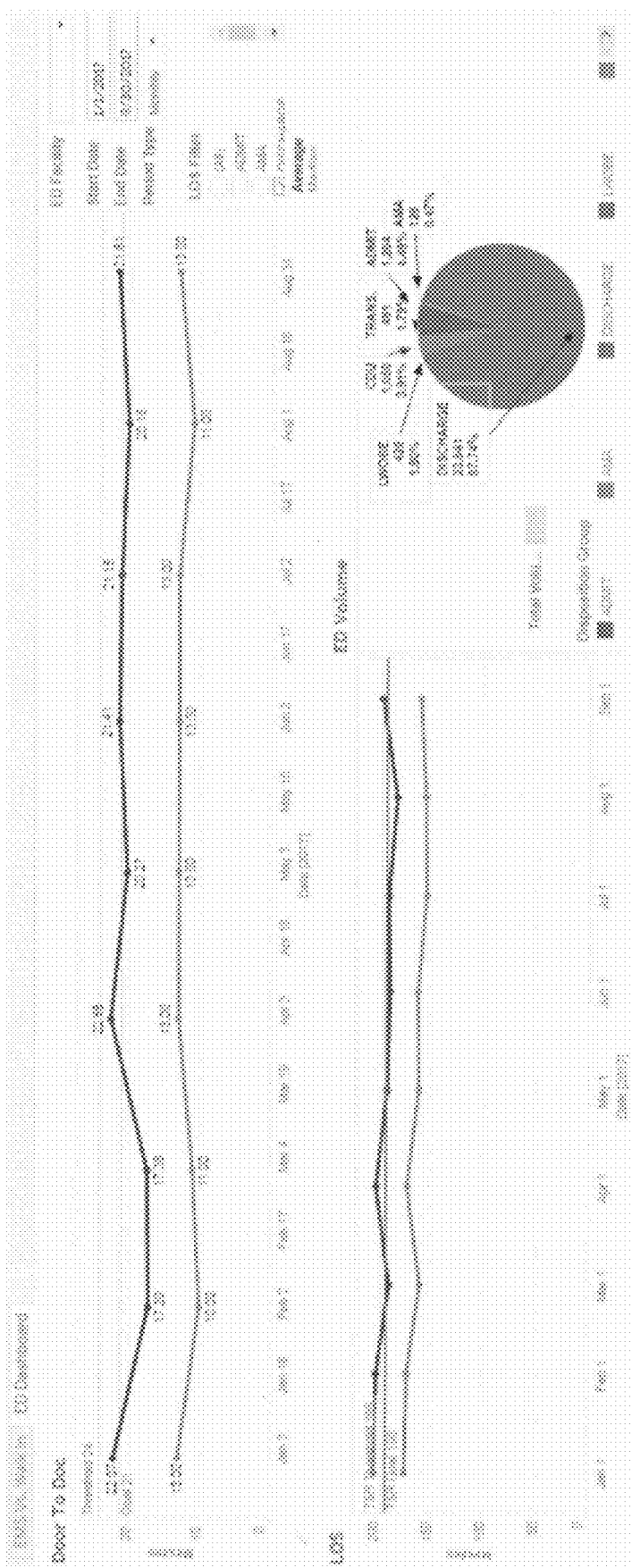

FIG. 49 illustrates a dynamic dashboard for aggregate patient disposition statistics. In an embodiment, the dashboard provides data to visualize opportunities for operational improvements (T&R LOS) and prioritize sites that need more assistance from the Clinical Operations Team. The dashboards are dynamic allowing the sites control and transparency over their data. In an embodiment, the dynamic dashboard for aggregate patient disposition statistics can be updated in real-time or substantially real-time, such as updated in intervals ranging from about every 1 minute to about every 5 minutes, or up to about every 1 hour or more. In an embodiment, the dynamic dashboard is updated, e.g., once per day.

FIG. 50 illustrates a method of scoring nurse workloads using an algorithmic processing layer according to an embodiment of the present invention.

Figure 51:
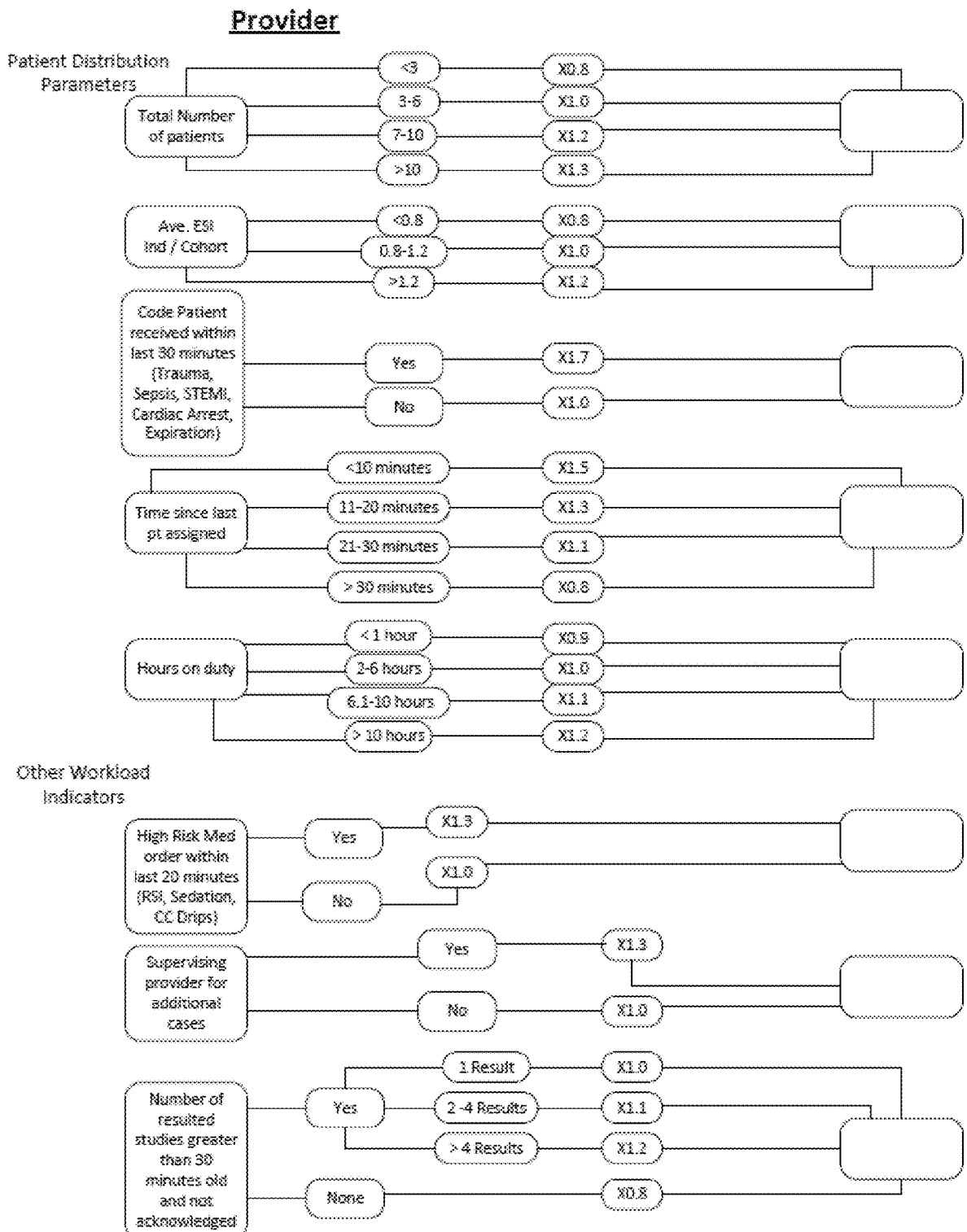

FIG. 51 illustrates a method of scoring provider workloads using an algorithmic processing layer according to an embodiment of the present invention.

In an embodiment, ESI scores, both independent and cohort, can be utilized to generate a provider schedule score that quantifiably represents a provider schedule prioritization for improved scheduling of rounds and orders. A provider can include, e.g., a doctor, a physician's assistant, a surgeon, a laboratory technician, or other service provider. The provider schedule score can also include workload balancing factors such as, e.g., the current task list of the individual staff member, the importance or time demand of their specific task, overall patient load, as well as related metrics including timing and types of orders tasked to providers. Accordingly, providers with the most demanding workload can be quickly surfaced to determine, with actionable data, how to shift schedules, rounds and orders amongst provider staff. In an embodiment, the provider schedule score is constantly updating and leading to an on-deck list to guide the Charge RN or Care Traffic Controller to distribute the work more equitably and in a manner that will result in improved efficiency, experience, and safety in real-time.

As illustrated in FIGS. 50 and 51, the capacity of a provider or nurse is not assessed simply by the number of patients for whom they are caring. Rather, there are multiple variables specific to each patient that collectively need to be considered to truly understand a staff member's current, real-time workload and capacity, while making decisions related to distribution of incoming patients that will match resources as needed.

RAD assesses the level of workload, and capacity, of every clinician and nurse in the department at the exact moment additional demand (e.g., new patients, staff departures both planned and unplanned) enters the system. The determination is based on an algorithm working behind the scenes, which takes multiple data elements and applies a weighted score to that provider or nurse's individual workload at that moment. That score is determined by data that represents patient acuity (ex. ESI score, code status, use of critical care medications), resource needs (ex. ESI score, incomplete nursing interventions and orders) and other factors that represent higher demand moments in a patient's care.

For each factor, RAD has been assigned situational (quantifiable) levels with an associated coefficient that the tool will use to calculate the current workload of every staff member (physician, physician's Assistant, nurse practitioner and nurse) currently in the department and suggest which clinician is the most appropriate to match with a particular patient (e.g., a new patient).

The ability to achieve this calculation is at least in part what makes RAD more advanced than a human brain and therefore, capable of performing task beyond the capabilities of humans. RAD takes into account the slight variations in workload caused by the clinical acuity, needs of each patient, and operational realities, and then compiles them into a single score.

Emergency departments can assign patients in a "round robin" fashion to facilitate quick and effective schedule. Alternatively, more logic can be applied to balance the work simply use the triage category. However, even a resource-driven triage system, such as the Emergency Severity Index (ESI) system, is based on predicted resource needs after only a cursory triage evaluation. According to an embodiment, to improve upon workload balancing and schedule, ESI scores can be employed as a component of a scoring algorithm, such as the scoring algorithm described above in the algorithmic processing layer, to facilitate improving workload balancing and scheduling.

In an embodiment, ESI scores, both independent and cohort, can be utilized to generate a nursing schedule score that quantifiably represents a nursing schedule prioritization for improved scheduling of rounds and orders. The nursing schedule score can also include workload balancing factors such as, e.g., the current task list of the individual staff member, the importance or time demand of their specific task, overall patient load, as well as related metrics including timing and types of orders tasked to nurses. Accordingly, nurses with the most demanding workload can be quickly surfaced to determine, with actionable data, how to shift schedules, rounds and orders amongst nursing staff. In an embodiment, the nursing schedule score is constantly updating and leading to an on-deck list to guide the Charge RN or Care Traffic Controller to distribute the work more equitably and in a manner that will result in improved efficiency, experience, and safety in real-time.

At least some aspects of the present disclosure will now be described with reference to the following numbered clauses.

1. A system, comprising:
   a database layer that is at least configured to:
   i) query patient-related raw data from a plurality of data tables of a plurality of distinct data collection services having the plurality of distinct service specific data formats, wherein the patient-related raw data is related to a plurality of patients being serviced at a healthcare facility,
   ii) normalize the patient-related raw data with respect to the plurality of distinct service specific data formats to produce common format normalized patient-related data, and
   iii) store the common format normalized patient-related data;
   an algorithmic processing layer that is at least configured to:
   i) analyze, in real-time, the common format normalized patient-related data for the plurality of patients based on a plurality of patient-related data metrics, a plurality of healthcare facility-related data metrics, or both, to determine a plurality of patient-related data points for the plurality of patients, wherein each patient-related data point is associated with a respective threshold condition and a respective ranking score;

ii) rank, in real-time, for the plurality of patients, the plurality of patient-related data points, based on each respective threshold condition and each respective ranking score to determine a priority of each patient-related data point; and iii) generate, in real-time, based on the priority of each patient-related data point of the patient-related data points, at least one actionable medical directive related to at least one patient of the plurality of patients, wherein the at least one actionable medical directive is configured to cause at least one real-time operational change in the way that the healthcare facility services the at least one patient of the plurality of patients; and a visualization layer that is at least configured to cause presenting, in real-time, on a mobile computing device, the at least one actionable medical directive related to the at least one patient of the plurality of patients.

2. A method, comprising:

obtaining, by one or more processors, patient-related raw data from a plurality of data tables of a plurality of distinct data collection services having the plurality of distinct service specific data formats, wherein the patient-related raw data is related to a plurality of patients being serviced at a healthcare facility;

normalizing, by the one or more processors, the patient-related raw data with respect to the plurality of distinct service specific data formats to produce common format normalized patient-related data;

storing, by the one or more processors, the common format normalized patient-related data in at least one database;

analyzing, in real-time, by the one or more processors, the common format normalized patient-related data for the plurality of patients based on a plurality of patient-related data metrics, a plurality of healthcare facility-related data metrics, or both, to determine a plurality of patient-related data points for the plurality of patients, wherein each patient-related data point is associated with a respective threshold condition and a respective ranking score;

ranking, in real-time, by the one or more processors, for the plurality of patients, the plurality of patient-related data points, based on each respective threshold condition and each respective ranking score to determine a priority of each patient-related data point;

generating, in real-time, by the one or more processors, based on the priority of each patient-related data point of the patient-related data points, at least one actionable medical directive related to at least one patient of the plurality of patients, wherein the at least one actionable medical directive is configured to cause at least one real-time operational change in the way that the healthcare facility services the at least one patient of the plurality of patients; and causing to present, in real-time, by the one or more processors, on a mobile computing device, the at least one actionable medical directive related to the at least one patient of the plurality of patients.

3. The system and method recited above, wherein the plurality of data tables are organized according to data type.

4. The system and method recited above, wherein the database layer includes at least one real-time actionable data (RAD) database.

5. The system and method recite above, further comprising at least one security domain configured to secure one or more of the plurality of data tables.

6. The system and method recited above, wherein the database layer includes at least one security domain configured to secure one or more of the plurality of data tables and a RAD database.

7. The system and method recited above, further including a centralized RAD database external to the at least one security domain and configured to aggregate data from the RAD database of each of the at least one security domain.

8. The system and method recited above, wherein at least one of the plurality of distinct data collection services is a medical measurement device.

Publications cited throughout this document are hereby incorporated by reference in their entirety. While one or more embodiments of the present disclosure have been described, it is understood that these embodiments are illustrative only, and not restrictive, and that many modifications may become apparent to those of ordinary skill in the art, including that various embodiments of the inventive methodologies, the inventive systems/platforms, and the inventive devices described herein can be utilized in any combination with each other. Further still, the various steps may be carried out in any desired order (and any desired steps may be added and/or any desired steps may be eliminated).

The invention claimed is:

1. A system, comprising:

At least one processing system, comprising:

A database layer comprising:

at least one security domain configured to secure one or more of a plurality of data tables of a plurality of distinct data collection services having a plurality of distinct service specific data formats, At least one real-time actionable data (RAD) database of each of the at least one security domain, and A centralized RAD database external to the at least one security domain and configured to aggregate data from each of the at least one RAD database of the at least one security domain;

The database layer being at least configured to:

Query patient-related data from the plurality of data tables of the plurality of distinct data collection services having a plurality of distinct service specific data formats and secured by the at least one security domain;

wherein the patient-related data comprises:

i) a plurality of patient satisfaction surveys from a plurality of patients of a healthcare system, wherein each patient satisfaction survey of the plurality of patient satisfaction surveys comprise patient satisfaction survey responses, and ii) at least one task completion metric representing completion of at least one task in at least one prior matching of a particular resource to a particular healthcare need of at least one past patient;

normalize the patient-related data with respect to the plurality of distinct service specific data formats to produce common format normalized patient-related data;

store the common format normalized patient-related data in at least one respective RAD database within the at least one respective security domain of the at least one security domain; and store the common format normalized patient-related data in the centralized RAD database external to the at least one security domain to aggregate data from the at least one respective RAD database within at least one respective security domain of the at least one security domain;

an algorithmic processing layer that is at least configured to:

determine, in real-time, using the common format normalized patient-related data in the centralized RAD database, at least one patient-specific service preference associated with at least one particular patient of the plurality of patients based at least in part on at least one response of at least one particular patient satisfaction survey of the plurality of patient satisfaction surveys;

wherein the at least one particular patient satisfaction survey is associated with the at least one particular patient;

determine, in real-time, using the common format normalized patient-related data in the centralized RAD database, at least one healthcare system-related data metric of at least one healthcare service task based at least in part on the patient satisfaction survey responses and the at least one task completion metric;

predict, in real-time, for the at least one particular patient of the plurality of patients, at least one particular combination of healthcare resources in the healthcare system based at least in part on:

i) the at least one patient-specific service preference, and ii) at least one prior allocation of resources to the at least one particular patient;

iteratively generate, in real-time, at least one actionable directive related to resource deployment across the healthcare system to perform at least one healthcare service task with the at least one particular patient by iteratively matching each resource of the at least one particular combination of resources to each particular patient of the at least one particular patient based at least in part on:

i) the at least one healthcare system-related data metric of the at least one healthcare service task, and ii) a resource utilization capacity of the at least one healthcare resource; and a visualization layer that is at least configured to cause a display to dynamically display, in real-time, a dashboard interface for the at least one healthcare system;

wherein the dashboard interface comprises at least one interface element representing the at least one actionable directive so as to recommend the at least one particular combination of resources to each particular patient of the at least one particular patient.

2. The system of claim 1, wherein the at least one actionable directive comprises a matching of a plurality of resources across five or more patients, across ten or more patients, or across fifteen or more of the plurality of patients according to a respective utilization capacity of each resource of the plurality of resources.

3. The system of claim 1, wherein the algorithmic processing layer is further configured to analyze the patient-related data for the plurality of patients according to a look-up table correlating a score to each of the plurality of patient satisfaction surveys associated with each patient of the plurality of patients, each task completion of the task completion metrics associated with each patient of the plurality of patients, or both according to at least one threshold condition.

4. The system of claim 1, wherein at least one of the plurality of distinct data collection services comprises at least one medical measurement device located at one or more locations associated with the plurality of patients of the healthcare system.

5. The system of claim 1, wherein the patient-related data comprises:

i) patient visit data identifying a time and duration of a visit of the at least one healthcare system of a respective patient of the plurality of patients, ii) patient status data identifying a status of the respective patient of the plurality of patients of the at least one healthcare system, iii) patient condition data identifying condition measurements for the respective patient of the plurality of patients of the at least one healthcare system, iv) patient location data identifying a location of the respective patient of the plurality of patients of the at least one healthcare system, or v) patient service data identifying medical services provided to the respective patient of the plurality of patients.

6. The system of claim 1, wherein the at least one actionable directive comprises a modification to at least one resource deployment at one or more locations associated with the plurality of patients of the healthcare system associated with the at least one patient of the plurality of patients.

7. A method, comprising:

obtaining, by one or more processors, patient-related data from a plurality of data tables of a plurality of distinct data collection services having a plurality of distinct service specific data formats and secured by at least one security domain, wherein the patient-related data comprises:

i) a plurality of patient satisfaction surveys from a plurality of patients of a healthcare system, wherein each patient satisfaction survey of the plurality of patient satisfaction surveys comprise patient satisfaction survey responses, and ii) at least one task completion metric representing completion of at least one task in at least one prior matching of a particular resource to a particular healthcare need of at least one past patient;

normalizing, by the one or more processors, the patient-related data with respect to the plurality of distinct service specific data formats to produce common format normalized patient-related data;

storing, by the one or more processors, the common format normalized patient-related data in at least one respective real-time actionable data (RAD) database within at least one respective security domain of the at least one security domain;

storing, by the one or more processors, the common format normalized patient-related data in a centralized RAD database external to the at least one security domain to aggregate data from the at least one respective RAD database within at least one respective security domain of the at least one security domain;

determining, in real-time, by the one or more processors, using the common format normalized patient-related data in the centralized RAD database, at least one patient-specific service preference associated with at least one particular patient of the plurality of patients based at least in part on at least one response of at least one particular patient satisfaction survey of the plurality of patient satisfaction surveys;

wherein the at least one particular patient satisfaction survey is associated with the at least one particular patient;

determining, in real-time, by the one or more processors, using the common format normalized patient-related data in the centralized RAD database, at least one healthcare system related data metric of at least one healthcare service task associated with the plurality of patients based at least in part on the patient satisfaction survey responses and the at least one task completion metric;

predicting, in real-time, by the one or more processors, for the at least one particular patient of the plurality of patients, at least one particular combination of healthcare resources in the healthcare system based at least in part on:
i) the at least one patient-specific service preference, and
ii) at least one prior allocation of resources to the at least one particular patient;

iteratively generating, in real-time, by the one or more processors, at least one actionable directive related to resource deployment across the healthcare system to perform at least one healthcare service task with the at least one particular patient by iteratively matching each resource of the at least one particular combination of resources to each particular patient of the at least one particular patient based at least in part on:
i) the at least one healthcare system-related data metric of the at least one healthcare service task, and
ii) a resource utilization capacity of the at least one healthcare resource; and causing to dynamically display, in real-time, by the one or more processors, on a computing device, a dashboard interface for the at least one healthcare system;

wherein the dashboard interface comprises at least one interface element representing the at least one actionable directive so as to recommend the at least one particular combination of resources to each particular patient of the at least one particular patient.

8. The method of claim 7, wherein the at least one actionable directive comprises a matching of a plurality of resources across five or more patients, across ten or more patients, or across fifteen or more patients of the plurality of patients according to a respective utilization capacity of each resource of the plurality of resources.

9. The method of claim 7, wherein the analyzing the patient-related data for the plurality of patients includes using a look-up table to correlate a score to each of the plurality of patient satisfaction surveys associated with each patient of the plurality of patients, each task completion of the task completion metrics associated with each patient of the plurality of patients, or both according to at least one threshold condition.

10. The method of claim 7, wherein at least one of the plurality of distinct data collection services comprises at least one medical measurement device located at one or more locations associated with the plurality of patients of the healthcare system.

11. The method of claim 7, wherein the patient-related data comprises:
i) patient visit data identifying a time and duration of a visit of the at least one healthcare system of a respective patient of the plurality of patients,
ii) patient status data identifying a status of the respective patient of the plurality of patients of the at least one healthcare system,
iii) patient condition data identifying condition measurements for the respective patient of the plurality of patients of the at least one healthcare system,
iv) patient location data identifying a location of the respective patient of the plurality of patients of the at least one healthcare system, or
v) patient service data identifying medical services provided to the respective patient of the plurality of patients.

12. The method of claim 7, wherein the at least one actionable directive comprises a modification to at least one resource deployment at one or more locations associated with the plurality of patients of the healthcare system associated with the at least one patient of the plurality of patients.

13. A method, comprising: determining, by one or more processors, a selection of at least one patient of a plurality of patients with a hospital tracking interface of a computing device associated with a user;

wherein the hospital tracking interface comprises a graphical user interface (GUI) that allows a user to view and select information related to the plurality of patients being serviced by a healthcare system;

communicating, by the one or more processors, the selection to one or more real-time actionable database (RAD) processors, wherein the one or more RAD processors are configured to:
obtain patient-related data from a plurality of data tables of a plurality of distinct data collection services having a plurality of distinct service specific data formats and secured by at least one security domain, wherein the patient-related data comprises:
i) a plurality of patient satisfaction surveys from a plurality of patients of the healthcare system, wherein each patient satisfaction survey of the plurality of patient satisfaction surveys comprise patient satisfaction survey responses, and
ii) at least one task completion metric representing completion of at least one task in at least one prior matching of a particular resource to a particular healthcare need of at least one past patient;

normalize the patient-related data with respect to the plurality of distinct service specific data formats to produce common format normalized patient-related data;

store the common format normalized patient-related data in at least one respective RAD database within at least one respective security domain of the at least one security domain;

store the common format normalized patient-related data in a centralized RAD database external to the at least one security domain to aggregate data from the at least one respective RAD database within at least one respective security domain of the at least one security domain;

determine, in real-time, using the common format normalized patient-related data in the centralized RAD database, at least one patient-specific service preference associated with at least one particular patient of the plurality of patients based at least in part on at least one response of at least one particular patient satisfaction survey of the plurality of patient satisfaction surveys;

wherein the at least one particular patient satisfaction survey is associated with the at least one particular patient;

determine, in real-time, using the common format normalized patient-related data in the centralized RAD database, at least one healthcare system-related data metric of at least one healthcare service task-based at least in part on the patient satisfaction survey responses and the at least one task completion metric;

predict, in real-time, for the at least one particular patient of the plurality of patients, at least one particular combination of healthcare resources in the healthcare system based at least in part on:
  i) the at least one patient-specific service preference, and
  ii) at least one prior allocation of resources to the at least one particular patient;

iteratively generate, in real-time, at least one actionable directive related to resource deployment across the healthcare system to perform at least one healthcare service task with the at least one particular patient by iteratively matching each resource of the at least one particular combination of resources to each particular patient of the at least one particular patient based at least in part on:
  i) the at least one healthcare system-related data metric of the at least one healthcare service task, and
  ii) a resource utilization capacity of the at least one healthcare resource; and transmit, in real-time, the at least one actionable directive to a mobile computing device; and causing to dynamically display, in real-time, by the one or more processors, on the computing device associated with the user, a dashboard interface for the at least one healthcare system;

wherein the dashboard interface comprises at least one interface element representing the at least one actionable directive so as to recommend the at least one particular combination of resources to each particular patient of the at least one particular patient.

14. The method of claim 13, wherein the at least one actionable directive comprises a modification to at least one resource deployment at one or more locations associated with the plurality of patients of the healthcare system associated with the at least one patient of the plurality of patients.

15. The system of claim 1, wherein the algorithmic processing layer is further configured to:
  determine, in real-time, for the at least one patient of the plurality of patients, at least one patient-related equipment need based at least in part on the patient satisfaction survey responses associated with the at least one patient; and
  wherein the iterative matching comprises a matching of a particular combination of resources to the at least one patient based at least in part on:
    i) the at least one patient-related equipment need,
    ii) the at least one healthcare system-related data metric, and
    iii) a utilization capacity of resources of the at least one healthcare system.

16. The method of claim 7, further comprising:
  determining, in real-time, by the one or more processors, for the at least one patient of the plurality of patients, at least one patient-related equipment need based at least in part on the patient satisfaction survey responses associated with the at least one patient; and
  wherein the iterative matching comprises a matching of a particular combination of resources to the at least one patient based at least in part on:
    i) the at least one patient-related equipment need,
    ii) the at least one healthcare system-related data metric, and
    iii) a utilization capacity of resources of the at least one healthcare system.

17. The method of claim 13, further comprising:
  determining, in real-time, by the one or more processors, for the at least one patient of the plurality of patients, at least one patient-related equipment need based at least in part on the patient satisfaction survey responses associated with the at least one patient; and
  wherein the iterative matching comprises a matching of a particular combination of resources to the at least one patient based at least in part on:
    i) the at least one patient-related equipment need,
    ii) the at least one healthcare system-related data metric, and
    iii) a utilization capacity of resources of the at least one healthcare system.

* * * * *